(12) United States Patent
Li et al.

(10) Patent No.: US 7,304,168 B2
(45) Date of Patent: Dec. 4, 2007

(54) PHOTO-CAGED FLUORESCENT MOLECULES

(75) Inventors: Wen-Hong Li, Dallas, TX (US); YuRui Zhao, Dallas, TX (US)

(73) Assignee: Board of Regents, University of Texas System, Austin, TX (US)

( * ) Notice: Subject to any disclaimer, the term of this patent is extended or adjusted under 35 U.S.C. 154(b) by 104 days.

(21) Appl. No.: 10/917,859

(22) Filed: Aug. 13, 2004

(65) Prior Publication Data

US 2005/0042662 A1    Feb. 24, 2005

Related U.S. Application Data

(60) Provisional application No. 60/494,994, filed on Aug. 14, 2003.

(51) Int. Cl.
*C07D 311/00* (2006.01)
*C07D 405/00* (2006.01)
*C07D 409/00* (2006.01)
*C07D 411/00* (2006.01)

(52) U.S. Cl. ..................... 549/289; 548/525
(58) Field of Classification Search ............... 549/289; 548/525
See application file for complete search history.

(56) References Cited

U.S. PATENT DOCUMENTS

| | | | |
|---|---|---|---|
| 5,635,608 A | 6/1997 | Haugland et al. | |
| 5,830,912 A | 11/1998 | Gee et al. | |
| 5,955,604 A * | 9/1999 | Tsien et al. | 540/222 |
| 6,472,205 B1 | 10/2002 | Tsien et al. | |

OTHER PUBLICATIONS

Wu et al., "Multicolor labeling of cells using Qdot streptavidin conjugates", Quantum Dot Corporation, pp. 10-11.*
Rash et al., "Grid-mapped freeze-fracture analysis of gap junctions in gray and white matter of adult rat central nervous system, with evidence for a "panglial syncytium" that is not coupled to neurons", The Journal of Comparative Neurology, vol., 388, pp. 265-292.*
Campbell et al., Biology, second edition, 1990, p. 76.*
Adams SR, Tsien RY. Controlling cell chemistry with caged compounds. Annu Rev Physiol. 1993;55:755-84.
Ando H, Furuta T, Tsien RY, Okamoto H. Photo-mediated gene activation using caged RNA/DNA in zebrafish embryos. Nat Genet. Aug. 2001;28(4):317-25.
Brown EB, Shear JB, Adams SR, Tsien RY, Webb WW. Photolysis of caged calcium in femtoliter volumes using two-photon excitation. Biophys J. Jan. 1999;76(1 Pt 1):489-99.
Canepari M, Nelson L, Papageorgiou G. Corrie JE, Ogden D. Photochemical and pharmacological evaluation of 7-nitroindolinyl- and 4-methoxy-7-nitroindolinyl-amino acids as novel, fast caged neurotransmitters. J Neurosci Methods. Nov. 15, 2001;112(1):29-42.

Deleze J. Delage B, Hentati-Ksibi O, Verrecchia F, Herve JC. Fluorescence recovery after photobleaching. Methods Mol Biol. 2001;154:313-27.
El-Fouly MH, Trosko JE, Chang CC. Scrape-loading and dye transfer. A rapid and simple technique to study gap junctional intercellular communication. Exp Cell Res. Feb. 1987;168(2):422-30.
Fedoryak OD, Dore TM. Brominated hydroxyquinoline as a photolabile protecting group with sensitivity to multiphoton excitation. Org Lett. Oct. 3, 2002;4(20):3419-22.
Furuta T, Wang SS, Dantzker JL, Dore TM, Bybee WJ, Callaway EM, Denk W, Tsien RY. Brominated 7-hydroxycoumarin-4-ylmethyls: photolabile protecting groups with biologically useful cross-sections for two photon photolysis. Proc Natl Acad Sci U S A. Feb. 16, 1999;96(4):1193-200.
Grynkiewicz G, Poenie M, Tsien RY. A new generation of Ca2+ indicators with greatly improved fluorescence properties. J Biol Chem. Mar. 25, 1985;260(6):3440-50.
Harris AL. Emerging issues of connexin channels: biophysics fills the gap. Q Rev Biophys. Aug. 2001;34(3):325-472.
Krafft GA, Sutton WR, Cummings RT. Photoactivable Fluorophores. 3. Syntehsis and Photoactivation of Fluorogenic Difunctionalized Fluoresceins. J. Am. Chem. Soc. 1988;110:301-303.
LI W, Llopis J, Whitney M, Zlokarnik G, Tsien RY. Cell-permeant caged InsP3 ester shows that Ca2+ spike frequency can optimize gene expression. Nature. Apr. 30, 1998; 392(6679):936-41.
Loewenstein WR. Junctional intercellular communication and the control of growth. Biochim Biophys Acta. Feb. 4, 1979;560(1):1-65.
Matsuzaki M, Ellis-Davies GC, Nemoto T, Miyashita Y, Iino M, Kasai H. Dendritic spine geometry is critical for AMPA receptor expression in hippocampal CA1 pyramidal neurons. Nat Neurosci. Nov. 2001;4(11):1086-92.
Meda P. Assaying the molecular permeability of connexin channels. Methods Mol Biol. 2001;154:201-24.
Mitchison TJ, Sawin KE, Theriot JA, Gee K, Mallavarapu A. Caged fluorescent probes. Methods Enzymol. 1998;291:63-78.
Peters R. Nuclear envelope permeability measured by fluorescence microphotolysis of single liver cell nuclei. J Biol Chem. Oct. 10, 1983;258(19):11427-9.
Politz JC. Use of caged fluorochromes to track macromolecular movement in living cells. Trends Cell Biol. Jul. 1999;9(7):284-7.
Rozental R, Srinivas M, Spray DC. How to close a gap junction channel. Efficacies and potencies of uncoupling agents. Methods Mol Biol. 2001;154:447-76.

(Continued)

*Primary Examiner*—Margaret D. Seamani
*Assistant Examiner*—Niloofar Rahmani
(74) *Attorney, Agent, or Firm*—Jackson Walker L.L.P.

(57) ABSTRACT

A class of photo-caged and cell permeable fluorescent molecules having high uncaging cross sections, robust fluorescence enhancement, and flexible chemistry for bioconjugation. Some of the photo-caged fluorescent molecules are derived from 6-chloro-7-hydroxy-coumarin 3-carboxamide. The fluorescent molecules are useful for cellular imaging applications and particularly for tracing the molecular transfer between cellular gap junctions. The fluorescent molecules also have an emission wavelength that spectrally complements with the emission wavelength of other fluorophores, enabling simultaneous multi-color imaging.

10 Claims, 22 Drawing Sheets

OTHER PUBLICATIONS

Theriot JA, Mitchison TJ. Actin microfilament dynamics in locomoting cells. Nature. Jul. 11, 1991;352(6331):126-31.

Van Rijen HV, Wilders R, Rook MB, Jongsma HJ. Dual patch clamp. Methods Mol Biol. 2001;154:269-92.

Verselis V, White RL, Spray DC, Bennett MV. Gap junctional conductance and permeability are linearly related. Science. Oct. 24, 1986;234(4775):461-4.

Wade MH, Trosko JE, Schindler M. A fluorescence photobleaching assay of gap junction-mediated communication between human cells. Science. Apr. 25, 1986;232(4749):525-8.

Zlokarnik G, Negulescu PA, Knapp TE, Mere L, Burres N, Feng L, Whitney, Roemer K, Tsien RY. Quantitation of transcription and clonal selection of single living cells with beta-lactamase as reporter. Science. Jan. 2, 1998;279(5347):84-8.

* cited by examiner a. Zn(CN)$_2$, HCl(g). Et$_2$O, 0 °C; then Et$_2$O, H$_2$O, 100 °C, 12%;
b. Malonic acid, aniline (cat), pyridine, 44%;
c. (1)SOCl$_2$, cat.DMF, CH$_2$Cl$_2$; (2) H-D-Glu(OMe)-OMe (for *1a*), or H-D-Glu(OtBu)-OtBu (for *1b*), TEA, CH$_2$Cl$_2$, 67%;
d. NPE bromide (for *2a* & *2d*), or NB bromide (for *2b*), or DMNB bromide (for *2c*), DIEA, CH$_2$Cl$_2$, 65~75%;
e. (1) *2d*, TFA, Et$_3$SiH, CH$_2$Cl$_2$; (2) AcOCH$_2$Br, DIEA, CH$_3$CN, 60%.

NPE-HCC-NHS

NPE-HCC-TFP

NPE-HCC-Gly-NHS

NPE = 1-(2-Nitrophenyl)ethyl =

PHOTO-CAGED FLUORESCENT MOLECULES

This application claims priority to U.S. Provisional Patent Application Ser. No. 60/494,994, entitled "PHOTO-CAGED FLUORESCENT MOLECULES," filed on Aug. 14, 2003, having Wen-Hong Li and YuRui Zhao, listed as the inventors, the entire content of which is hereby incorporated by reference.

BACKGROUND

The present invention is generally related to fluorescent molecules for cellular imaging applications and, in particular, to photo-caged fluorescent molecules which are cell permeable and useful for the study of cellular imaging applications and tracing molecular transfer in cellular gap junctions.

Photo-caged fluorescent dyes have wide applications in tracking the spatiotemporal dynamics of molecular movements in biological systems. These caged tracers are weakly or non-fluorescent when key functional groups of fluorophores are masked by photo-labile protecting groups, or cages. Photo-activation "uncages" the molecule by removing the protecting group and abruptly switches on the fluorescence of the parent dyes. By selectively photoactivating labeled molecules present in a certain area of a cell, the progression of the fluorescent signal can then be tracked over time as it moves away from the "uncaging" site into the dark surrounding area. (Adams, et al., 1993; Politz, 1999; Mitchison, et al., 1998).

Caged fluorochromes are covalently linked to a macromolecule and then, once inside the cell, the caging moiety is usually removed by a pulse of long-wavelength ultraviolet ("UV") light ranging from about 330 nm to 390 nm. Caging groups are typically designed to be released by long-wavelength UV light rather than short-wavelength UV light because long-wavelength UV light is less harmful to cells. To minimize cell damage, the use of a minimal amount of UV illumination is desirable. At the same time, an essential requirement of a caged fluorophore is that its fluorescence excitation wavelength does not overlap with the wavelength of UV light used for uncaging.

Macromolecules labeled with caged fluorochromes are usually microinjected into the cell because the macromolecules are impermeable to the cell membrane. Small caged fluorescent molecules that are cell permeable or can be loaded into cells to high concentrations have not been described yet. However, some oligonucleotides labeled with caged fluorochromes can be taken up by cultured cells alone or after being complexed with cationic lipids. (Politz, 1999).

U.S. Pat. No. 5,830,912 to Gee et al. describes a class of fluorescent dyes derived from 6,8-difluoro-7-hydroxycoumarin, some of which may be photo-caged. However, the excitation maximum of most of the compounds related to 6,8-difluoro-7-hydroxycoumarin is at about 370 nm, which overlaps with the wavelengths of UV light typically used for uncaging. A few compounds described herein can be excited above 400 nm, but the uncaging cross sections of these compounds have not been described, neither the cell permeability has been described. Thus, these molecules are not ideally suited for use as photo-caged fluorescent molecules.

U.S. Pat. No. 5,635,608 to Haugland et al. describes caged compounds with a photoremoveable α-carboxy-substituted o-nitrobenzyl group. Except for the disclosure of one rhodamine derivative, the disclosed compounds are not fluorophores. Rather, they are biomolecules with a caging group directly attached, so that photoactivation restores the bioactivity of the molecule but does not result in fluorescence.

Fluorescent probes and tracers used in cellular imaging may be used to study the transfer of molecules through gap junctions in cells. Malfunctions of intercellular communications through connexin channels and gap junctions are associated with diseases such as deafness, peripheral neuropathy, cataracts, hereditary malfunctions of the cardiovascular system, and Chagas' disease. Thus, it is of pharmaceutical interest to develop high throughput screening technology for isolating specific modulators of gap junctions.

Several techniques exist for studying gap junction transfers. Microinjection of membrane-impermeant tracers such as Lucifer Yellow or neurobiotin is a classical technique for assaying molecular permeability of connexin channels (Meda, 2001). It allows for selective loading of tracers into cells of choice. However, the method is associated with a number of major limitations. First, cell membranes are usually damaged during the operation, so special skill and extra care are needed to minimize cell injury. Also, only a limited number of cells can be injected at a time, so it is not convenient to study intercellular communications in cell populations or tissue preparations. Finally, the microinjection process may disrupt the extracellular and intracellular concentrations of other molecules affecting gap junction permeability. For example, extracellular calcium ion ("$Ca^{2+}$") concentrations are typically greater than 1 mM, which is more than $10^4$ times higher than intracellular $Ca^{2+}$ concentrations, which are typically less than 0.1 µM at the resting state. It is very difficult to maintain the intracellular $Ca^{2+}$ concentration at a normal physiological level during microinjection. Thus, studies of fluctuations in concentration of molecules such as $Ca^{2+}$ in relation to gap junction permeability may be adversely affected. The technique known as "scrape loading" suffers from similar drawbacks (el-Fouly, et al., 1987).

An additional method, known as the dual whole-cell patch clamp method, has also been applied to determine kinetics and conductance of gap junctions in both primary cultures and cell lines expressing exogenous connexins (Van Rijen, et al., 2001). This method has the known advantages of the whole-cell patch clamp method, which uses fewer electrodes and generates more stable recordings. However, the accuracy of junctional current measurement is affected by the relative values of uncompensated electrode resistances, non-junctional resistances, junctional resistance and seal resistances (Harris, 2001). Thus, caution must be taken in order to maintain an accurate measurement. This method has also been used for dye-passage experiments due to the low diffusional barrier of the patch pipette. While the technique offers some abilities to alter cytoplasmic constituents, it can also cause problems when concentrations of cellular ions, such as $Ca^{2+}$, must be accurately controlled, or when certain important cytoplasmic factors should be prevented from being diluted out in the pipette.

Fluorescence Recovery After Photobleaching ("FRAP") is another technique for tracking molecular movements in cells (Deleze, et al., 2001). At the present time, the laser power of most commercially available confocal systems may be adequate for spot photobleaching, but generally much higher laser power is required for rapid photobleaching of whole cells as required by the gap junction FRAP ("GJ-FRAP") technique. This intense laser illumination may damage cells. Moreover, the GJ-FRAP technique maybe incompatible with multi-color imaging when other biochemical changes inside cells need to be studied by fluorescent sensors.

Ideally, caged fluorophores used in cellular imaging applications should be efficiently photoactivated at low levels of UV radiation, be capable of localized uncaging, have robust fluorescence enhancement after uncaging, and have flexible chemistry for bioconjugation and cellular delivery. They should also be cell permeable, particularly for the study of intercellular communications, and compatible with other imaging techniques to allow simultaneous studies.

SUMMARY

The present invention is generally related to a class of photo-caged fluorescent molecules useful for cellular imaging applications. In particular embodiments, the caged fluorophores are derived from 6-chloro-7-hydroxy-coumarin 3-carboxamide. These molecules demonstrate high efficiency of photoactivation, strong absorption above 400 nm, cell permeability, and insensitivity to pH fluctuations in cytosolic or physiological solutions (Zlokarnik, et al., 1998). The caged fluorophores are capable of localized uncaging and are also cell permeable, making them ideal for studying the transfer of molecules between gap junctions in cells. Furthermore, the caged fluorophores emit at a wavelength that differs from other fluorescent dyes, enabling simultaneous photo-uncaging and multi-color imaging in live cells.

One general structure of an embodiment of the caged fluorophores is represented as:

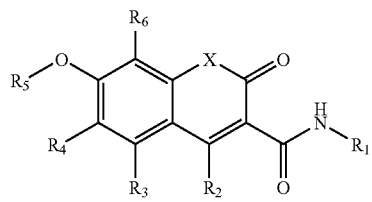

wherein X is O or N—$R_a$, wherein $R_a$ can be H or alkyl chains up to 6 carbons; $R_1$ is any linear or branched alkyl chains up to 20 carbon atoms or any one of the 20 amino acids either in D or L configuration; $R_2$ is H, alkyl groups up to 6 carbon atoms, F, Cl, Br, $CF_3$, $CHF_2$, or $CH_2F$; $R_3$, $R_4$ and $R_6$ are independently H, F, Cl, or Br, but when X is O, $R_4$ and $R_6$ are not both F; and $R_5$ is a caging group.

Many different structures can be used as caging groups for the fluorophores of the present invention. In particular embodiments, the caging groups are 1-(2-nitrophenyl)ethyl ("NPE"), 2-nitrobenzyl ("NB"), and 4,5-dimethoxy-2-nitrobenzyl ("DMNB").

The caged fluorophores of the present invention have remarkably high uncaging cross sections. The uncaging cross section is a measure of the efficiency of photolysis. It is equal to the product of the quantum yield of uncaging ($Q_u$) and the extinction coefficient ($\epsilon$) of the molecule at the wavelength used for photolysis. This wavelength is preferably above 350 nm for live cell applications. Previously reported caged fluorophores have uncaging cross sections on the order of 100 when photolyzed at 350 nm or above (Krafft, et al., 1988). The caged fluorophores of the current invention possess high uncaging cross sections of over 6000. In addition, they show at least a 200 fold fluorescent enhancement after photouncaging. The caged fluorophores of the current invention actually demonstrate "substrate assisted photolysis." Thus, the caged structures improve the efficiency of photolysis of the caging groups by enhancing the absorption of UV light. Higher uncaging cross sections and greater efficiencies of photolysis are desirable because the fluorescence can be effectively activated while minimizing side effects of UV illumination on live specimens. Greater increases in fluorescent signals produce higher contrast optical marking. Photoactivation, or photo-uncaging, of the fluorophores can also be targeted to a localized area by limiting the size of the UV-illuminated spot.

The current caged fluorophores may also be activated by two-photon photoactivation at even longer wavelengths. During two-photon photoexcitation, the molecules absorb two photons nearly simultaneously to reach the excited state. The combined energy of two photons at lower energy is equivalent to one photon at the UV wavelength. Using lower energy light minimizes the risk of damage to the cells. In addition, because two-photon uncaging requires high fluxes of protons in a very short period of time, it only occurs at the focal point. This provides a high resolution focal uncaging effect which is often desirable when studying local signaling in cells.

The 3-carboxamide group of the caged fluorophores extends the excitation maximum of the fluorophore to about 408 nm, allowing its fluorescence to be monitored through excitation at wavelengths of 408 nm or above. Thus, the fluorescence excitation wavelengths barely overlap with the photoactivation wavelengths.

In particular embodiments, the caged fluorophores are derivatives of coumarin. Coumarin derivatives emit blue light, whereas previously reported caged fluorophores typically emit in the green or red regions of the spectra (Mitchison, et al., 1998; Theriot, et al., 1991). Thus, the present caged coumarin derivatives maybe used in combination with other fluorescent dyes or sensors which emit at longer wavelengths, allowing researchers to expand the fluorescent imaging window and carry out photo-uncaging and multi-color imaging simultaneously in live cells.

In additional embodiments, the caged fluorophores may be substituted with additional reactive groups to create derivatives, such as N-hydroxysuccinamide ester or maleimide derivatives, which allow conjugation with molecules such as proteins, antibodies, peptides, DNA, RNA, oligonucleotides, dextrans, or any other molecules containing reactive amino or thiol functionalities.

FIG. 1 shows a schematic of general structures and fluorescent properties of a cell permeable and caged fluorophore, labeled as NPE-HCCC2-AM. After diffusing through the plasma membrane of the cell, the caged fluorophore is subjected to intracellular hydrolysis, as shown by the structure NPE-HCCC2. This molecule has a low fluorescence quantum yield of 0.0025. After the molecule is uncaged with UV light, as shown by the structure HCCC2, it has a much higher fluorescence quantum yield.

FIG. 2 shows a general schematic of an imaging assay of cell-cell gap junctional communication. First, cells are loaded with the cell permeable and caged fluorophore NPE-HCCC2-AM. After a localized photolysis of NPE-HCCC2 in a "donor" cell among coupled cells, digital fluorescence microscopy is used to provide quantitative information about dye transfer between cells. Black dots represent uncaged HCCC2 and open circles represent caged NPE-HCCC2.

Because the current caged fluorophores can be uncaged in a localized area, are cell permeable, and can cross gap junctions, they have even wider applications in cell biology research. First, they do not have to be delivered into cells through invasive techniques such as microinjection or electroporation. Second, they make it feasible to obtain paired data under both control and test conditions and to perform a set of experiments on the same coupled cells over a period of time. Table 1 below summarizes the advantages of using localized photo-uncaging of fluorophores to study the permeability of gap junctions, versus the traditional techniques of microinjection, dual whole cell patch clamping, and FRAP.

TABLE 1

|  | Microinjection of tracers | FRAP | Dual whole cell patch clamping | Localized uncaging of permeable dyes |
|---|---|---|---|---|
| Invasiveness | Invasive | Intense illumination & photo-damage | Invasive | Non-invasive |
| Cell integrity | Compromised | Maintained (if dyes are cell permeable) | Compromised | Maintained |
| Temporal resolution | Low | Good | Very high | Good |
| Simplicity of set-up and execution | Special technique, limited cells | Require high power laser | Technically demanding & time consuming | Easy, applicable to cell populations or tissues |
| Quantification of molecular transfer rates | Reliable only if cells recover very rapidly | Reliable if no photo-damage | Conductance does not always reflect molecular transfer, problematic in well-coupled cells from the interference of series resistance | Reliable & allow multiple measurements in coupled cell pairs |
| Multi-color imaging | Feasible | Difficult | Feasible | Feasible |

Thus, localized uncaging of the fluorophores can be used as a powerful and convenient method for studying intercellular communication in intact cell populations. The caged and cell permeable fluorophores are first loaded into fully intact cells. Localized uncaging of the fluorophores can then be performed in order to selectively mark individual cells amongst coupled cells. Subsequent fluorescent imaging and data analysis then provide quantitative information on the molecular transfer rates across gap junctions of coupled cells.

Figure 17:
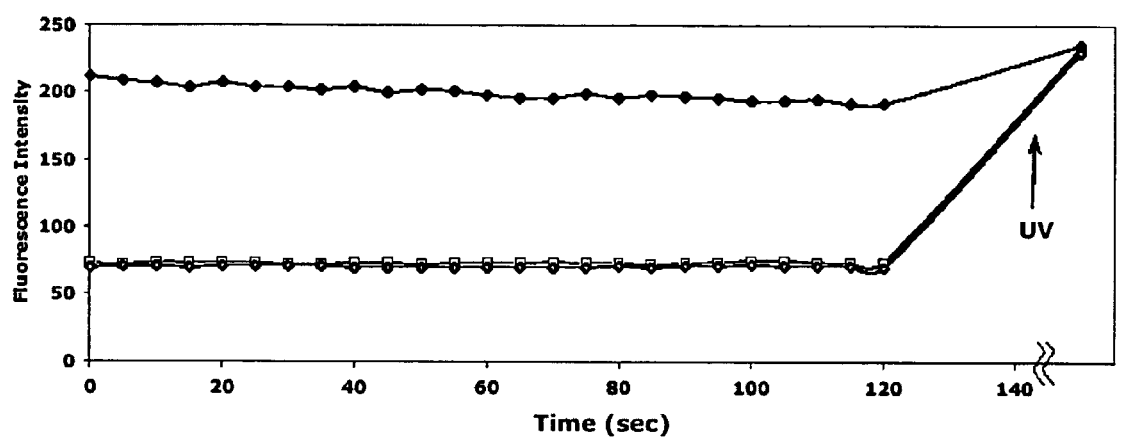

FIG. 17 shows the time course of coumarin fluorescence intensities of cells, one of which was initially subjected to two photon uncaging at 740 nm, wherein alll cells were later uncaged by UV light and imaged using 800 nm excitation.

Figure 18:
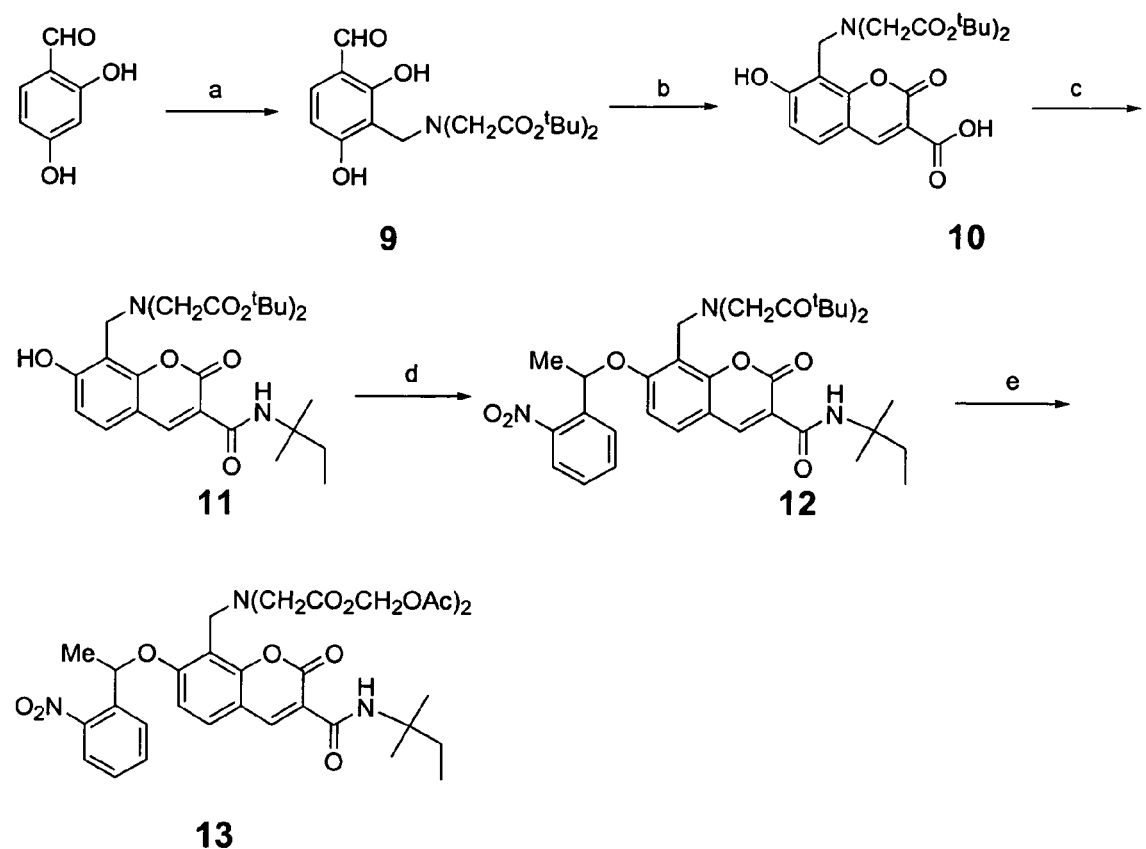

FIG. 18 shows (a) $(CH_2O)_n$, $NH(CH_2CO_2{}^tBu)_2$, $CH_3/CN/H_2O$, 2,4-dihydroxybenzaldehyde, 80° C., 87%; (b) Malonic acid, aniline (cat.), pyridine, 79%; (c) Oxalyl chloride, DMF (cat.), t-amylamine, 30%; (d) NPE-Br, DIEA, $CH_3CN$, 70° C., 44%; (e) (1) TFA, $Et_3SiH$, $CH_2Cl_2$; (2) AM bromide, DIEA, $CH_3CN$, 21% for 2 steps.

Figure 19:
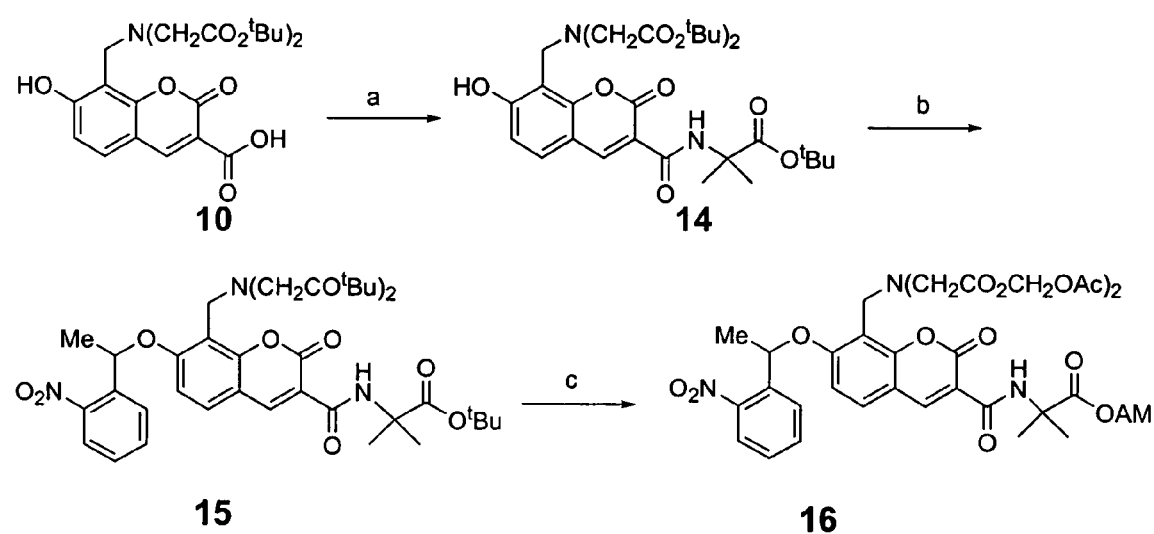

FIG. 19 shows (a) Oxalyl chloride, DMF (cat.), H-Aib-O$^t$Bu.HCl, $Et_3N$, 68%; (b) NPE-Br, DIEA, $CH_3CN$, 60° C., 68%; (c) (1) TFA, $Et_3SiH$, $CH_2Cl_2$; (2) AM bromide, DIEA, $CH_3CN$, 25% for 2 steps.

Figure 20:
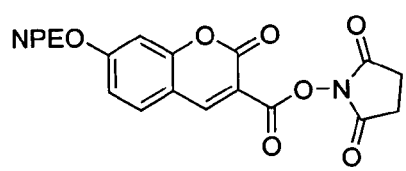
Figure 20:
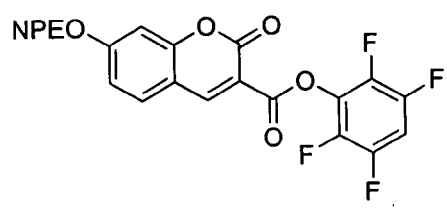
Figure 20:
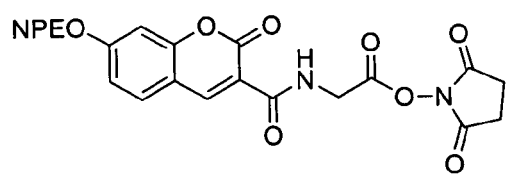
Figure 20:

FIG. 20 shows some examples of amine reactive caged coumarin derivatives for bio-conjugations.

Figure 21:
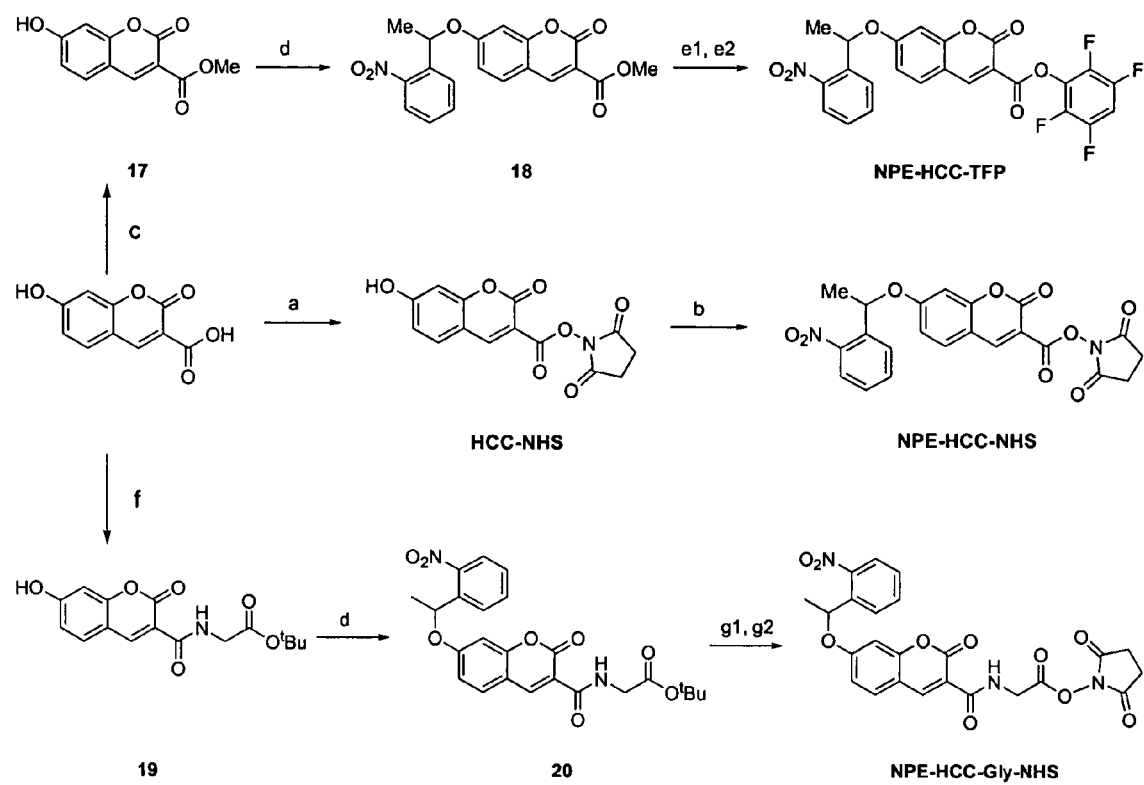

FIG. 21 shows the syntheses of amine reactive caged coumarin derivatives. (a) N-hydroxysuccinimide trifluoroacetate, 37%; (b) 2-Nitroacetophenone hydrazone, $MnO_2$, 15%; (c) Acetyl chloride, MeOH, 86%; (d) NPE bromide, DIEA, $CH_3CN$, 50° C., 82%; (e) (1) LiOH, MeOH/$H_2O$; (2) 2,3,5,6-Tetrafluorophenol, DMAP, ED-HCl, DMF, 35% for 2 steps; (f) H-Gly-OtBu, EDC-HCl, HOBt, DMF, 91%; (g) (1) $CF_3CO_2H$, $Et_3SiH$, $CH_2Cl_2$; (2) N-hydroxysuccinimide, DMAP, ED-HCl, DMF, 45% for 2 steps.

Figure 22:
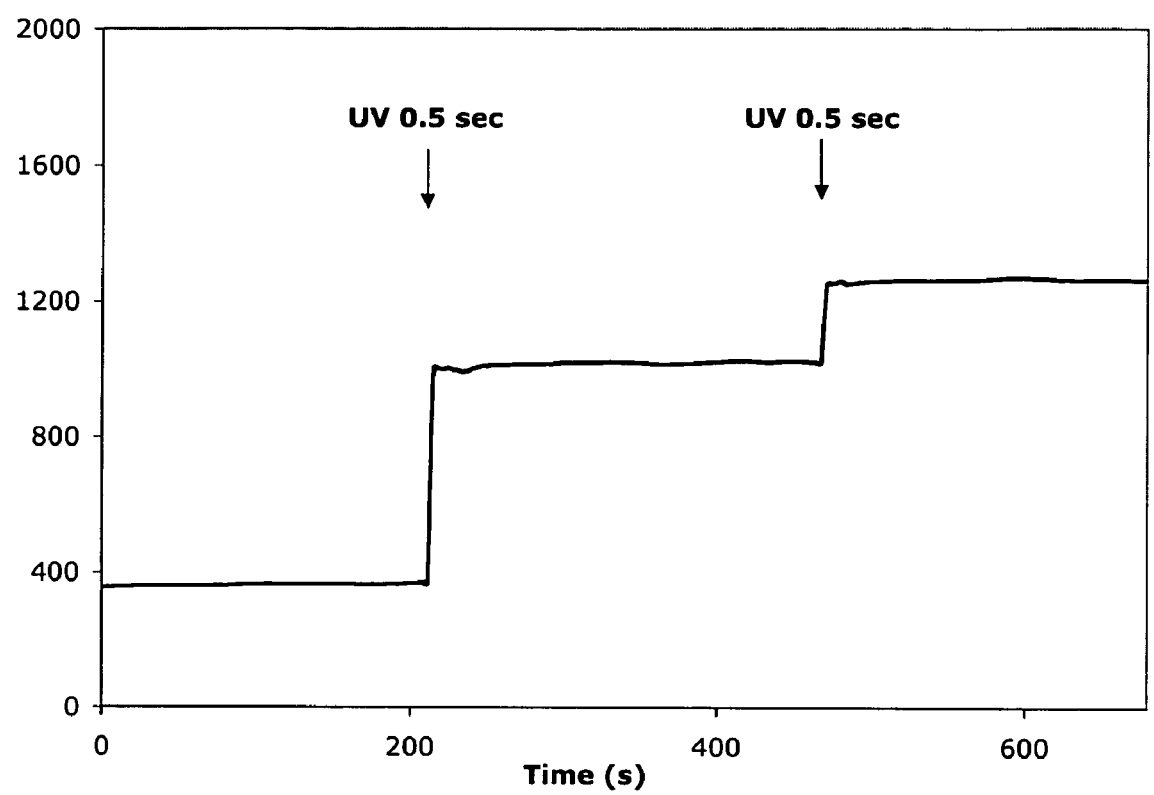

FIG. 22 shows a time course of fluorescence intensity of human fibroblasts loaded with a caged and cell permeable coumarin 16 shown in FIG. 19. Human fibroblasts were loaded with 1 μM of 16 for 30 min in the Hanks Balanced Salt Solution (HBSS, pH 7.35) containing 10 mM Hepes buffer and 5.5 mM glucose. After washing, cells on glass coverslips were imaged on an inverted microscope (Carl Zeiss Axiovert 200). During the imaging, cells were briefly illuminated with WV light (330-380 nm) indicated by the arrows.

DETAILED DESCRIPTION OF PREFERRED EMBODIMENTS

In preferred embodiments, the structure off the caged fluorophore is represented as:

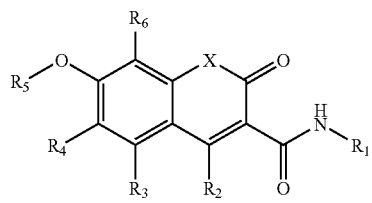

wherein X is O; $R_1$ is any linear or branched alkyl chains up to 20 carbon atoms or any one of the 20 amino acids either in D or L configuration or its derivatives; $R_2$ is H, alkyl groups up to 6 carbon atoms, F, Cl, Br, $CF_3$, $CHF_2$, or $CH_2F$; $R_3$ is H, F, Cl, or Br; $R_4$ and $R_6$ are independently H, F, Cl, or Br; and $R_5$ is a caging group selected from the group consisting of

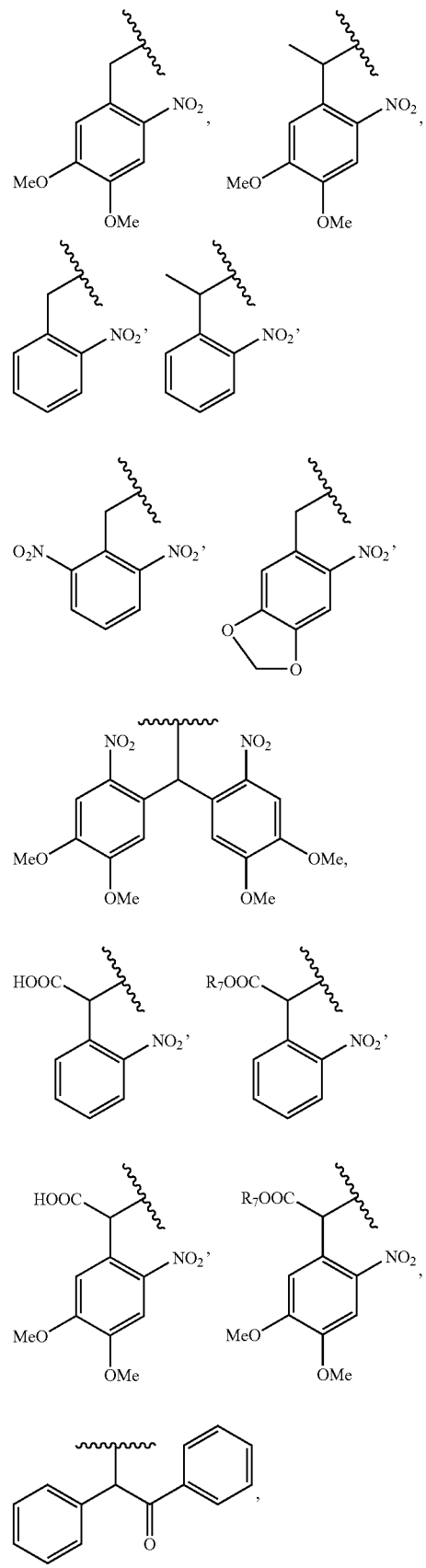

-continued

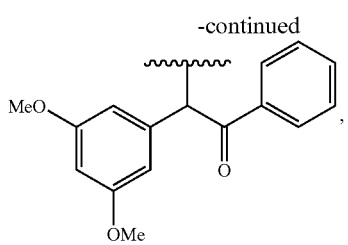

and

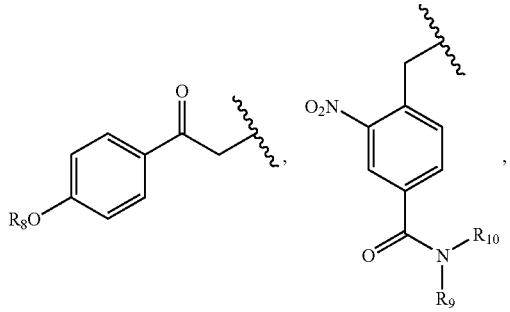

wherein $R_7$ is

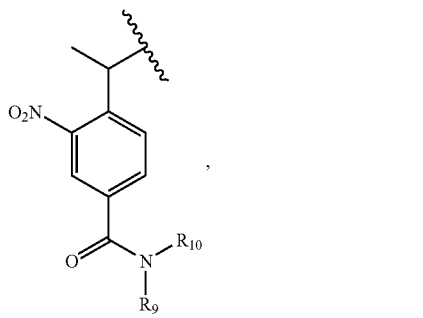

wherein $R_8$ is H, $CH_3$, or $CH_3CO$; and
wherein $R_9$ and $R_{10}$ are independently the same or different and are H, linear or branched alkyl chains containing from 1 to 10 carbons, or acetates.

In additional preferred embodiments, the structure of the caged fluorophores is represented as:

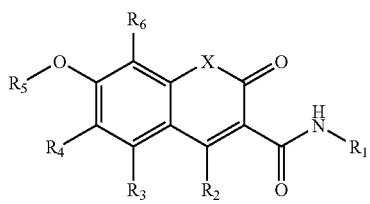

wherein X is N—$R_a$, wherein $R_a$ is H or alkyl chains up to 6 carbons; $R_1$ is any linear or branched alkyl chains up to 20 carbon atoms or any one of the 20 amino acids either in D or L configuration or its derivatives; $R_2$ is H, alkyl groups up to 6 carbon atoms, F, Cl, Br, $CF_3$, $CHF_2$, or $CH_2F$; $R_3$, $R_4$ and $R_6$ are H, F, Cl, or Br; and $R_5$ is a caging group selected from the group consisting of

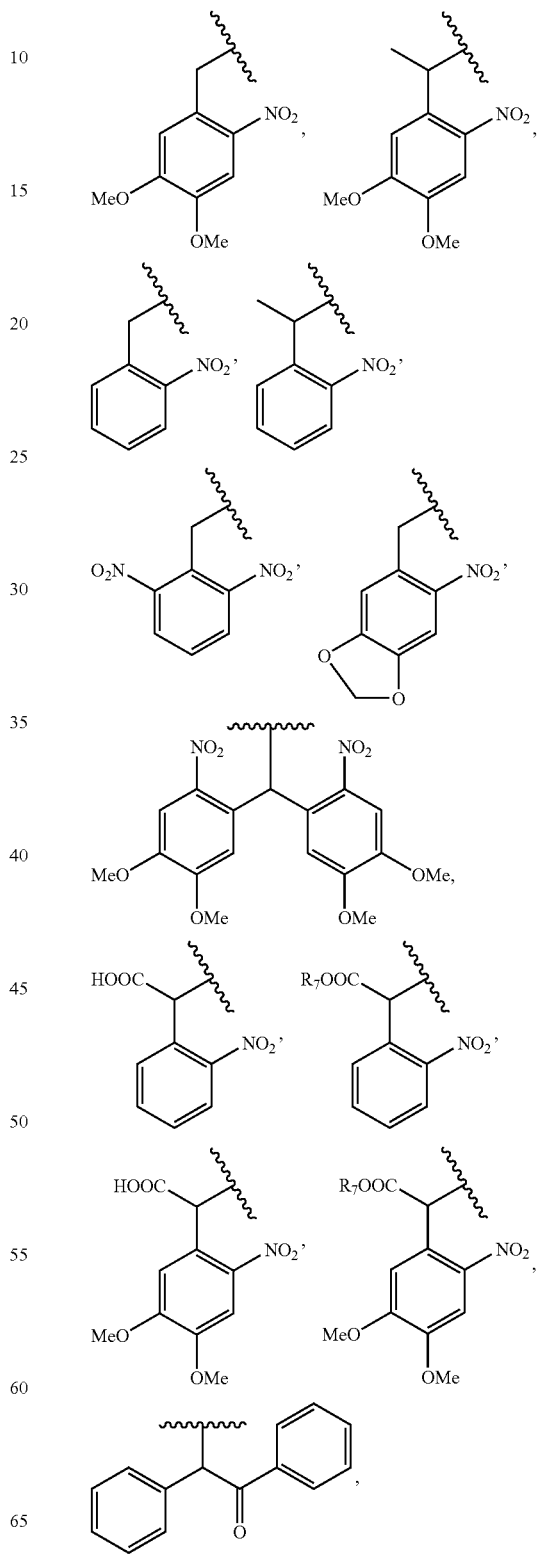

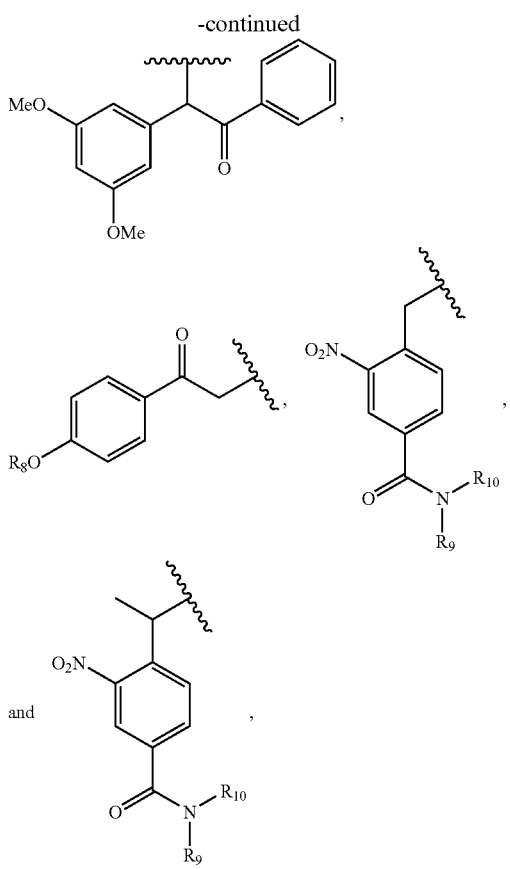

wherein $R_7$ is

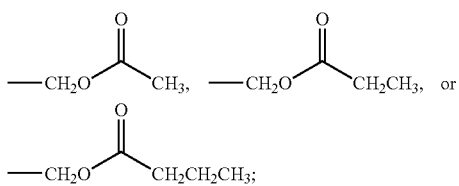

wherein $R_8$ is H, $CH_3$, or $CH_3CO$; and
wherein $R_9$ and $R_{10}$ are independently the same or different and are H, linear or branched alkyl chains containing from 1 to 10 carbons, or acetates.

In additional embodiments, the structure of the caged fluorophore is represented as:

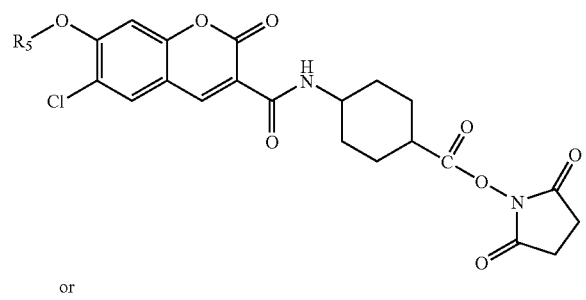

or

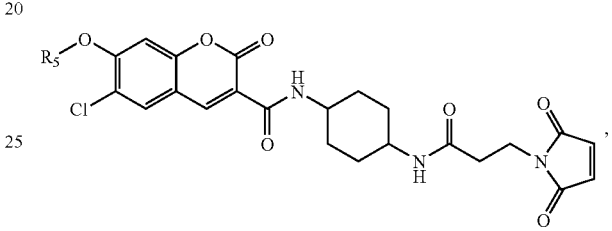

wherein $R_5$ is a caging group defined as it is above. These structures have the N-hydroxysuccinamide ester moiety, which allows conjugation with various biomolecules, such as proteins, antibodies, peptides, DNA, RNA, oligonucleotides, dextrans, or any other molecules containing reactive amino functionalities.

In a further embodiment, the caged fluorophore has the following structure:

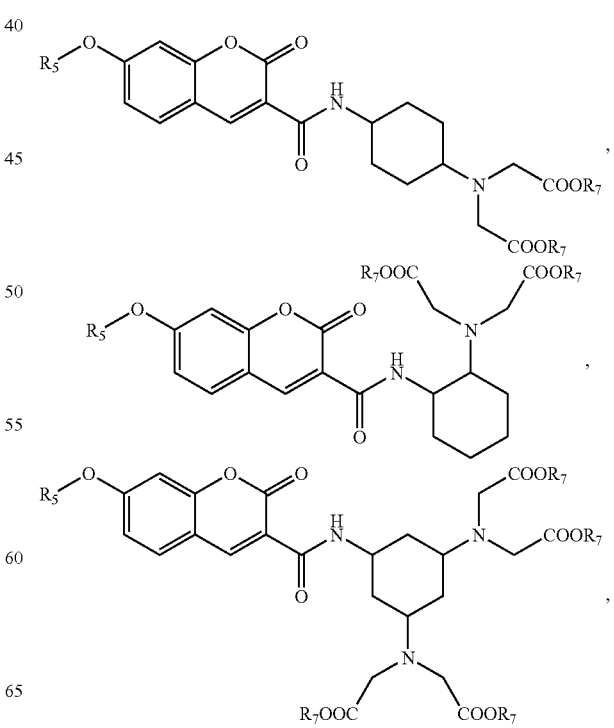

wherein $R_5$ is a caging group defined as it is above. This structures has the maleimide derivative moiety, which allows conjugation with various biomolecules, such as proteins, antibodies, peptides, DNA, RNA, oligonucleotides, dextrans, or any other molecules containing reactive thiol functionalities.

In further embodiments, the caged fluorophore has a structure of:

-continued
or

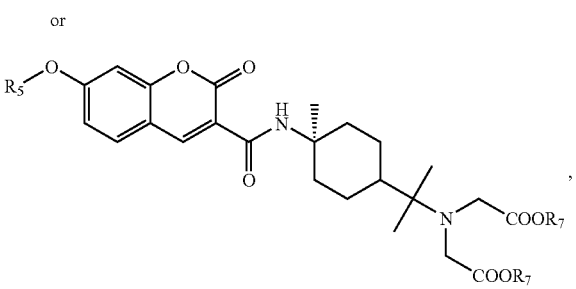

wherein R$_5$ is a caging group defined as it is above, and R$_7$

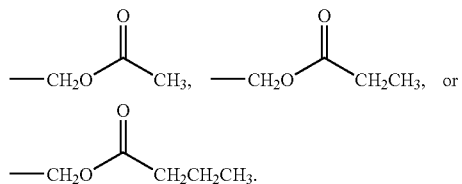

In an additional embodiment, the caged fluorophore has a structure of:

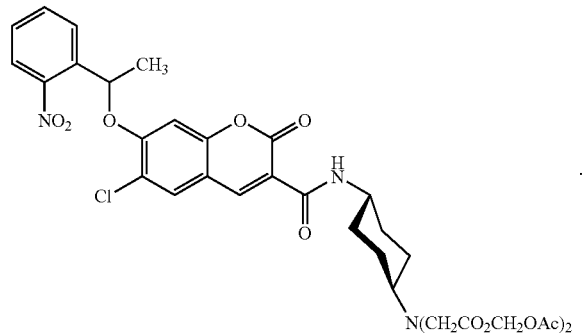

In another preferred embodiment, the structure of the caged fluorophore is represented as:

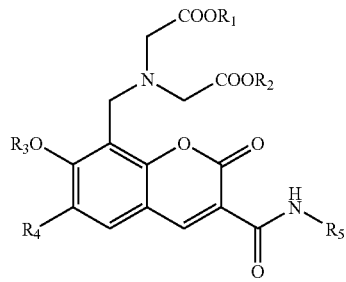

wherein R$_1$ and R$_2$ independently are the same or different and are

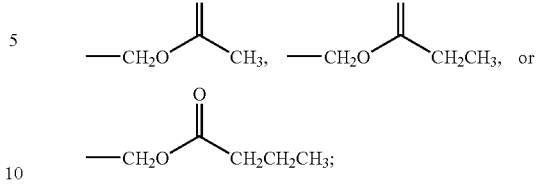

R$_4$ is H, F, or Cl; R$_5$ is a linear or branched alkyl chain containing from 1 to 18 carbons, a D or L amino acid or its derivative, a diamine, a cyclohexane amine, or an adamantanamine derivative; and R$_3$ is a caging group selected from the group consisting of

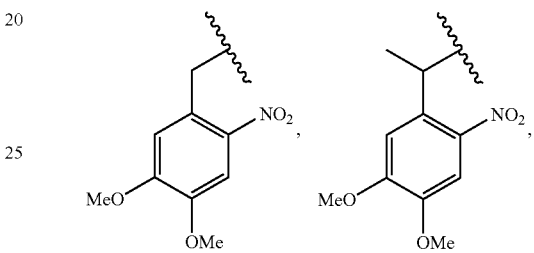

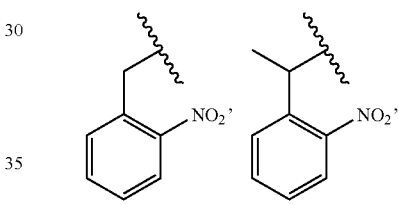

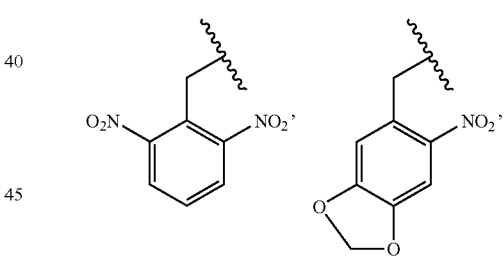

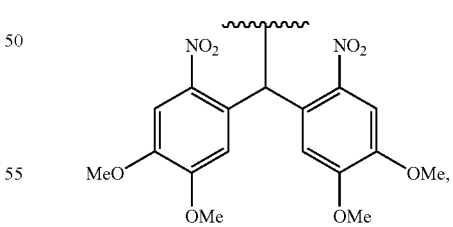

-continued

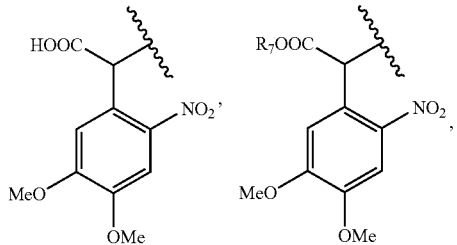

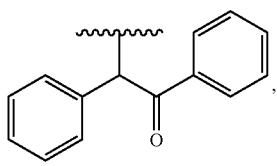

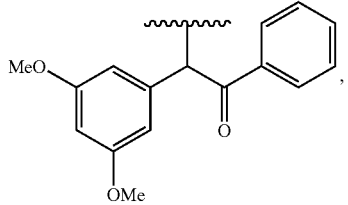

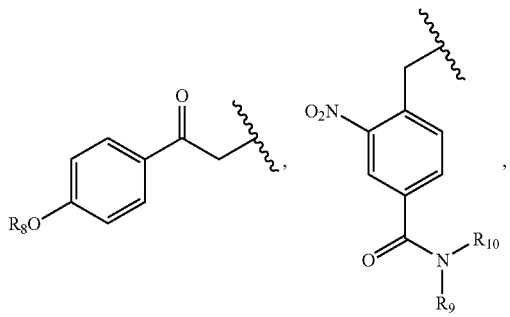

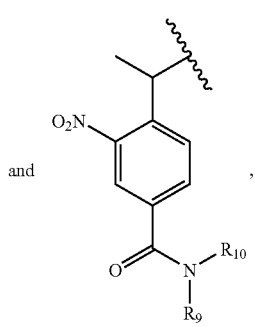

wherein $R_7$ is

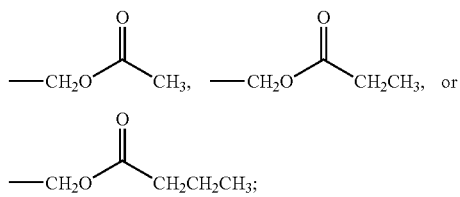

wherein $R_8$ is H, $CH_3$, or $CH_3CO$; and wherein $R_9$ and $R_{10}$ are independently the same or different and are H, linear or branched alkyl chains containing from 1 to 10 carbons, or acetates. A synthesis of some of the above representative compounds are shown in FIG. 18 and FIG. 19.

In additional preferred embodiments, the structure of the caged fluorophore is represented by:

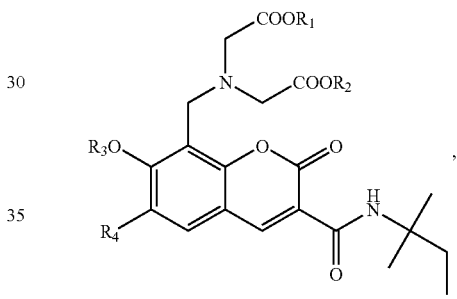

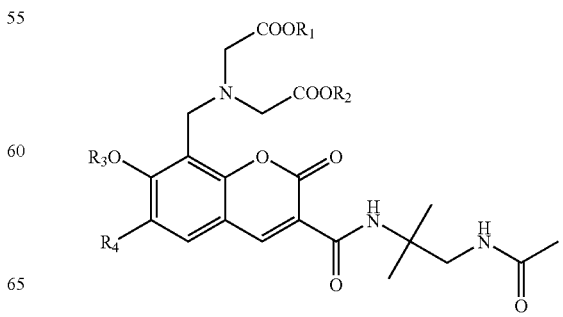

-continued

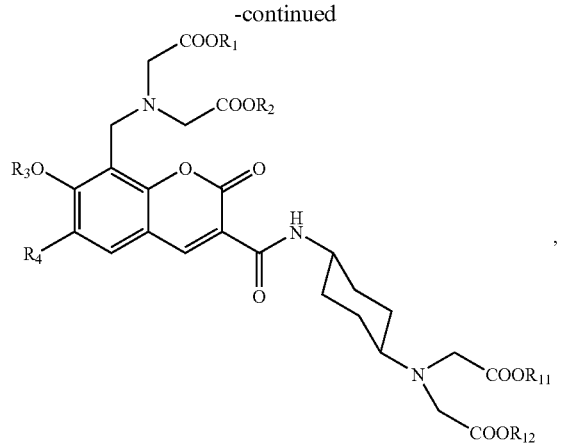

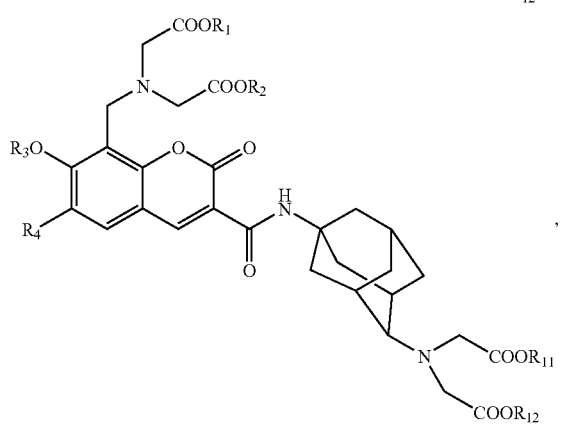

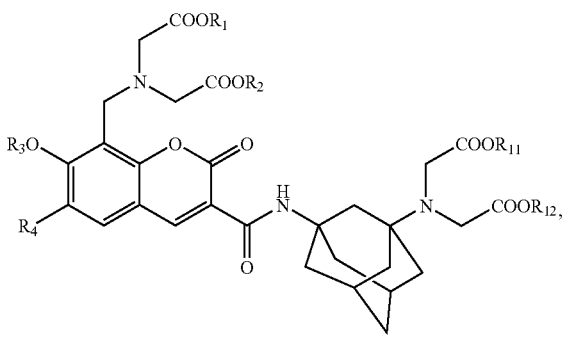

and

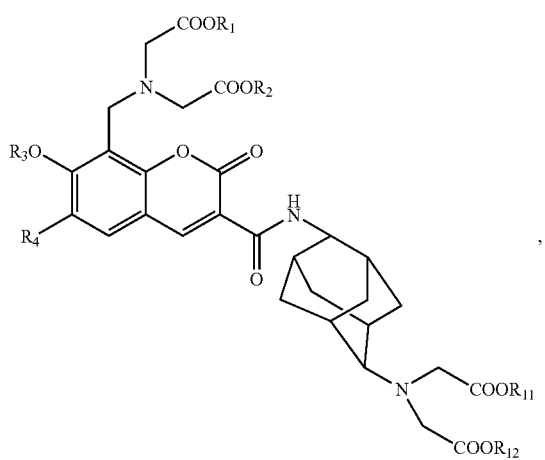

wherein $R_1$, $R_2$, $R_{11}$, and $R_{12}$ independently are the same or different and are

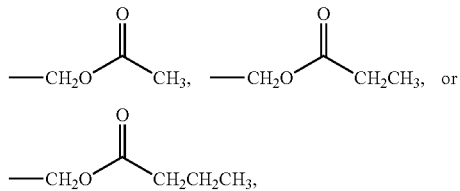

$R_3$ is a caging group defined as it is above, and $R_4$ is H, F, or Cl.

In additional embodiments, the caged fluorophores may be substituted with additional reactive groups to create derivatives which allow conjugation with molecules such as proteins, antibodies, peptides, or any other molecules containing reactive amino or thiol functionalities. In a preferred embodiment, the general structure of a reactive fluorophore derivative for bioconjugation is represented as:

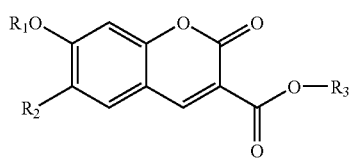

wherein $R_2$ is H, F, or Cl;

$R_3$ is

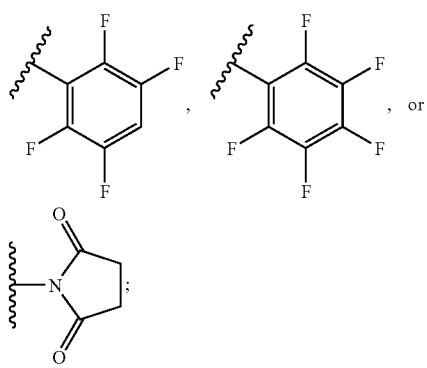

and $R_1$ is a caging group selected from the group consisting of

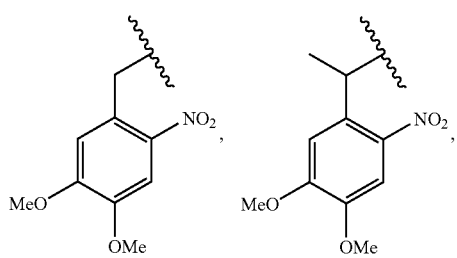

-continued

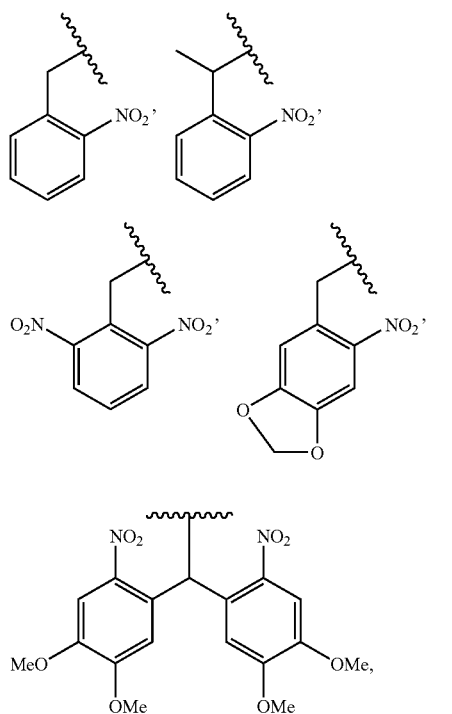

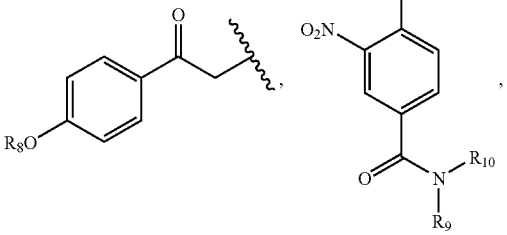

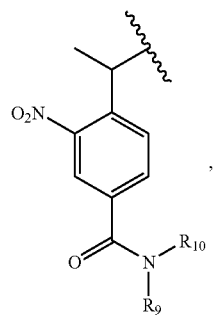

wherein $R_8$ is H, $CH_3$, or $CH_3CO$, and wherein $R_9$ and $R_{10}$ are independently the same or different and are H, linear or branched alkyl chains containing from 1 to 10 carbons, or acetates.

In addition, a spacing group having an optional spacer can be inserted between the 3-carboxylate of coumarin and $R_3$. The spacing group should be an amino acid or its derivative, either natural or synthetic, with an amine function that is used to attach to the 3-carboxylate of coumarin, and an acid function group to create an active ester with an $R_3$ for bioconjugation. A general example of this structure can be represented as

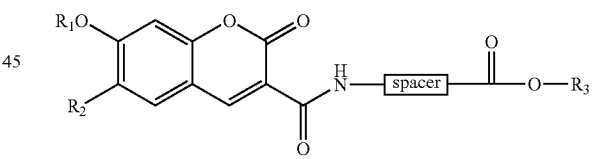

wherein $R_1$, $R_2$, and $R_3$ are defined as they are above for the reactive fluorophore derivative structure. Some examples of amine reactive caged coumarin derivatives for bioconjugations are illustrated in FIGS. 20 and 21.

A number of amino acids can be used as spacing group, including glycine, 2-aminoisobutyric acid, or 4-amino-1-cyclohexanecarboxylic acid. In preferred embodiments, the reactive fluorophore derivatives may have the structure

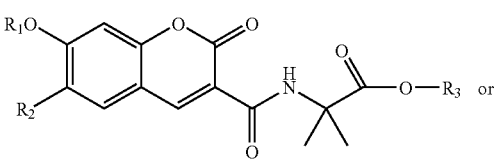 or

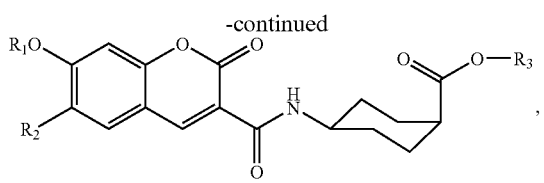

wherein $R_1$, $R_2$, and $R_3$ are defined as they are above for the reactive fluorophore derivative structure.

In further preferred embodiments, thiol reactive caged coumarin derivatives may have the structure

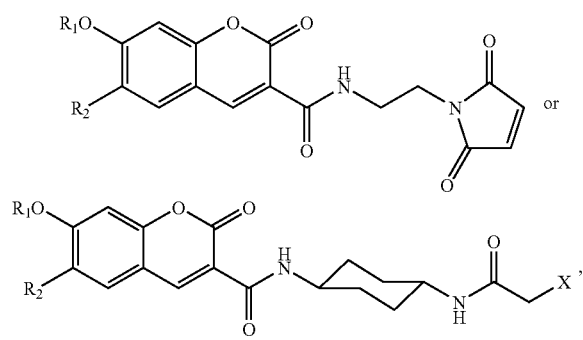

wherein $R_1$, $R_2$, and $R_3$ are defined as they are above for the reactive fluorophore derivative structure and X is Br or I.

The caged fluorophores can be photoactivated by UV light in vitro using a handheld UV lamp and a mechanical shutter for controlling the length of UV illumination. The caged fluorophores can also be activated in live cells with a UV lamp. The UV lamp can be a steady state lamp or a capacitor charged flash lamp. If the cells will be imaged on a fluorescence microscope during the course of photoactivation, the UV light can be delivered through the objective to activate the caged fluorophores. The activation can be done either locally on a few chosen cells by limiting the size of the UV spot, or globally on all cells in the field of view. The caged fluorophores can also be activated by UV light from a laser source which provides UV output. Examples include Argon ion or Krypton ion lasers. Laser activations can be done in vitro or in vivo and offer the advantage of more precise temporal gating.

Photoactivation through two-photon excitation can be accomplished using infrared light to excite the sample, which avoids the risk of UV damage. Infrared light is at a much longer wavelength than UV light, so it is less energetic, but it also penetrates deeper into tissue.

Two photon uncaging was carried out using a method similar to the published (Furuta, T.; Wang, S. S.; Dantzker, J. L.; Dore, T. M.; Bybee, W. J.; Callaway, E. M.; Denk, W.; Tsien, R. Y. *Proc. Natl. Acad. Sci. U.S.A.* 1999,96, 1193-200; and Fedoryak, O. D.; Dore, T. M. *Org Lett* 2002, 4, 3419-22.) Light from a fs-pulsed and mode-locked Ti:Sapphire laser (Mira 900 pumped by a Verdi, Coherent, Santa Clara, Calif.) was focused (25 mm focal length lens, 01 LPX 029/077, Melles-Griot, Irvine, Calif.) into the center of the a microcuvette (10×3×3 mm illuminated dimensions, Hellma 105.251-QS). The cuvette chamber was filled with 45 µl of 100 µM of compound 2a (FIG. 3) in 100 mM Mops buffer (pH 7.3, 5% DMSO, 3% EtOH). The sample was illuminated for 20 min at room temperature with fs-pulsed and mode-locked laser light at 600 mW. The amount of coumarin released was measured by the fluorescence emission after diluting the sample 10 times with 20 mM Mops buffer (Ex 425 nm, Em 450 nm). The experiment showed that the optimal 2 photon uncaging wavelength for compound 2a is 740 nm.

| | Wavelengths of mode locked infra laser | | | |
|---|---|---|---|---|
| | 720 nm | 740 nm | 760 nm | 780 nm |
| Relative fluorescence intensity after 2 photon uncaging | 16.5 | 27.5 | 20 | 7.0 |

The caged fluorophores can be used in various cellular imaging applications. Because the caged fluorophores are cell permeable and do not require an invasive injection technique, they may be used to study cellular gap junction communications without disrupting other molecular concentrations. Localized uncaging of the fluorophores allows selective labeling of cells within a population, or selective labeling of one cell in a coupled cell pair. Fluorescent imaging and data analysis allows the quantitative calculation of the molecular transfer rates across the gap junctions of coupled cells. Thus, the caged fluorophores enable the study of dynamic intercellular communication in cell populations and between gap junctions. Also, because the caged fluorophores derived from coumarin emit blue light, they spectrally complement other fluorophores emitting at green or red regions. Thus, they may be used in combination with other fluorescent dyes or sensors to carry out photo-uncaging and multi-color imaging simultaneously in live cells.

EXAMPLE 1

General Synthesis

6-Chloro-7-hydroxy-coumarin 3-carboxylate was prepared in two steps starting with 4-chloro-resorcinol. Coupling coumarin 3-carboxylate with the methyl ester of D-glutamate provided coumarin 3-carboxamide (1a, FIG. 3). The dye absorbs maximally at 408 nm with an extinction coefficient of 44,000. The fluorescent quantum yield of the molecule is 0.93 measured in an aqueous buffer (100 mM KCl, 20 mM Mops, pH 7.35). Three caged derivatives of this fluorophore were synthesized by masking the 7-hydroxyl group of coumarin with the following caging groups: 1-(2-nitrophenyl)ethyl ("NPE," 2a, FIG. 3), 2-nitrobenzyl ("NB," 2b, FIG. 3), and 4,5-dimethoxy-2-nitrobenzyl ("DMNB," 2c, FIG. 3).

EXAMPLE 2

Photoactivation and Excitation

The three caged coumarins prepared in Example 1 (2a, 2b, 2c, FIG. 3) were dissolved in aqueous buffer (pH 7.35) containing 100 mM KCl and 20 mM Mops to final concentrations of 2 µM. The solutions were photolyzed with 365 nm light from a filtered mercury lamp. Fluorescence emission spectra at 408 nm of the solutions were taken with a Fluorolog spectrometer (Jobin-Yvon) after different UV exposures. FIG. 4 shows the spectra of NPE-caged coumarin (2a, FIG. 3).

Figure 5:
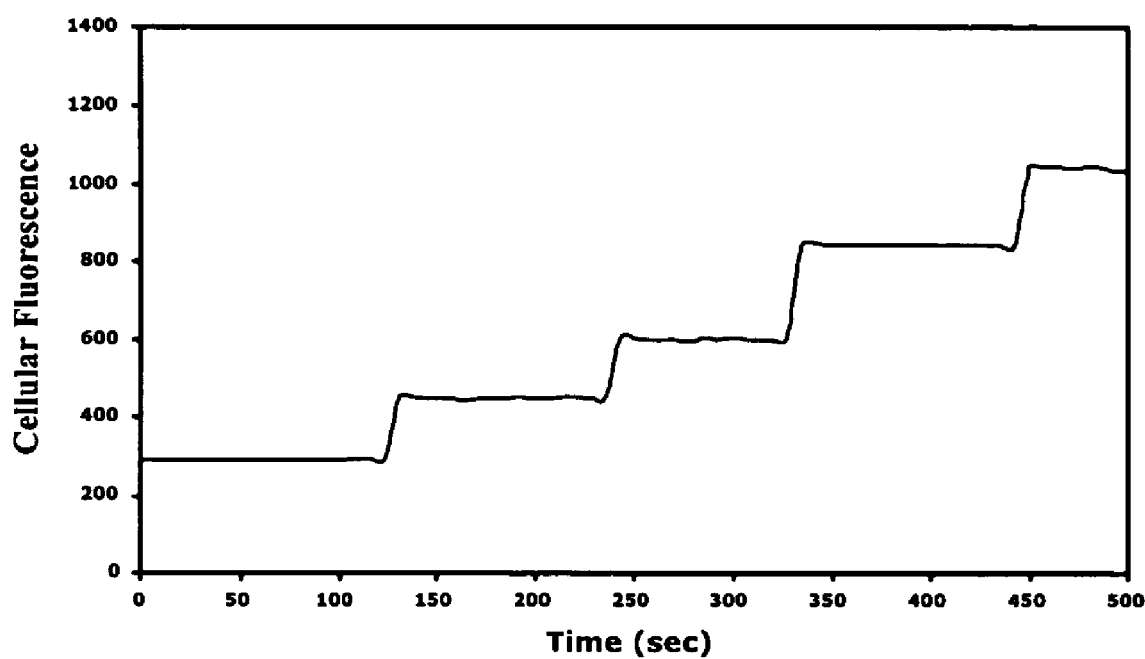
FIG. 5 shows the cellular fluorescence intensities of cells loaded with a caged and cell permeable coumarin. The step-wise increases in fluorescence were created by UV photolysis.

All three caged fluorophores prepared in Example 1 are essentially non-fluorescent, as shown by their negligible fluorescence quantum yields in Table 2 below. UV illumination (365 nm) removed the caging group and progressively generated highly fluorescent coumarin 1a, as shown in FIG. 5. The fluorescence enhancements after uncaging ranged from 200 times (2b) to nearly 800 times (2c). This robust change in fluorescence quantum yields is important for generating high contrast optical signals with a minimum background. The quantum yields of photolysis, which are determined by the ferrioxalate actinometry (Li et al., Nature, vol. 392, pp. 936-41 (1998).) and the uncaging cross sections of the three caged fluorophores were measured and are shown in Table 2. There are remarkable differences in the uncaging cross sections among three caged coumarins. The uncaging cross section of NPE caged coumarin (2a) exceeded 6000, about two orders of magnitude higher than a previously reported NB-caged fluorescein monoether ($Q_u\epsilon$=76 at 350 mn) (Krafft, et al., 1998). The NB-caged coumarin (2b) has an uncaging cross section significantly lower than that of compound 2a, but is 6 times higher than that of the DMNB caged coumarin (2c) or nearly an order of magnitude higher than that of the fluorescein cage.

wavelengths. This suggests that the photonic energy absorbed by the coumarin moiety was utilized to photolyze caging groups very efficiently, particularly for the NPE cage (2a) with $Q^u$ of 33%.

EXAMPLE 3

Esterification

Protection of the two carboxylates of the D-glutamate moiety with acetoxymethyl ("AM") ester groups is useful for cellular imaging applications. AM esters are stable in physiological solutions but are susceptible to enzymatic hydrolysis by cellular esterases. The enzyme hydrolysis regenerates negatively charged species which cannot diffuse out of cells (Grynkiewicz, et al., 1985). This irreversible trapping process has been applied to enrich various ion indicators, fluorescent probes, and second messengers into cells to higher concentrations (Li, et al., 1998). With the current caged coumarin derivatives, hydrolysis of two

TABLE 2

Fluorescent and Photo-Chemical Properties of Caged Coumarins

| Caged Coumarins | 2a<br>R = (O$_2$N-phenyl-CH(CH$_3$)-) | 2b<br>R = (O$_2$N-phenyl-CH$_2$-) | 2c<br>R = (O$_2$N, (OMe)$_2$-phenyl-CH$_2$-) |
|---|---|---|---|
| $Q_{f2}$ | 0.0025 | 0.0048 | 0.0012 |
| $Q_{f1}/Q_{f2}$ | 372 | 194 | 775 |
| $Q_u$ | 0.33 ± 0.003 | 0.04 ± 0.004 | 0.0036 ± 0.0005 |
| $\epsilon$ | 20,000 | 14,000 | 26,000 |
| $Q_u\epsilon$ | 6600 | 560 | 94 |

In Table 2, $Q_{f2}$ is the fluorescence quantum yield of caged coumarins 2a-2c; $Q_{f1}/Q_{f2}$ is the multiples of fluorescence enhancement after photo-converting 2a-2c to 1a; $Q_u$ is the quantum yield of uncaging at 365 nm, determined from the equation $Q_u=(I\sigma t_{90\%})^{-1}$, where I is the irradiation intensity from a mercury arc lamp equipped with a filter allowing 365 nm output, measured by the potassium ferrioxalate actinometry, $\sigma$ is the decadic extinction coefficient (cm$^2$mol$^{-1}$) of caged coumarins at 365 nm; and $t_{90\%}$ is the irradiation time in seconds for 90% conversion to the product 1a, measured by quantifying the fluorescence intensity of the generated 1a from caged forms (2 µM of 2a, 2b, or 2c in 100 mM KCl, 20 mM Mops, pH 7.35) after various doses of UV illuminations; $\epsilon$ is the extinction coefficient (M$^{-1}$cm$^{-1}$) of caged coumarins measured at 365 nm; and $Q_u\epsilon$ is the uncaging cross section at 365 nm (M$^{-1}$cm$^{-1}$) which measures the sensitivity of caged compounds to UV photolysis.

The very high uncaging cross sections of 2a and 2b mainly resulted from increased UV absorption. The extinction coefficients of the NB and NPE groups by themselves are less than 400 M$^{-1}$cm$^{-1}$ above 360 nm. The theoretical maximum limits of their uncaging cross sections should be no more than 400 M$^{-1}$cm$^{-1}$ above 360 nm even when $Q_u$ approaches unity. When these caging groups are attached to the 7-hydroxyl group of coumarin, the overall absorption of the molecule increased by more than 50 times at UV methyl esters of compound 2a under a number of conditions was accompanied by the concomitant hydrolysis of the amide bond of coumarin 3-carboaximide. Thus, protecting two carboxylates of glutamate with t-butyl groups is a more feasible synthetic route. Acid treatments of the intermediate 2d (prepared from 1b, FIG. 3) followed by esterification with AM bromide afforded a caged and cell permeable coumarin derivative 3.

EXAMPLE 4

Imaging of Hela Cells

Hela cells were loaded with 2 µM of compound 3 (FIG. 3) for 1 hour in the Hanks Balanced Salt Solution ("HBSS," pH 7.35) containing 10 mM Hepes buffer and 5.5 mM glucose. After washing, cells on glass coverslips were imaged on an inverted microscope (Carl Zeiss Axiovert 200). Fluorescent imaging of cells loaded with compound 3 prior to uncaging showed that there was no difference in fluorescence intensity of loaded cells from control cells, indicating that the background fluorescence of caged coumarin in cells is negligible. Subsequent UV photolysis generated a sudden jump of cellular blue fluorescence. The loaded coumarin was excited with light passing through an interference filter (440AF21, Omega Optical). During UV uncaging, cells were briefly illuminated with UV light from a bandpass filter at 330-380 nm, indicated by each stepwise increase in fluorescence shown in FIG. 5. FIG. 5 shows the average fluorescence intensity of cells in the field of view over the course of 4 episodes of UV photolysis. The first two stepwise increases denote 0.1 sec UV exposures, and last two stepwise increases represent 0.2 sec UV exposures.

EXAMPLE 5

Measuring Kinetics of Molecular Transfer through Gap Junctions

Figure 6:
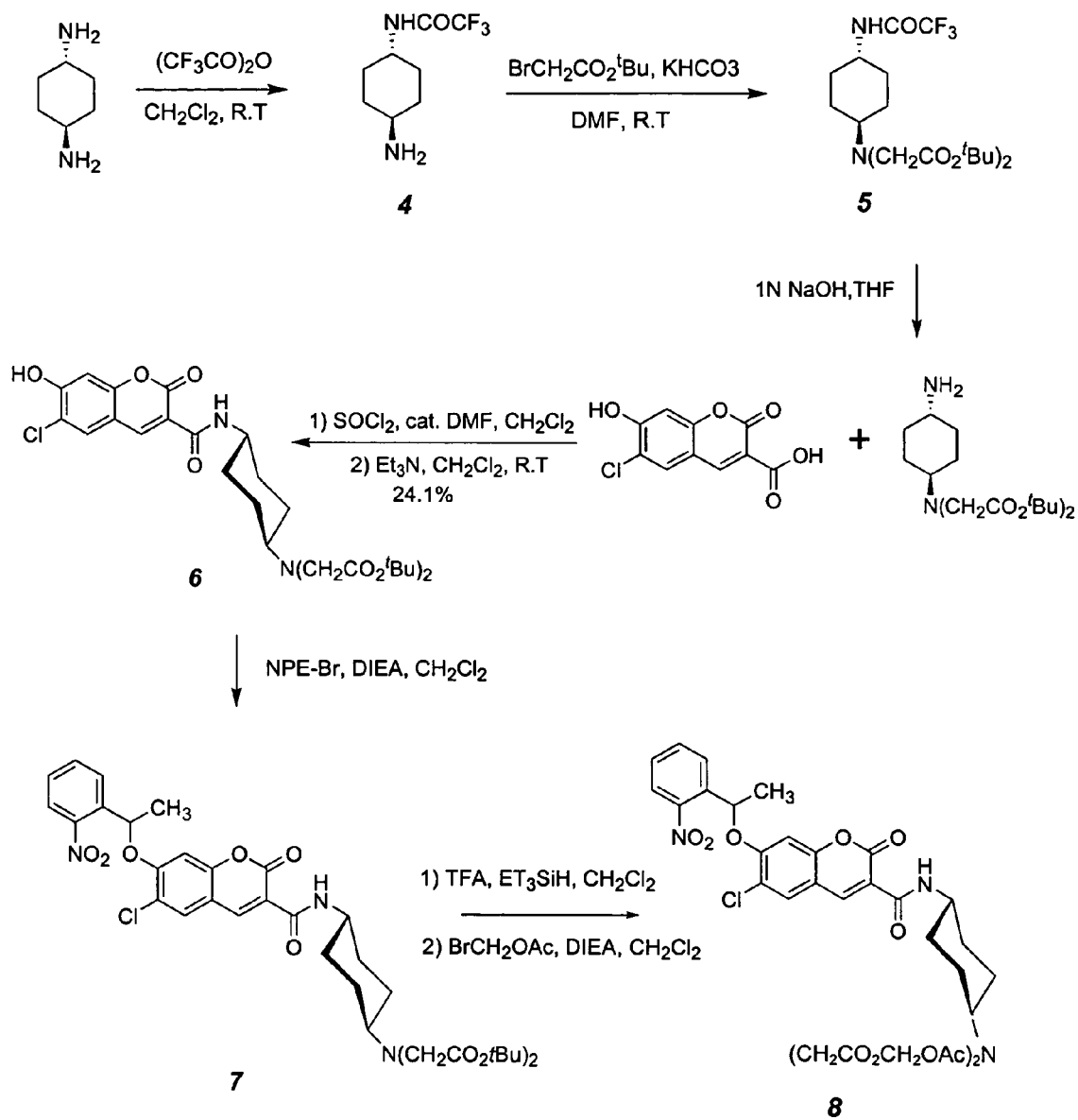
FIG. 6 is a reaction scheme showing the synthesis of a caged fluorophore NPE-HCCC2/AM shown in FIG. 1 based on 6-chloro-7-hydroxy-coumarin 3-carboxamide.

A caged coumarin, designated compound 8, was synthesized according to the scheme illustrated in FIG. 6. This compound was used to measure molecular transfer rates in cultured human fibroblasts. In order to follow molecular transfer through gap junctions, the technique of localized uncaging was used to optically mark one cell among a group of coupled cells. To achieve localized photolysis in the chosen cell, a field diaphram in the epifluorescence excitation light path was used. Before uncaging, all cells in the field of view were monitored. By closing the iris of the diaphram to a minimum, the size of the excitation beam was reduced to a fraction of a cell. At this time, UV light was delivered to a chosen cell within a coupled cell pair, which were designated cells 1 and 2. A UV pulse was delivered to cell 1 at about 400 sec and to cell 2 at about 1600 sec. This locally photolyzed compound 8 and generated an asymmetric marking in the coupled cell pair. The iris of the field diaphragm was then opened to the maximum to monitor all cells, including an isolated control cell, designated cell 3. Dye transfer from the photolyzed cell (or donor cell) to the recipient cell was followed with fluorescence imaging.

A fluorescence imaging system suitable for high speed multi-color imaging and photo-uncaging experiments was used. The imaging set-up consisted of the following major components: an inverted microscope (Axiovert 200, Carl Zeiss), an excitation light source with a 175 W Xenon lamp (Lambda DG-4, Sutter Instrument), and a cooled CCD camera (ORCA-ER, Hamamatsu). Lambda DG-4 employs two scanning galvanometers to realize a rapid wavelength switching within a time resolution of less than 2 msec. It has 4 positions for housing band-path filters. The image acquisition and wavelength switching were controlled by in integrated imaging software (Openlab, Improvision).

Figure 7:
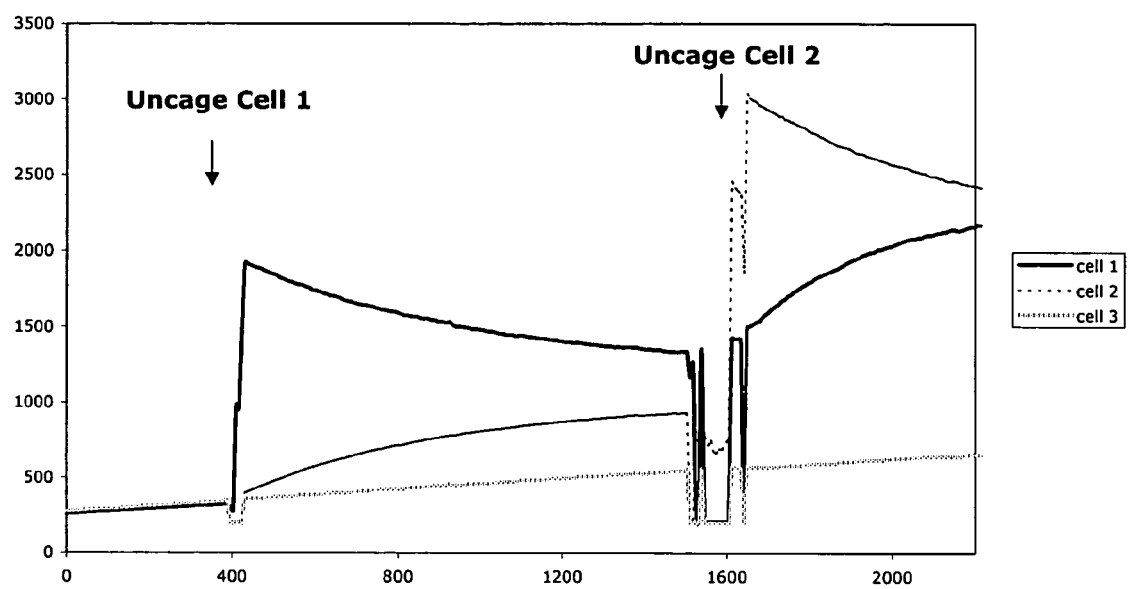
FIG. 7 shows the fluorescence intensities of a coupled cell pair (cells 1 and 2) loaded with a caged coumarin and subject to localized uncaging at two different times, as well as an isolated control cell (cell 3).

FIG. 7 shows a plot of the fluorescence intensities of cells 1, 2 (a coupled cell pair) and 3 (an isolated cell as control) against time. These fluorescence intensities can be used to calculate the dye transfer rates through the gap junctions of the coupled cells. Quantitative analysis of dye transfer rates through gap junctions can be carried out using the same approach developed for the FRAP method (Wade, et al., 1986; Peters, 1983). Because small molecules diffuse much more rapidly in the cytosol than across gap junctions, the rate-limiting step for intercellular dye passage is generally considered to be gap junction permeation (Deleze, et al., 2001; Loewenstein, 1979). The kinetics of dye passage is expected to follow the equation:

$$(C_e-C_t)/(C_e-C_0)=e^{-kt}$$

where $C_e$, $C_0$, and $C_t$ are dye concentrations in the recipient cell at equilibrium, zero time and time t, respectively. The rate constant k (in units of $sec^{-1}$) describes the relative permeability in the coupled cell pairs, and is sufficient for studying regulations of gap junction permeability (Pj) in the same coupled cell pairs if the cell volume (V) and gap junction surface area (A) remain relatively constant in the course of an experiment. When using k to compare the gap junction permeability ($P_j$) of different pairs of coupled cells, variations in the cell volume and the gap junction surface area (or number of connexin channels) must be evaluated, because $P_j$ is related to k by the equation $k=P_j A/V$. This is not an easy task because both V and A are difficult to determine. One of the major advantages of using coupled cell pairs to study the gating of connexin channels is to minimize uncertainties caused by these hard-to-calibrate variables.

Assuming the fluorescence signal measured in the microscope under constant experimental conditions is proportional to dye concentrations, the above equation can be written as:

$$(F_e-F_t)/(F_e-F_0)=e^{-kt} \text{ or } \ln((F_e-F_t)/(F_e-F_0))=-kt$$

where $F_e$, $F_0$, and $F_t$ are cellular coumarin fluorescence intensities at equilibrium, zero time and time t, obtained by subtracting the measured cellular fluorescence from the background signal. Images were obtained once every 10 to 15 seconds. This acquisition frequency is sufficient for following the kinetics of dye transfer between cells. More frequent acquisitions (e.g., one image every 2 to 5 seconds) can cause some uncaging. This undesirable photolysis artificially increases the rate of fluorescence intensity in the cells, thus affecting the quantification of dye transfer. This problem of "auto-uncaging" during image acquisitions can be easily corrected by measuring the slope of fluorescence increase prior to UV photolysis. Subtraction of the "auto-uncaging" rate from the cells of interest gives accurate measurements.

Figure 8:
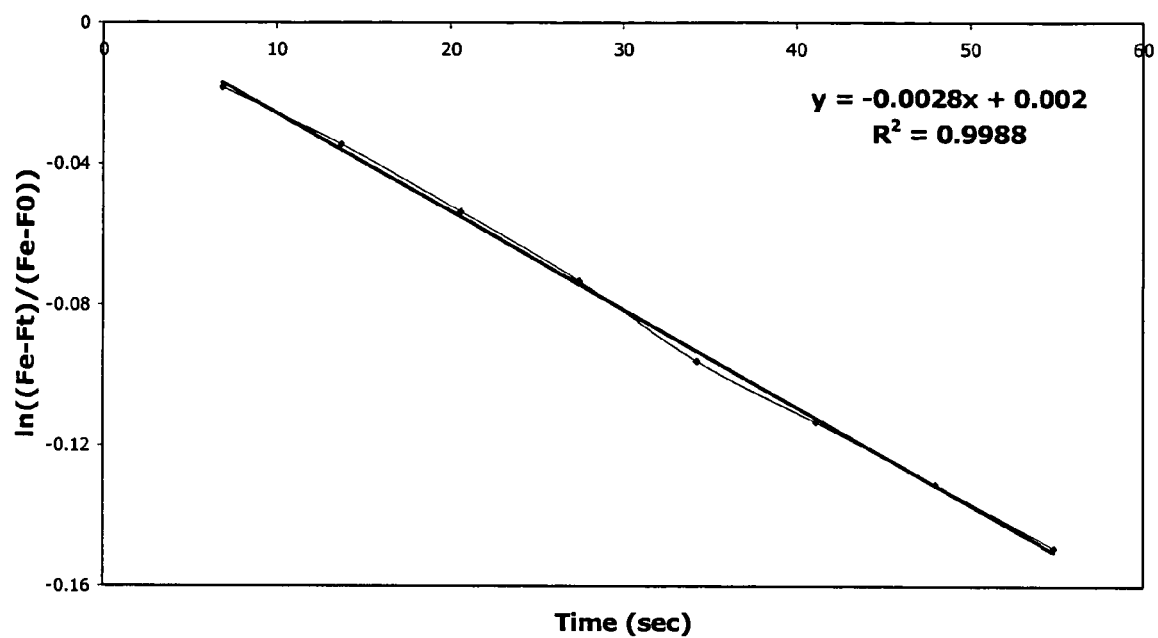
FIG. 8 shows the dye transfer rate from cell 1 to cell 2 analyzed by Fick's equation.
Figure 9:
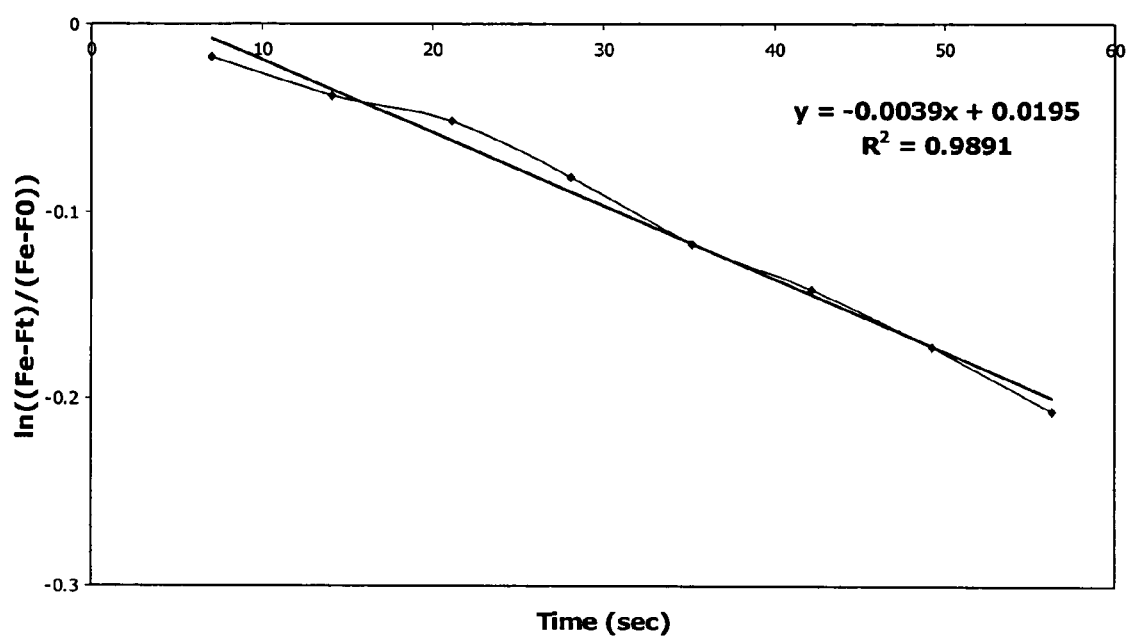
FIG. 9 shows the dye transfer rate from cell 2 to cell 1 analyzed by Fick's equation.

FIGS. 8 and 9 show the dye transfer rates to cell 2 and cell 1 respectively. The data were extracted from the first (FIG. 8) and second (FIG. 9) local uncagings of coumarin in coupled cells 1 and 2.

EXAMPLE 6

Measuring Inhibition of Molecular Transfer through Gap Junctions

Figure 10:
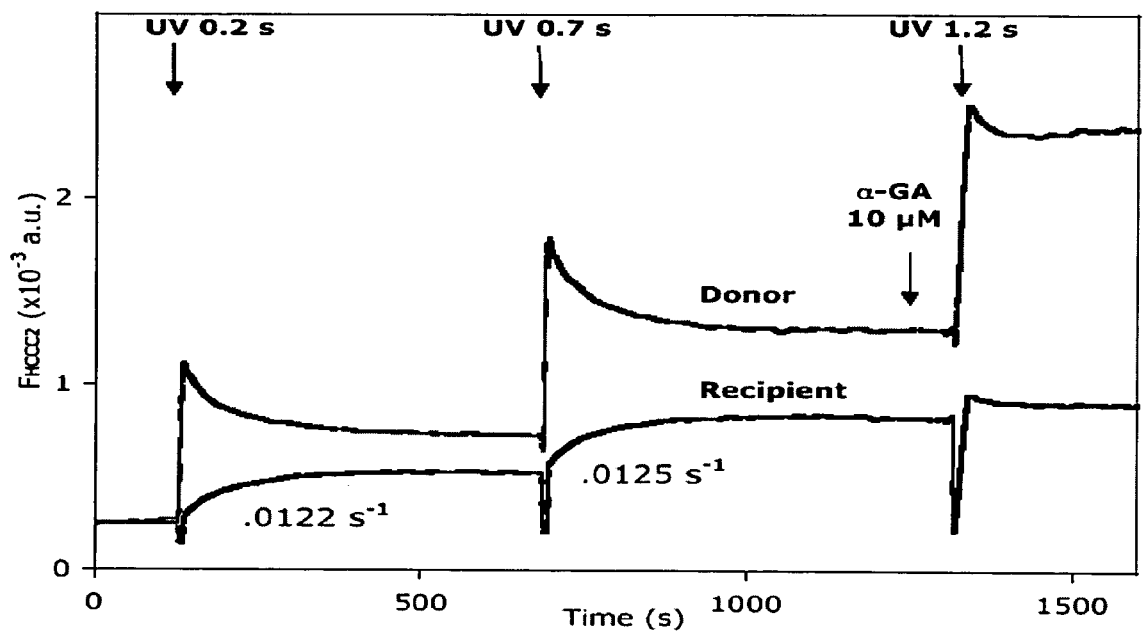
FIG. 10 shows the fluorescence intensities of a coupled cell pair loaded with a caged coumarin and subject to localized uncaging and treatment with an inhibitor of junctional coumarin transfer ($\alpha$-glycyrrhetinic acid).

Coupled human fibroblast cells were loaded with NPE-HCCC2-AM (1 µM) for 40 minutes in Hanks Balanced Saline (HBS with 10 mM Hepes, 5.5 mM glucose, pH 7.3), then washed and incubated for another 15 minutes before imaging on an inverted fluorescence microscope. The time course of fluorescent intensities of HCCC2 after it was locally uncaged in the "donor" cells is shown in FIG. 10 ($F_{HCCC2}$, arbitrary units, 425±5 nm excitation, 460±10 nm emission). A field diaphragm was placed in the excitation light path inside the microscope. The iris of the field diaphragm was reduced to a minimum to limit the area of UV illumination (360±20 nm) to a fraction of a cell during localized uncagings. Digital fluorescence images were taken every 15 seconds. The rates of HCCC2 diffusion are indicated under each episode of transfer. α-Glycyrrhetinic ("αG") was added to the cells prior to the third uncaging. αG is a classical inhibitor of gap junction transfers (Rozental, et al., 2001). FIG. 10 shows that the coumarin transfer in human fibroblasts is susceptible to inhibition by αG. After addition of αG, the recipient cell failed to show a increase in the rate of coumarin transfer.

EXAMPLE 7

Figure 11:
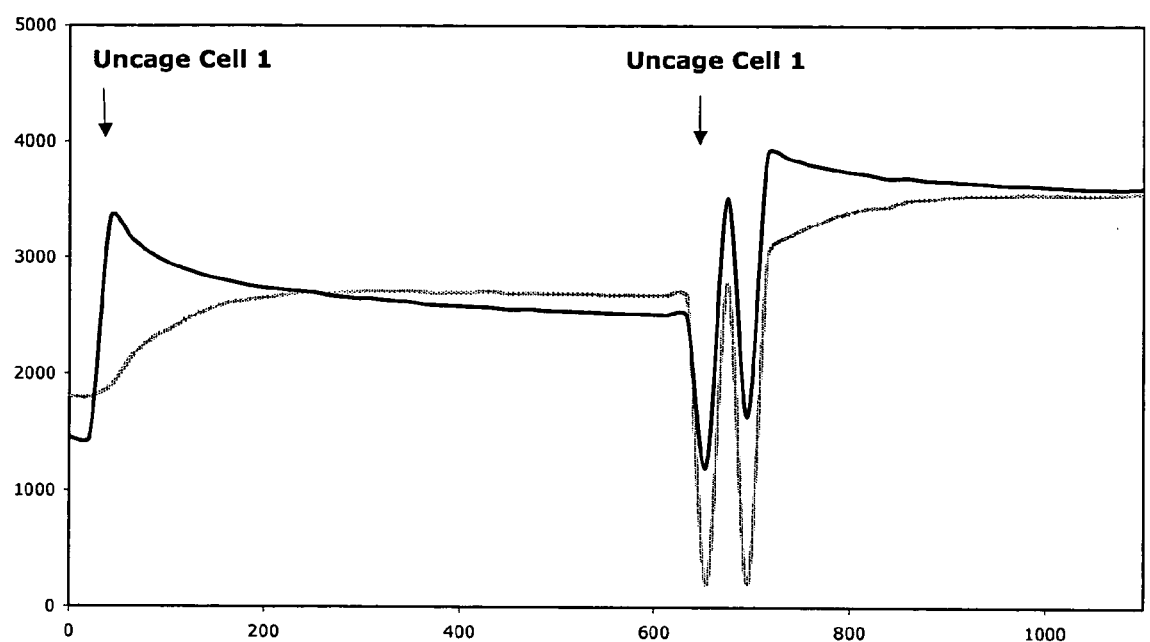
FIG. 11 shows the fluorescence intensities of a coupled pair of Hela cells which express connexin and which are loaded with caged coumarin and subject to localized uncaging.
Figure 12:
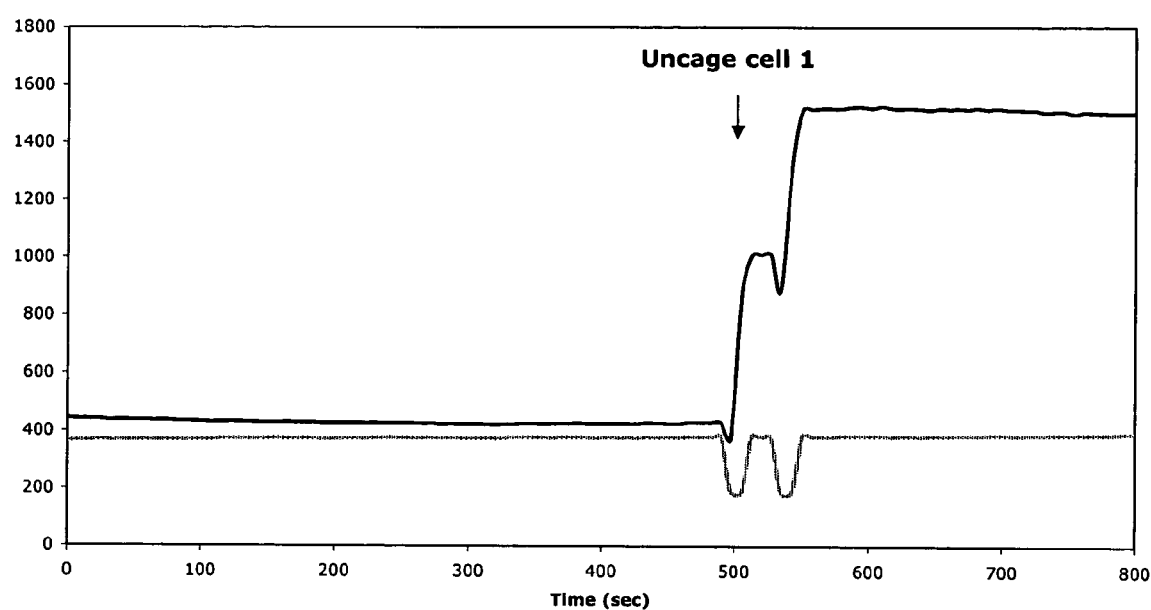
FIG. 12 shows the fluorescence intensities of Hela cells in contact with each other which do not express connexin and which are loaded with caged coumarin and subject to localized uncaging. No intercellular coumarin transfer in untransfected Hela cells.

Imaging to Show Connexin is Necessary for Molecular Transfer through Gap Junctions Measuring the fluorescence intensity of uncaged coumarins demonstrates that the junctional protein connexin is required for intercellular coumarin transfer. Intercellular coumarin transfer was only observed in Hela cells transfected with junctional protein connexin 43, as shown in FIG. 11. It was not observed in the wild type Hela cells that do not express junctional connexins, as shown in FIG. 12.

EXAMPLE 8

Simultaneous Imaging of Coumarin and Fluo-3 Fluorescence in Cells

Human fibroblasts were loaded with the calcium indicator Fluo-3/AM (Molecular Probes), and a caged and cell permeable coumarin derivative (compound 8, FIG. 6). After loading, cells were washed with HBS buffer and imaged similarly as in Example 4. Optical filters were used (coumarin excitation, 440AF21 (Omega Optical); Fluo-3 excitation, 490/20; UV uncaging 330WB80; dichroic, 61010bs; emission filter, 84101 special; all of Chroma Technology unless stated otherwise).

Figure 13:
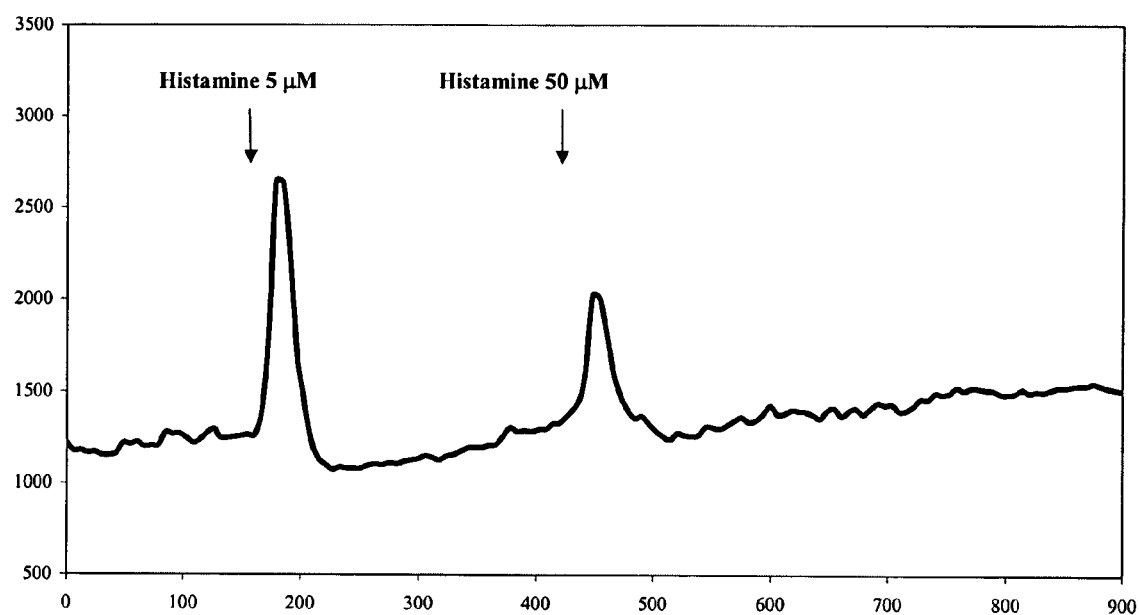
FIG. 13 shows the fluorescence of calcium indicator Fluo-3 in a cell with histamine introduced.
Figure 14:
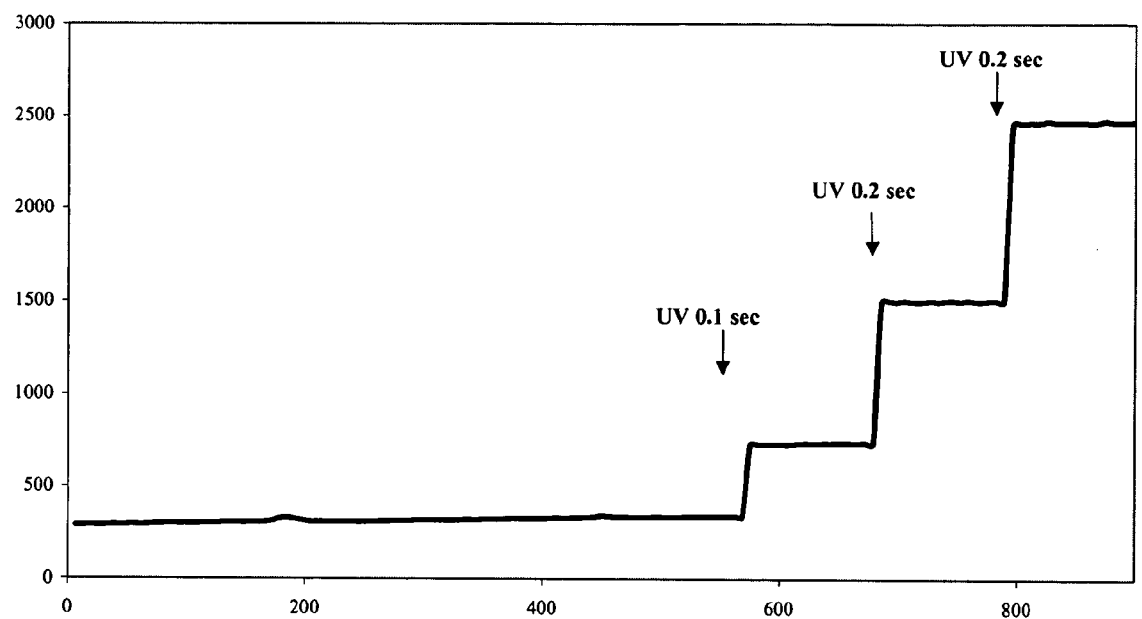
FIG. 14 shows the concurrent measurement of fluorescence of uncaged coumarin in the same cell shown in FIG. 13.

The fluorescence of a representative cell is shown in FIGS. 13 and 14. Fluo-3 measures cell calcium concentrations. Addition of histamine, a cell surface receptor agonist, induced intracellular calcium increase. This increase was detected in the Fluo-3 channel (FIG. 13), but not in the coumarin channel (FIG. 14). Subsequent UV uncaging turned on the fluorescence of coumarin in a UV dose dependent manner, and the coumarin fluorescence increase was not picked up by the Fluo-3 channel. Thus the cellular calcium levels (from Fluo-3) and coumarin intensity levels were monitored simultaneously without interference between the two channels.

EXAMPLE 9

Simultaneous Measuring of Coumarin Transfer and Cytosolic Calcium

Figure 15:
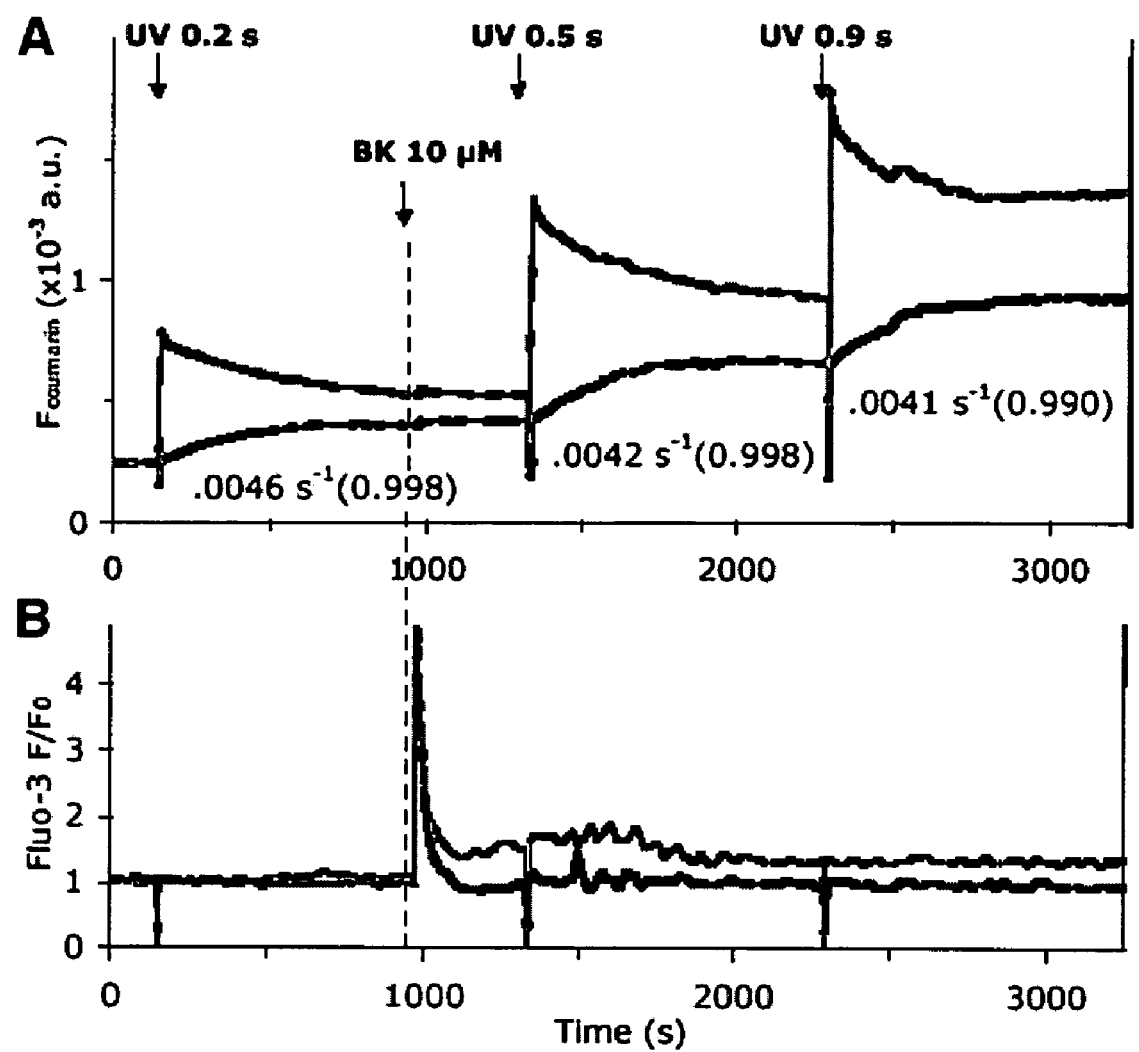
FIG. 15 shows (A) the fluorescence intensities of coumarin in coupled cells after localized uncaging and (B) the concurrent measurements of fluorescence intensities of calcium indicator Fluo-3 in the coupled cells subject to the stimulation of an agonist bradykinin (BK).

Human fibroblasts were loaded with the calcium indicator Fluo-3/AM (Molecular Probes) (Excitation 490±10 nm, Emission 525±10 nm) and a caged and cell permeable coumarin derivative. After loading, cells were washed with HBS buffer and imaged similarly as in Example 4. Fluorescence images were taken of coupled cells. Localized uncaging resulted in constant dye transfer between the donor and recipient cells, as shown in FIG. 15A. The simultaneous measurement of fluorescence intensity of Fluo-3, displayed as fold of increase over the baseline fluorescence $F_0$, allows the study of the effects of cellular calcium on the kinetics of intercellular communications through gap junctions. Bradykinin (BK) (10 µM) was added to the cells after the first localized uncaging to stimulate calcium increase.

EXAMPLE 10

Two Photon Uncaging of NPE-caged Coumarins

A development in the photo-uncaging field is the introduction of the two photon uncaging technique (Furuta, 1999; Brown, 1999; Ando, 2001; Matsuzaki, 2001). This method involves applying high fluxes of infrared (IR) laser light to excite samples in a highly restricted focal volume, or about 1 µm$^3$. Simultaneous absorptions of two or more IR photons with a combined energy equivalent to one UV photon pump the molecule to the excited states. By comparison with the usual one photon UV photolysis, two photon uncaging offers the advantages of releasing active molecules with excellent three dimensional resolution and minimizing photo toxicity to cells. The efficiency of two photon photolysis is measured as the two photon uncaging action cross section $\delta_u$. This parameter is the product of the two-photon absorbance cross section $d_a$ and the uncaging quantum yield $Q_{u2}$, and is measured in the unit of Goeppert-Mayer (GM, 1 GM=10$^{-50}$ cm$^4$s/photon) (Furuta, 1999; Brown, 1999). Ideally, $\delta_u$ of caged molecules should exceed 0.1 GM for biological applications in live specimens (Furuta, 1999).

6-bromo-7-hydroxycoumarin-4-ylmethyl group (Bhc) was first developed as a two photon cage of general usages (Furuta, 1999). More recently, 8-bromo-7-hydroxyquinoline (BHQ) was described as another protecting group of sufficient sensitivity for the two photon photolysis (Fedoryak, 2002). Molecules caged by these groups display two photon uncaging cross sections about 1 GM at 740 nm. In addition, 4-methoxy-7-nitroindoline (MNI) group has also been applied as a two photon caging group, though the $\delta_u$ (0.06 GM at 730 nm) of a MNI caged glutamate is significantly lower than those of molecules based on Bhc or BHQ groups (Canepari, 2001; Matsuzaki, 2001).

So far none of these caging groups have been used to prepare caged fluorophores and no caged fluorophores have been reported to have $\delta_u$ over 0.1 GM.

In contrast to these recent developments, caged compounds employing 2-nitrobenzyl or related protecting groups have fairly low $\delta_u$. DMNB caged compounds such as DM-nitrophen and DMNB-acetate have $\delta_u$ of 0.01~0.03 GM between 720 to 740 nm. Other caged molecules based on NB or NPE groups have negligible $\delta_u$ (Furuta, 1999; Brown, 1999). In contrast, our caged fluorophores have two photon uncaging cross sections at 740 nm to be near 1 Goeppert-Mayer (GM).

Principles of Measuring Two Photon Uncaging Cross Sections

To calculate $\delta_u$, 6-bromo-7-hydroxycoumarin-4-ylmethyl acetate (Bhc-OAc) was used as a reference compound (Furuta, 1999; Fedoryak, 2002). The compounds tested included Compound 2a from FIG. 3 and a compound 2a' having the structure:

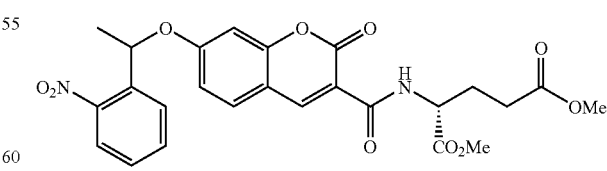

Bhc-OAc, Compound 2a, and Compound 2a' in microcuvettes were illuminated using focused infrared light (740 mn) from a femtosecond-pulsed and mode locked Ti-sapphire laser. The two photon uncaging action cross section was determined using the equation (Furuta, 1999):

$$\delta_u = \frac{2N_P}{C_s \langle I_0^2(t) \rangle \int S^2(r) dV} \quad (1)$$

where $N_p$ is the number of product molecules formed per unit time, $\langle I_0^2(t) \rangle$ is the mean squared light intensity, $S(r)$ is a unitless spatial distribution function, and the integral is over the volume of the microcuvet, and $C_s$ is the substrate concentration. If caged compounds are photolyzed under the identical setting with the same two photon laser power, then the term $\langle I_0^2(t) \rangle \int S^2(r)dV$ should be about the same for different cages. Thus, $\delta_u^a$ of cage "a" can be determined by comparing its rate of product formation ($N_p^a$) with that of reference cage "b" with known $\delta_u^b$ according to the equation:

$$\frac{\delta_u^a}{\delta_u^b} = \frac{N_P^a C_S^b}{N_P^b C_S^a} \quad (2)$$

The formation of coumarins after two photon photolysis of Compound 2a and Compound 5 was quantified similarly as in the one photon uncaging experiments by measuring the fluorescence enhancement. The photolysis of Bhc-OAc was quantified by HPLC analysis as described (Furuta, 1999; Fedoryak, 2002).

Experimental Procedure

Two photon photolysis was carried out using a procedure similar to the one first described by Furuta et al (Furuta, 1999). Samples in 100 mM Mops buffer (pH 7.3) were transferred to a microcuvette (Hellma 105.251-QS). The filling volume of the cuvette was 45 mL. The laser beam from a fs-pulsed and mode-locked Ti-Sapphire laser (Mira 900-F pumped by a Verdi, Coherent, Santa Clara, Calif.) was focused into the center of the cuvette with a focusing lens (01 LPX 029/077, focal length 25 mm, Melles-Griot, Carlsbad, Calif.). After irradiation with 740 nm light, samples were collected and the formation of the products was quantified. The formation of coumarins from caged precursors 2a or 2a' (initial concentration 10 μM) was measured by fluorescence spectroscopy. The photolysis of Bhc-OAc (initial concentration 100 μM) was followed by HPLC. Two-photon uncaging cross sections ($\delta_u$) were calculated from equation (2) and the reported $\delta_u$ of 0.72 GM for Bhc-OAc at 345 mW laser power exiting the cuvette (Fedoryak, 2002).

Experimental Results

Figure 16:
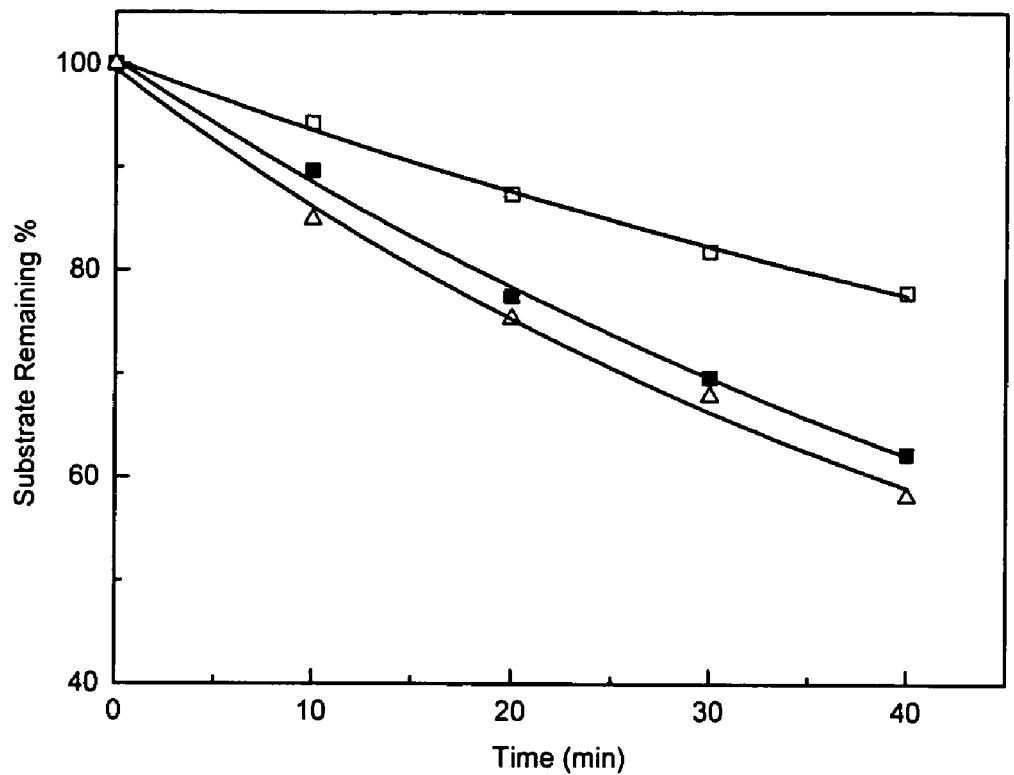
FIG. 16 shows the time course of coumarin fluorescence intensities after two photon uncaging of 6-bromo-7-hydroxycoumarin-4-ylmethyl acetate (Bhc-OAc) and NPE caged compounds 2a (FIG. 3) and an analogue of 2a and 2a', which lack 6-chloro substitution on the coumarin ring at 740 nm; Bhc-Oac is represented by the triangle, compound 2a is represented by the unfilled square, and another NPE caged coumarin, compound 2a' is represented by the filled square.
Figure 16:
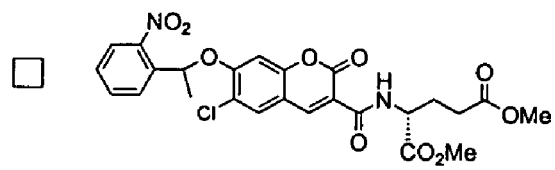
Figure 16:
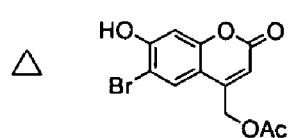
Figure 16:
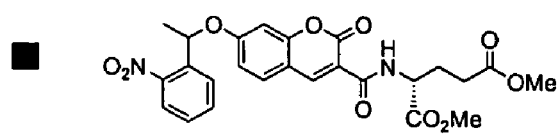

FIG. 16 shows the time courses of the photolysis of Bhc-OAc and NPE caged Compounds 2a and 2a', at 740 nm (average power 590 mW exiting the cuvette). Bhc-Oac is represented by the triangle, Compound 2a is represented by the unfilled square, and Compound 2a' is represented by the filled square. Caged Compounds 2a, 2a', and Bhc-OAc were photolyzed by 740 nm laser light quite efficiently, yet Bhc-OAc and 2a' were about two times more sensitive to two photon uncaging than 2a. Since the reported $\delta_u$ of Bhc-OAc has been measured at 740 nm at the laser power of 345 mW exiting the cuvette (Fedoryak, 2002), we also compared the rates of photolysis of 2a, 2a', and Bhc-OAc at this power level. After 20 minutes of continuous illumination, there were 5.5%, 10%, and 10.6% of photolysis for compounds 2a, 5, and Bhc-OAc, respectively. Using the reported $\delta_u$ of Bhc-OAc (0.72 GM at 740 nm) (Fedoryak, 2002; Furuta, 1999) and equation (2), it was estimated that the $\delta_u$ of 2a and 5 was 0.37 GM and 0.68 GM, respectively.

Caged compounds employing NPE or NB groups have typically shown unmeasurably low two photon uncaging action cross sections. The present NPE-caged fluorophores such as Compound 2a and Compound 5 represent the first example that $\delta_u$ of caged compounds based on 2-nitrobenzyl groups can approach 1 GM. Without wanting to be bound by theory, this result further supports the proposed mechanism that the coumarin moiety serves as an antenna to enhance the light harvesting capability of the molecule and to boost the photolytic efficiency of NPE group.

EXAMPLE 11

Two Photon Uncaging and Imaging

An important and unique property of the current caged fluorophores is that they can be photolyzed with 740 nm infra light by the two photon uncaging, and then imaged with 800 nm infra light by two photon excitation. Infra light at 800 nm does not photolyze caged coumarins, but it excites uncaged coumarin fluorophore efficiently. Because of the three dimensional selectivity of two photon excitations, this combined two photon uncaging and imaging technique offers the possibility of imaging molecular movements in cells in physiological preparations such as intact tissues or organs.

Three human fibroblast cells were loaded with a caged coumarin compound. One cell was exposed to 740 nm infra light, which generated fluorescent coumarin by two photon uncagings. The cells were then imaged with 800 nm infra light. The two cells which were not uncaged by 740 nm light showed negligible fluorescence during two photon imaging. Later, all cells were uncaged by UV light and then imaged using 800 nm excitation, which caused all cells to show fluorescence. FIG. 17 shows the time course of coumarin fluorescence intensity of the three cells. The filled diamond represents fluorescence intensity of the cell that was first uncaged with 740 nm infra light. The open symbols represent the fluorescence intensities of the two cells that were not originally uncaged with 740 nm light. Global UV illumination generated coumarin in all cells.

EXAMPLE 12

Synthesis of Compounds and Experimental Data

Figure 1:
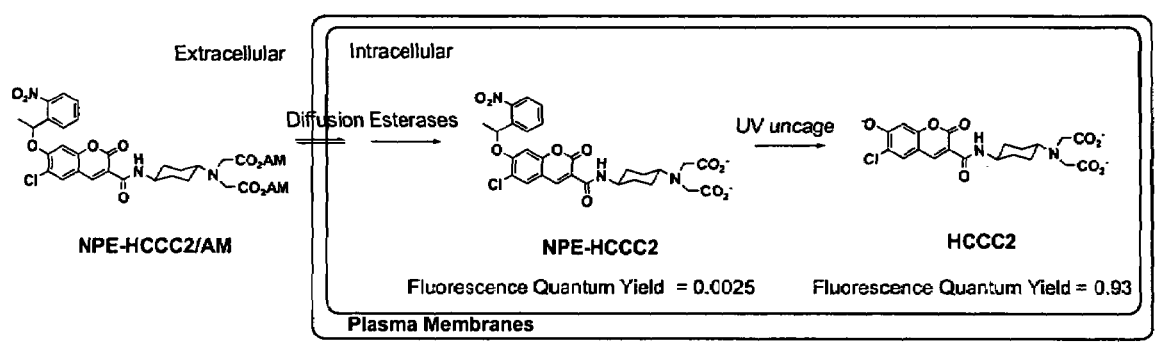
FIG. 1 is a schematic showing general structures and fluorescent properties of a cell permeable and caged fluorophore.
Figure 2:
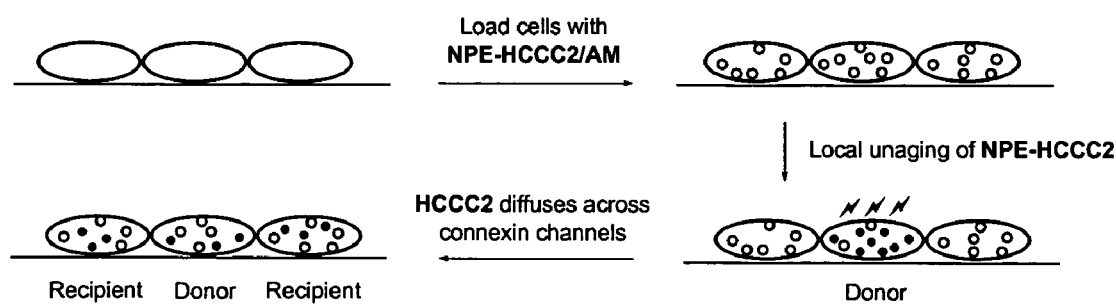
FIG. 2 is a schematic of an imaging assay of cell-cell gap junction communication using localized uncaging of cell permeable and caged fluorophores.
Figure 3:
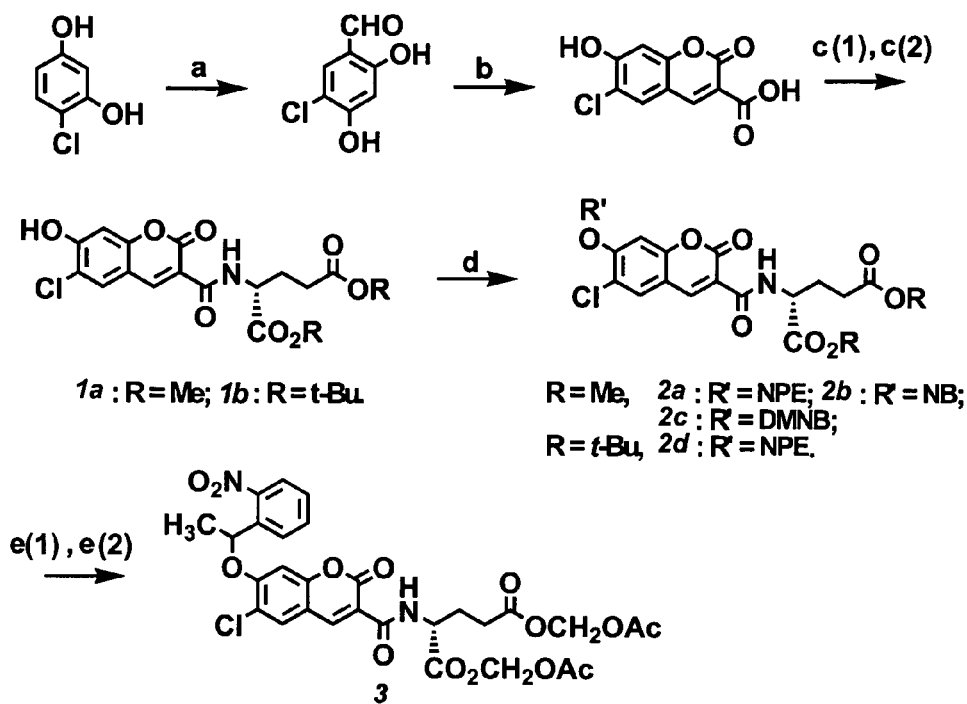
FIG. 3 is a reaction scheme showing the synthesis of a caged fluorophore based on 6-chloro-7-hydroxy-coumarin 3-carboxamide.
Figure 4:
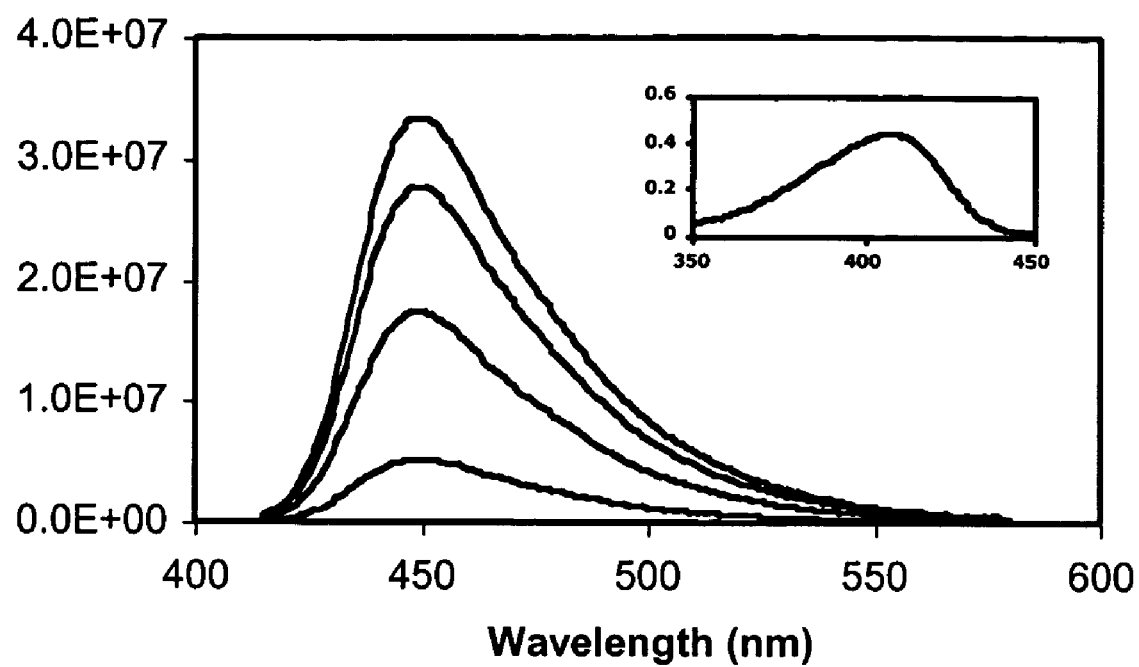
FIG. 4 shows the enhancement of fluorescence emission of an NPE-caged coumarin after increasing durations of V photolysis (from bottom to top, 0 sec, 2 sec, 9 sec, 38 sec and 78 sec UV), and the insert shows the excitation spectrum of uncaged coumarin after complete photolysis.

Synthesis of 2,4-dihydroxy-5-chlorobenzaldehyde (FIG. 3)

At 0° C., a stream of hydrogen chloride was blown into a suspension of 4-chlororesorcinol (10.9 g, 75.43 mmol), $Zn(CN)_2$ (13.5 g, 115 mmol), and KCL (0.25 g, 3.36 mmol) in EtOH (35 mL). The solution was stirred at 0° C. until the absorption of HCl gas stopped. The stirring was continued for another 2 hours at 10° C., during which more precipitate formed. After the precipitate was allowed to settle, the ethereal solution was decanted. The solid was treated with ice water (about 100 mL) and then heated to 100° C. for 0.5 hours. Upon cooling to room temperature, the product was formed as a solid at the bottom of the flask. Filtration and drying under a high vacuum afforded the desired product as a white solid (1.5 g, 11.5%).

Experimental data: $^1$H NMR (CDCl$_3$, δ ppm): 11.25 (s, 1H), 9.69 (s, 1 H), 7.52 (s, 1 H), 6.62 (s, 1 H), 6.18 (br.s, 1H). $^{13}$C NMR (CDCl$_3$, δ ppm): 193.6, 162.9, 158.4, 133.7, 115.9, 112.0, 104.3.

Synthesis of 3-carboxy-6-chloro-7-hydroxycoumarin (FIG. 3)

A suspension of the above benzaldehyde (0.58 g, 3.36 mmol), malonic acid (0.72 g, 6.9 mmol) and a catalytic amount of aniline in pyridine (3.0 mL) was stirred at room temperature for 72 hours. EtOH (5.0 mL) was then added. The mixture was stirred at this temperature for 1 hour, and then was filtered. The filtrate was washed sequentially with 0.1 N HCl, H$_2$O and EtOH to afford a yellow solid. The solid was dried under high vacuum overnight to give the desired product (0.35 g, 43.7%) as a yellow powder.

Experimental data: $^1$H NMR (DMSO-d$_6$, δ ppm): 8.62 (s, 1 H), 7.96 (s, 1 H), 6.87 (s, 1 H). MS: 239.98 calculated for C$_{10}$H$_5$ClO$_5$; observed 241.47 (M+H)$^+$, 263.47 (M+Na)$^+$, 279.45 (M+K)$^+$.

Synthesis of 6-chloro-7-hydroxycoumarin 3-carboxamide (FIG. 3, Compounds 1a and 1b)

A droplet of DMF was added to a suspension of 3-carboxy-6-chloro-7-hydroxycoumarin (85 mg, 0.353 mmol) and SOCl$_2$ (0.253 mL, 3.477 mmol) in CH$_2$Cl$_2$ (5.0 mL) at room temperature. The mixture was stirred at 45° C. for 4 hours and then evaporated to dryness. The residue was suspended in CH$_2$Cl$_2$ (2.0 mL). To this suspension, to prepare compound 1b, a solution of H-D-di-t-butyl glutamate hydrogen chloride (157 mg, 0.53 mmol) and Et$_3$N (196 μL, 1.4 mmol) in CH$_2$Cl$_2$ (3.0 mL) was added. The resulting mixture was stirred at room temperature overnight. The solution was poured into EtOAc, extracted with 0.1 N HCl, washed with brine, dried over Na$_2$SO$_4$, and concentrated to give a residue. The residue was purified by flash chromatography (CH$_2$Cl$_2$/MeOH, 95:5) to afford compound 1b as a slightly yellow power (89 mg, 52.6%).

Experimental data for 1b: $^1$H NMR (CDCl$_3$, δ ppm): 9.24 (d, J=8.0 Hz, 1H), 8.65 (s, 1 H), 7.56 (s, 1 H), 6.98 (s, 1 H), 4.64 (m, 1 H), 2.31-2.42 (m, 2 H), 2.18-2.28 (m, 2 H), 1.47 (s, 9 H), 1.41 (s, 9H). MS: 481.15 calculated for C$_{23}$H$_{28}$ClNO$_8$; observed 504.70 (M+Na)$^+$, 520.67 (M+K)$^+$.

Compound 1a was synthesized similarly using H-D-dimethyl glutamate hydrogen chloride. Experimental data for 1a: $^1$H NMR (CDCl$_3$, δ ppm): 9.17 (d, J=7.6 Hz, 1 H), 8.71 (s, 1 H), 7.64 (s, 1 H), 7.04 (s, 1H), 4.79 (m, 1 H), 3.78 (s, 3 H), 3.67 (s, 3 H), 2.4-2.5 (m, 2 H), 2.15-2.40 (m, 2H). MS: 397.06 calculated for C$_{17}$H$_{16}$ClNO$_8$; obsd.: 398.59 (M+H)$^+$, 420.56 (M+Na)$^+$, 436.54 (M+K)$^+$.

Synthesis of 6-chloro-7-(2-nitrophenyl)ethoxy-coumarin 3-carboxamide (FIG. 3, Compounds 2a, 2b, 2c, and 2d)

To prepare compound 2d, a solution of compound 1b (45.3 mg, 0.0939 mmol), NPE bromide (25.9 mg, 0.113 mmol) and DIEA (32.7 μL, 0.187 mmol) in acetonitrile (300 μL) was stirred at 45° C. for 10 hours. After cooling down to room temperature, the reaction mixture was directly purified by silica gel chromatography with CH$_2$Cl$_2$/MeOH (98:2) as eluant. The desired product was obtained as a solid after drying (42.8 mg, 72.5%).

Experimental data for 2d: $^1$H NMR (CD$_3$Cl, δ ppm): 9.05 (d, J=8.0 Hz, 1 H), 8.66 (s, 1 H), 8.05 (d, J=8.0 Hz, 1H), 7.58-7.72 (m, 3H), 7.45 (m, 1H), 6.67 (d, J=1.6 Hz, 1H), 6.22 (q, J=6.4 Hz, 1 H), 4.62 (m, 1H), 2.13-2.34 (m, 4 H), 1.76 (d, J=6.0 Hz, 3 H), 1.43 (s, 9 H), 1.36 (s, 9 H). MS: 630.20 calculated for C$_{31}$H$_{35}$ClN$_2$O$_{10}$; observed 653.99 (M+Na)$^+$, 669.97 (M+K)$^+$.

Compounds 2a, 2b and 2c were synthesized similarly as 2d from a starting material of compound 1a.

Experimental data for 2a: $^1$H NMR (CD$_3$Cl, δ ppm): 9.08 (d, J=8.0 Hz, 1 H), 8.69 (s, 1 H), 8.10 (d, J=8.0 Hz, 1 H), 7.6-7.75 (m, 3H), 7.4-7.5 (m, 1 H), 6.71 (d, J=2.0 Hz, 1 H), 6.27 (q, J=6.4 Hz, 1H), 4.78 (m, 1H), 3.76 (d, 3 H), 3.64 (d, 3 H), 2.23-2.5 (m, 3 H), 2.03-2.18 (m, 1 H), 1.80 (d, J=6.1 Hz, 3 H). MS: 546.10 calculated for C$_{25}$H$_{23}$ClN$_2$O$_{10}$; observed 569.8 (M+Na)$^+$, 585.82 (M+K)$^+$.

Experimental data for 2b: $^1$H NMR (CD$_3$Cl, δ ppm): 9.14 (d, J=7.6 Hz, 1 H), 8.76 (s, 1H), 8.25 (dd, J=8.4, 1H), 8.00 (d, J=8.2 Hz, 1H), 7.76 (t, J=7.6, 1H), 7.72 (s, 1 H), 7.57 (t, J=7.6, 1H), 7.05 (s, 1 H), 5.62 (s, 2 H), 4.80 (m, 1 H), 3.77 (s, 3 H), 3.67 (s, 3 H), 2.3-2.5 (m, 3H), 2.08-2.18 (m, 1 H). MS: 532.09 calculated for C$_{24}$H$_{21}$ClN$_2$O$_{10}$; observed 533.94 (M+H)$^+$, 555.89 (M+Na)$^+$, 571.88 (M+K)$^+$.

Experimental data for 2c: $^1$H NMR (CD$_3$Cl, δ ppm): 9.14 (d, J=7.6 Hz, 1H), 8.76 (s, 1 H), 7.81 (s, 1H), 7.75 (s, 1 H), 7.6 (s, 1H), 7.12 (s, 1 H), 5.62 (s, 2H), 4.80 (m, 1 H), 4.05 (s, 3H), 3.98(s, 3 H), 3.77 (s, 3H), 3.65 (s, 3H), 2.3-2.52 (m, 3H), 2.08-2.18 (m, 1 H). MS: 592.11 calculated for C$_{26}$H$_{25}$ClN$_2$O$_{12}$; observed 593.69 (M+H)$^+$, 615.69 (M+Na)$^+$, 631.67 (M+K)$^+$.

Synthesis of the AM ester of 6-chloro-7-(2-nitrophenyl)ethoxy-coumarin 3-carboxamide (FIG. 3, Compound 3)

A solution of compound 2d (12 mg, 0.0191 mmol), CF$_3$CO$_2$H (38.4 μL, 0.498 mmol), triethylsilane (7.5 μL, 0.048 mmol) and CH$_2$Cl$_2$ (100 μL) was stirred at room temperature. Upon completion of the reaction as monitored by TLC, the reaction mixture was concentrated to a residue which was used directly for the esterification. The residue was resuspended in acetonitrile (200 μL). After adding bromomethylacetate (3.5 μL, 0.0466 mmol) and DIEA (11.1 μL, 0.636 mmol), the solution was stirred at r.t. overnight. After removing the solvent, H$_2$O (200 μL) was added. The mixture was extracted with CH$_2$Cl$_2$ (3×10 mL). The combined extracts were dried (Na$_2$SO$_4$) and concentrated to give a residue. The residue was purified by flash chromatography eluting with CH$_2$Cl$_2$/MeOH (98/2) to give 6.3 mg of desired product (60%).

Experimental data: $^1$H NMR (CD$_3$Cl, δ ppm): 9.09 (d, J=7.6 Hz, 1H), 8.68 (s, 1 H), 8.11 (d, J=8.0 Hz, 1 H), 7.6-7.8 (m, 3H), 7.49 (m, 1H), 6.71 (s, 1 H), 6.27 (m, 1H), 5.69-5.81 (m, 4H), 4.79 (m, 1 H), 2.55-2.52 (m, 2 H), 2.31-2.40 (m, 2 H), 2.11 (s, 3 H), 2.09 (s, 3H), 1.81 (d, J=6.4 Hz, 3H). MS: 662.12 calculated for C$_{29}$H$_{27}$ClN$_2$O$_{14}$; observed 663.86 (M+H)$^+$, 685.86 (M+Na)$^+$.

Synthesis of Compound 4 (FIG. 6)

To a stirred solution of 1,4-cis-diaminocyclohexane (0.68 g, 5.955 mmol) in CH$_2$Cl$_2$ was added trifluroacetic anhydride (0.91 ml, 6.550 mmol) at 0° C. The resulting mixture was stirred at room temperature overnight, diluted with CH$_2$Cl$_2$, washed with saturated NaHCO$_3$ (3×20 mL) and brine (3×20 mL), and concentrated to give a white solid. This was used for next step without further purification.

Experimental data: MS: 210.10 calculated for $C_8H_{13}F_3N_2O$; observed 212.63 (M+H$^+$), 232.59 (M+Na$^+$).

Synthesis of Compound 5 (FIG. 6)

To a stirred suspension of compound 4 (0.30 g, 1.427 mmol) and KHCO$_3$ (0.36 g, 3.596 mmol) in DMF (2.0 mL) was added dropwise tert-butyl bromoacetate (0.47 mL, 3.139 mmol) at room temperature. The resulting mixture was stirred at room temperature overnight and then diluted with EtOAc (300 mL), washed with saturated NH$_4$Cl, dried with Na$_2$SO$_4$ and concentrated to a residue. The residue was purified by flash chromatography eluting with hexane/EtOAc (9:1 to 4:1) to afford compound 5 (223 mg, 35.6%) as a colorless oil.

Experimental data: MS: 438.23 calculated for $C_{20}H_{33}F_3N_2O_5$; observed 439.21 (M+H$^+$), 461.17 (M+Na$^+$). $^1$HNMR (400 MHz, δ ppm, CDCl$_3$): 6.14 (d, J=7.3 Hz, 1 H), 3.71 (m, 1 H), 3.43 (s, 4H), 2.68 (tt, J=11.2, 3.2 Hz, 1 H), 2.04 (d, J=12.0 Hz, 2 H), 1.94 (d, J=12.0 Hz, 2 H), 1.42 (s, 18 H), 1.19-1.38 (m, 4 H).

Synthesis of Compound 6 (FIG. 6)

A solution of compound 5 (75 mg, 0.172 mmol) in MeOH—H$_2$O (2.0 mL -0.1 mL) was treated with NaOH (171 µL, 1 N NaOH) at room temperature. The resulting solution was stirred at room temperature for 10 hours and then diluted with EtOAc (100 mL), washed with saturated NaHCO$_3$, dried with Na$_2$SO$_4$, and concentrated to afford a residue which was used for next step without further purification.

Experimental data: MS: 342.25 calculated for $C_{18}H_{34}N_2O_4$; observed 364.96 (M+Na$^+$), 380.91 (M+K$^+$).

A droplet of DMF was added to a suspension of 6-chloro-7-hydroxycoumarin 3-carboxylate (21.5 mg, 0.0894 mmol) and SOCl$_2$ (65 µL, 0.894 mmol) at room temperature. The resulting mixture was stirred at 40° C. for 4 hours and then evaporated to dryness. The residue prepared in the first step was suspended in CH$_2$Cl$_2$ (2.0 mL) and to this stirred suspension was added solution of the above intermediate in CH$_2$Cl$_2$ (2.0 mL), followed by addition of Et$_3$N (37.4 µL, 0.274 mmol). The resulting mixture was stirred at room temperature overnight and then diluted with EtOAc (150 mL), washed with brine, dried with Na$_2$SO$_4$, and concentrated to give a residue. The residue was purified by flash chromatography (hexane/EtOAc, 3:2 to 1:1) to afford compound 6 (12.2 mg, 24.1% for two steps) as a yellow solid.

Experimental data: MS: 564.22 calculated for $C_{28}H_{37}ClN_2O_8$; observed 565.86 (M+H$^+$), 587.86 (M+Na$^+$). $^1$H NMR (400 MHz, δ ppm, CDCl$_3$): 8.74 (s, 1H), 8.62 (d, J=8.0 Hz, 1 H), 7.66 (s, 1 H), 7.06 (s, 1 H), 3.86 (m, 1 H), 3.44 (s, 4 H), 2.70 (tt, J=11.2, 3.2 Hz, 1 H), 2.09 (d, J=10.6 Hz, 2 H), 1.94(d, J=10.6 Hz, 2H), 1.45 (s, 18 H), 1.24-1.39 (m, 4 H).

Synthesis of Compound 7 (FIG. 6)

A solution of compound 6 (7.4 mg, 0.0131 mmol), NPE-Br (4.5 mg, 0.0196 mmol) and DIPA (6.8 µL, 0.0393 mmol) in CH$_3$CN—CH$_2$Cl$_2$ (0.5 mL, 1:1) was stirred at 40° C. for 8 hours and then cooled to room temperature. The reaction mixture was diluted with EtOAc (10 mL), washed with saturated NH$_4$Cl, and dried with Na$_2$SO$_4$. The residue was purified by flash chromatography eluting with hexane/EtOAc (4:1 to 7:3) to afford compound 7 (5.4 mg, 57.4%) as a slightly yellow solid.

Experimental data: MS: 713.27 calculated for $C_{36}H_{44}ClN_3O_{10}$; observed 714.17 (M+H$^+$), 736.16 (M+Na$^+$). $^1$H NMR (400 MHz, δ ppm, CDCl$_3$): 8.71 (s, 1H), 8.48 (d, J=8.0 Hz, 1 H), 8.10 (dd, J=8.0, 1.0 Hz, 1H), 7.88 (J=8.0, 1.0 Hz, 1 H), 7.76 (s, 1 H), 7.63 (td, J=6.4, 1.2 Hz, 1 H), 7.48 (td, J=6.8, 1.6 Hz, 1H), 6.69 (s, 1H), 6.25 (q, J=6.4 Hz, 1 H), 3.83 (m, 1 H), 3.45 (s, 4 H), 3.45 (s, 4 H), 2.69 (tt, J=11.2, 3.2 Hz), 2.07 (d, J=10.9 Hz, 2 H), 1.93 (d, J=10.6 Hz, 2 H), 1.80 (d, J=6.4 Hz, 3 H), 1.56 (s, 18 H), 1.24-1.43 (m, 4 H).

Synthesis of Compound 8 (FIG. 6)

To a stirred solution of compound 7 (5.4 mg, 0.00756 mmol) and triethylsilane (5.9 µL, 0.0378 mmol) in CH$_2$Cl$_2$ (200 µL) was added CF$_3$CO$_2$H (15.7 µL, 0.204 mmol). The resulting solution was stirred at room temperature in the dark for 4.5 hours and then evaporated to a residue. The dried residue was dissolved in acetonitrile (150 µL). To this solution bromomethylacetate (3.7 µL, 0.0378 mmol) and DIPA (13.2 µL, 0.0756 mmol) were added, respectively. The resulting solution was stirred at room temperature in the dark overnight. The reaction solution was diluted with CH$_2$Cl$_2$ (10 mL), washed with saturated NH$_4$Cl, dried with Na$_2$SO$_4$, and concentrated to afford a residue. The residue was purified by flash chromatography eluting with hexane/EtOAc (3:2) to afford compound 8 (1.8 mg, 32.5% for two steps) as a yellow solid.

Experimental data: MS: 745.19 calculated for $C_{34}H_{36}ClN_3O_{14}$; observed 746.25 (M+H$^+$), 768.23 (M+Na$^+$). $^1$H NMR (400 MHz, δ ppm, CDCl$_3$): 8.71 (s, 1 H), 8.49 (d, J=8.0 Hz, 1 H), 8.10 (dd, J=8.0, 1.2 Hz, 1 H), 7.73 (dd, J=8.0, 1.2 Hz, 1 H), 7.67 (s, 1H), 7.64 (td, J=6.8, 1.2 Hz, 1 H), 7.49 (td, J=6.8, 1.2 Hz, 1 H), 6.69 (s, 1 H), 6.25 (s, 1 Hz, 1 H), 5.75 (s, 4 H), 3.82 (m. 1 H), 3.62 (s, 4 H), 2.71 (tt, J=11.4, 3.2 Hz, 1 H), 2.11 (s, 6 H), 1.92 (d, J=6.4 Hz, 2 H), 1.80 (d, J=6.4 Hz, 2 H), 1.20-1.42 (m, 4 H).

Synthesis of Compound 9 (FIG. 18)

To prepare Compound 9, paraformaldyhyde (127 mg, 4.233 mmol) was mixed with di-tert-butyl iminodiacetate (1.04 g, 4.233 mmol) in CH$_3$CN (3.0 mL). After heating the mixture at 60° C. for 0.5 h, 2,4-dihydroxybenzaldehyde (0.58 g, 4.233 mmol) in CH$_3$CN/H$_2$O (1:1, 6.0 mL) was added. The reaction was continued at 80° C. for 3.5 h. After cooling to r.t., the reaction mixture was diluted with EtOAc (250 mL), washed (sat. NH$_4$Cl), dried (Na$_2$SO$_4$) and concentrated under the vacuum. The residue was purified by flash chromatography (FC) eluting with hexane/EtOAc (4:1). The product was obtained as a white solid (1.4 g, 87.5%). $^1$H NMR (400 MHz, δ ppm, CDCl$_3$): 11.76 (s, 1 H), 9.63 (s, 1 H), 7.33 (d, J=8.8 Hz, 1 H), 6.51 (d, J=8.8 Hz, 1 H), 4.00 (s, 2 H), 3.39 (s, 4 H), 1.44 (s, 18H). MS: 395.19 calcd for $C_{20}H_{29}NO_7$; obsd: 396.52 (M+H)$^+$, 418.54 (M+Na)$^+$, 434.54 (M+K)$^+$.

Synthesis of Compound 10 (FIG. 18)

To compound 9 (0.28 g, 0.709 mmol), malonic acid (0.15 g, 1.418 mmol) and aniline (4.0 µL) in pyridine (1.0 mL) were reacted at r.t. for 3 days. After removing the solvent under vacuum, the residue was dissolved in EtOAc (150 mL), washed (0.1 N HCl and sat. NH$_4$Cl), dried (Na$_2$SO$_4$) and concentrated. Purification by FC (CH$_2$Cl$_2$/MeOH, 9:1) provided the product as a yellow solid (0.26 g, 78.8%). $^1$H NMR (400 MHz, δ ppm, CDCl$_3$): 8.79 (s, 1 H), 7.54 (d, J=8.8 Hz, 1 H), 6.94 (d, J=8.8 Hz, 1 H), 4.22 (s, 2 H), 3.42 (s, 4 H), 1.47 (s, 18 H). MS: 463.18 calcd for $C_{23}H_{29}NO_9$; obsd: 486.7 $(M+Na)^+$.

Synthesis of Compound 11 (FIG. 18)

Oxalyl chloride (38.5 µL, 0.44 mmol) was added dropwise to a stirred solution of 10 (60.5 mg, 0.131 mmol) in $CH_2Cl_2$ (2.0 mL). A catalytic amount of DMF was then added. The reaction was continued at r.t. for 4 h. After removing the solvent under vacuum, the residue was suspended in $CH_2Cl_2$ (2.0 mL). Tert-amylamine (30.4 µL, 0.262 mmol) was then added. The mixture was stirred at r.t. overnight and then diluted with EtOAc (150 mL), washed (sat. $NH_4Cl$), dried ($Na_2SO_4$) and concentrated. The residue was purified by FC (hexane/EtOAc, 3:2) to provide 11 as an oil (20.6 mg, 29.6%). $^1H$ NMR (400 MHz, δ ppm, $CDCl_3$): 8.74 (s, 1 H), 7.45 (d, J=8.8 Hz, 1 H), 6.88 (d, J=8.8 Hz, 1 H) 4.20 (s, 2 H), 3.40 (s, 4 H), 1.79 (q, J=7.2 Hz, 2H), 1.48 (s, 18 H), 1.40 (s, 6 H), 0.89 (t, J=7.2 Hz, 3 H). MS: 532.28 calcd for $C_{28}H_{40}N_2O_8$; obsd: 555.70 $(M+Na)^+$, 571.67 $(M+K)^+$.

Synthesis of Compound 12 (FIG. 18)

Compound 11 (35.8 mg, 0.0673 mmol), NPE-Br (20.1 mg, 0.0874 mmol) and DIEA (29.3 µL, 0.168 mmol) in $CH_3CN$ (200 µL) were stirred at 70° C. overnight. The mixture was then diluted with EtOAc (50 mL), washed (sat.$NH_4Cl$), dried ($Na_2SO_4$) and concentrated. The residue was purified by FC (hexane/EtOAc, 4:1) to afford 12 as an oil (20.6 mg, 44.4%) which was used immediately for the next step. MS: 681.33 calcd for $C_{36}H_{47}N_3O_{10}$; obsd: 682.11 $(M+H)^+$.

Synthesis of Compound 13 (FIG. 18)

Compound 12 (20.6 mg, 0.0302 mmol), $Et_3SiH$ (31.2 µL, 0.196 mmol) and $CF_3CO_2H$ (137.2 µL) in $CH_2Cl_2$ (150 µL) were stirred at r.t. for 4.5 h. After evaporating solvents under a vacuum, the residue was redissolved in $CH_3CN$ (150 µL). DIEA (55.7 µL, 0.321 mmol) and bromomethylacetate (21.1 µL, 0.214 mmol) were then added. The resulting mixture was stirred at r.t. overnight and then diluted with EtOAc (50 mL), washed (sat. $NH_4Cl$), dried ($Na_2SO_4$) and concentrated. Purification by FC (hexane/EtOAc, 3:2) provided 13 as an oil (4.5 mg, 20.9%). $^1H$ NMR (400 MHz, δ ppm, $CDCl_3$): 8.69 (s, 1 H), 8.6 (s, 1H), 8.02 (d, J=7.6 Hz, 1 H), 7.85 (d, J=7.6 Hz, 1 H), 7.61 (t, J=7.6 Hz, 1 H), 7.43 (t, J=7.6 Hz, 1 H), 7.38 (d, J=8.8 Hz, 1 H), 6.62 (d, J=8.8 Hz, 1 H), 6.22 (m, 1 H), 5.75 (s, 4 H), 4.43 (d, J=13.4 Hz, 1 H), 4.18 (d, J=13.4 Hz, 1 H), 3.78 (s, 4 H), 2.09 (s, 6 H), 1.78 (m, 5 H), 1.39 (s, 6 H), 0.89 (t, J=7.6 Hz, 3H). MS: 713.24 calcd for $C_{36}H_{47}N_3O_{10}$; obsd: 737.06 $(M+Na)^+$.

Synthesis of Compound 14 (FIG. 19)

Oxalyl chloride (70 µL) was added to compound 10 (72.5 mg, 0.157 mmol) dissolved in $CH_2Cl_2$ (2.5 mL). A catalytic amount of DMF was then added. The reaction was continued at r.t. for 2 h. After removing the solvent under vacuum, the residue was suspended in $CH_2Cl_2$ (2.0 mL). H-Aib-OtBu·HCl (40.0 mg, 0.204 mmol) and $Et_3N$ (65.5 µL, 0.471 mmol) were then added. The mixture was stirred at r.t. overnight and then diluted with EtOAc (150 mL), washed (sat. $NH_4Cl$), dried ($Na_2SO_4$) and concentrated. The residue was purified by FC (hexane/EtOAc, 3:2) to provide 14 as an oil (68%). $^1H$ NMR (400 MHz, δ ppm, $CDCl_3$): 9.12 (s, 1 H), 8.74 (s, 1 H), 7.45 (d, J=8.4 Hz, 1 H), 6.87 (d, J=8.4 Hz, 1 H), 4.21 (s, 2 H), 3.40 (s, 4 H), 1.59 (s, 6 H), 1.48 (s, 18 H), 1.46 (s, 9 H). MS: 604.30 calcd for $C_{31}H_{44}N_2O_{10}$; obsd.: 604.66 $(M+H)^+$.

Synthesis of Compound 15 (FIG. 19)

Compound 14 (62.1 mg, 0.103 mmol), NPE-bromide (47.3 mg, 0.206 mmol) and DIEA (53.7 µL, 0.309 mmol) in $CH_3CN$ (0.4 mL) were stirred at 60° C. overnight. The solution was diluted with EtOAc (100 mL), washed (sat.$NH_4Cl$), dried ($Na_2SO_4$) and concentrated to a residue. The residue was purified by FC (hexane/EtOAc, 7:3) affording 15 as a yellow solid (52.6 mg, 67.9%) which was used immediately for the next step. MS: 753.35 calcd for $C_{39}H_{51}N_3O_{12}$; obsd.: 754.12 $(M+H)^+$.

Synthesis of Compound 16 (FIG. 19)

Compound 15 (12.6 mg, 0.0167 mmol) and $Et_3SiH$ (21.3 µL, 0.134 mmol) were mixed in $CH_2Cl_2$ (0.5 mL). TFA (0.5 mL) was added. The reaction was followed by TLC until the starting material disappeared. After removing solvents under a vacuum, the residue was suspended in $CH_3CN$ (0.1 mL). DIEA (29.0 µL) and AM-Br (9.8 µL, 0.1 mmol) were then added. The mixture was stirred at r.t. overnight, diluted with EtOAc, washed (sat.$NH_4Cl$), dried ($Na_2SO_4$) and concentrated. The residue was purified by FC (hexane/EtOAc, 3:2) to give 16 as an oil (3.4 mg, 25% for two steps). $^1H$ NMR (400 MHz, δ ppm, $CDCl_3$): 9.01 (s, 1 H), 8.62 (s, 1 H), 8.02 (d, J=8.0 Hz, 1 H), 7.85 (d, J=8.0 Hz, 1 H), 7.62 (t, J=8.0 Hz, 1 H), 7.43 (t, J=8.0 Hz, 1H), 7.38 (d, J=8.2 Hz, 1 H), 6.63 (d, J=8.0 Hz, 1 H), 6.24 (m, 1 H), 5.76 (s, 4 H), 5.75 (s, 2 H), 4.43 (d, J=13.2 Hz, 1 H), 4.18 (d, J=13.2 Hz, 1H), 3.78 (s, 4 H), 2.11 (s, 9 H), 1.78 (d, J=6.8 Hz, 3 H), 1.55 (s, 6 H). MS: 801.22 calcd for $C_{36}H_{39}N_3O_{18}$; obsd.: 823.84 $(M+Na)^+$.

Synthesis of HCC—NHS (FIG. 20)

7-Hydroxycoumarin 3-carboxylate (88.2 mg, 0.428 mmol) in pyridine (3.0 mL) was reacted with succinimidyl trifluoroacetate (210.9 mg, 1.070 mmol) at r.t. overnight. The reaction mixture was diluted with EtOAc (200 mL), washed with 6N HCl and sat. $NH_4Cl$, dried over $Na_2SO_4$ and concentrated. The residue was purified by FC (EtOAc/hexane, 4:1). HCC—NHS (48 mg, 37.2%) was obtained as a yellow solid. $^1H$ NMR (400 MHz, δ ppm, $DMSO-d_6$): 8.99 (s, 1 H), 7.85 (d, J=8.8 Hz, 1 H), 6.87 (dd, J=8.8, 1.2 Hz, 1 H), 6.75 (d, J=1.2 Hz, 1 H), 2.86 (s, 4 H). MS: 303.04 calcd for $C_{14}H_9NO_7$; obsd.: 303.98 $(M+H)^+$, 325.98 $(M+Na)^+$.

Synthesis of NPE-HCC—NHS (FIG. 20)

$MnO_2$ (200 mg) was added to a suspension of 2-nitroacetophenone hydrazone (27.1 mg, 0.151 mmol) in $CHCl_3$ (2.0 mL). The mixture was stirred at r.t. for 10 min and then filtered. The filtrate was added to a EtOH solution (1.0 mL) containing HCC—NHS (22.9 mg, 0.0755 mmol). After reacting at r.t. for 4 h, the mixture was concentrated and purified by FC (hexane/EtOAc, 3:2 to 1:1) to give the product NPE-HCC—NHS as a yellow solid (5.0 mg, 15%). $^1H$ NMR (400 MHz, δ ppm, $CDCl_3$): 8.67 (s, 1 H), 8.08 (d, J=8.0 Hz, 1 H), 7.25-7.69 (m, 4 H), 6.89 (dd, J=8.0, 1.2 Hz, 1 H), 6.71 (d, J=1.2 Hz, 1 H), 6.21 (m, 1 H), 2.88 (s, 4 H), 1.72 (d, J=6.7 Hz, 3H). MS: 452.09 calcd for $C_{22}H_{16}N_2O_9$; obsd: 475.07 $(M+Na)^+$.

Synthesis of Hydroxycoumarin 3-methylcarboxylate Compound 17 (FIG. 21)

7-Hydroxycoumarin 3-carboxylate (162 mg, 0.786 mmol) in anhydrous MeOH (6.0 mL) was treated with a droplet of acetyl chloride. The resulting mixture was stirred at r.t. overnight, and then diluted with EtOAc (200 mL), washed with sat. NH$_4$Cl, and dried over Na$_2$SO$_4$. The concentrated residue was purified by FC (hexane/EtOAc, 1:1) to give the product as a yellow solid(148 mg, 86%). $^1$H NMR (400 MHz, δ ppm, CDCl$_3$): 8.63 (s, 1H), 7.7 (d, J=8.0 Hz, 1 H), 6.82 (dd, J=8.0, 1.0 Hz, 1 H), 6.72 (d, J=1.0 Hz, 1 H), 3.78(s, 3H). MS: 220.04 calcd for C$_{10}$H$_8$O$_5$; obsd.: 220.96 (M+H)$^+$, 242.94 (M+Na)$^+$.

Synthesis of 7-[1-(2-Nitrophenyl)ethoxy]-coumarin 3-methylcarboxylate Compound 18 (FIG. 21)

A solution of 17 (145 mg, 0.659 mmol), NPE bromide (227.3 mg, 0.989 mmol) and DIEA (286 μL, 0.989 mmol) in CH$_3$CN (1.0 mL) was stirred at 60° C. overnight. The mixture was diluted with EtOAc (100 mL), washed (sat. NH$_4$Cl), dried (Na$_2$SO$_4$), and concentrated to give a residue. The residue was purified by FC (hexane/EtOAc, 7:3) to give 18 as a yellow solid (198 mg, 82%). $^1$H NMR (400 MHz, δ ppm, CDCl$_3$): 8.42 (s, 1 H), 8.04 (dd, J=8.0, 1.0 Hz, 1 H), 7.57-7.65 (m, 2H), 7.4-7.47 (m, 2 H), 6.84 (dd, J=8.0 1.0 Hz, 1 H), 6.62 (d, J=1.0 Hz, 1 H), 6.14 (m, 1H), 3.84 (s, 3 H), 1.72 (d, J=6.0 Hz, 3 H). MS: 369.08 calcd for C$_{19}$H$_{15}$NO$_7$; obsd.: 370.06 (M+H)$^+$, 392.04 (M+Na)$^+$, 408.04 (M+K)$^+$.

Synthesis of NPE-HCC-TFP (FIG. 21)

Compound 18 (95.6 mg, 0.259 mmol) in MeOH/H$_2$O (1.65 mL, 10:1) was saponified with LiOH (0.39 mmol, 0.5 M×0.78 mL) at r.t. overnight. Another portion of LiOH (1.5 eq) was added. The hydrolysis was continued until the starting material disappeared. The reaction mixture was acidified with 0.1 N HCl and extracted with EtOAc (3×50 mL). The combined organic extracts were washed with sat. NH$_4$Cl, dried over Na$_2$SO$_4$ and concentrated to a residue. MS analysis showed the expected molecular weight: 355.07 calcd for C$_{18}$H$_{13}$NO$_7$; obsd.: 378.01 (M+Na)$^+$. This was used directly for the next step.

The above intermediate was dissolved in DMF (1.0 mL). 2,3,5,6-Tetrafluorophenol (51.6 mg, 0.311 mmol), DMAP (cat.) and ED-HCl (59.6 mg, 0.311 mmol) were then added. The resulting mixture was stirred at r.t. overnight. It was then diluted with EtOAc (150 mL), washed (sat. NH$_4$Cl), dried (Na$_2$SO$_4$) and concentrated. The resulting residue was purified by FC (hexane/EtOAc, 9:1) to give NPE-HCC-TFP (42.5 mg, 35% for two steps). $^1$H NMR (400 MHz, δ ppm, CDCl$_3$): 8.74 (s, 1 H), 8.08 (d, J=8.4 Hz, 1 H), 7.46-7.71 (m, 4 H), 7.02 (m, 1 H), 6.92 (dd, J=8.4, 1.2 Hz, 1 H), 6.73 (d, J=1.2 Hz, 1 H), 6.22 (m, 1 H), 1.76 (d, J=6.0 Hz, 3 H). $^{19}$F NMR (282 MHz, δ ppm, CDCl$_3$): −139 (m, 2F), −152 (m, 2F). MS: 503.06 calcd for C$_{24}$H$_{13}$F$_4$NO$_7$; obsd.: 526.62 (M+Na)$^+$, 542.62 (M+K)$^+$.

Synthesis of 7-Hydroxycoumarin 3-carboxamide Compound 19 (FIG. 21)

7-Hydroxycoumarin 3-carboxylate (162 mg, 0.786 mmol) was dissolved in DMF (3.0 mL). H-tert-butyl glycine (0.29 g, 1.748 mmol), HOBt (0.22 g, 1.6 mmol) and ED-HCl (0.31 g, 1.60 mmol) were added. The resulting mixture was allowed to react at r.t. overnight. It was then diluted with EtOAc (250 mL), washed with sat. NH$_4$Cl, dried over Na$_2$SO$_4$ and concentrated. The residue was purified by FC (hexane/EtOAc, 3:2) to afford 19 as a yellow solid (0.42 g, 91%). $^1$H NMR (400 MHz, δ ppm, CDCl$_3$): 9.21 (t, J=5.6 Hz, 1 H), 8.57 (s, 1 H), 7.38 (d, J=8.8 Hz, 1 H), 6.85 (dd, J=8.8, 1.0 Hz, 1 H), 6.79 (d, J=1.0 Hz, 1H), 4.14 (d, J=6.0 Hz, 2H), 1.52 (s, 9H). MS: 319.11 calcd for C$_{16}$H$_{17}$NO$_6$; obsd.: 342.04 (M+Na)$^+$, 358.02 (M+K)$^+$.

Synthesis of 7-[1-(2-Nitrophenyl)ethoxy]-coumarin 3-carboxamide Compound 20 (FIG. 21)

A solution containing 19 (0.42 g, 1.316 mmol), NPE bromide (0.39 g, 1.711 mmol) and DIEA (0.458 mL, 2.632 mmol) was heated at 60° C. overnight. The mixture was then diluted with EtOAc (350 mL), washed (sat.NH$_4$Cl), dried (Na$_2$SO$_4$) and concentrated. The residue was purified by FC (hexane/EtOAc, 3:2) to give 20 as a yellow solid (0.50 g, 81%). $^1$H NMR (400 MHz, δ ppm, CDCl$_3$): 9.09 (t, J=5.2 Hz, 1 H), 8.76 (s, 1 H), 8.07 (d, J=8.0 Hz, 1 H), 7.67 (dd, J=8.0 Hz, 1.0 Hz, 1 H), 7.60 (t, J=8.0 Hz, 1 H), 7.51 (d, J=8.0 Hz, 1 H), 7.46 (t, J=8.0 Hz, 1 H), 6.87 (dd, J=8.0, 1.0 Hz, 1 H), 6.72 (d, J=1.2 Hz, 1 H), 6.18 (m, 1 H), 4.10 (d, J=4.2 Hz, 2 H), 1.74 (d, J=6.4 Hz, 3 H), 1.48 (s, 9 H). MS: 468.15 calcd for C$_{24}$H$_{24}$N$_2$O$_8$; obsd.: 491.4 (M+Na)$^+$, 507.4 (M+K)$^+$.

Synthesis of NPE-HCC-Gly-NHS (FIG. 21)

Compound 20 (81 mg, 0.173 mmol) was mixed with Et$_3$SiH (81.3 μL, 0.519 mmol) in CH$_2$Cl$_2$ (2.0 mL). Trifluoroacetic acid (1.5 mL) was added to the solution. The reaction was monitored by TLC until the starting material disappeared. Evaporation of solvent gave a residue which was used directly for the next step. MS analysis showed the formation of the desired intermediate (412.09 calcd for C$_{20}$H$_{16}$N$_2$O$_8$; obsd.: 412.96 (M+H)$^+$, 434.93 (M+Na)$^+$, and 450.93 (M+K)$^+$).

The above residue was dissolved in DMF (0.5 mL). N-hydroxysuccinimide (39.8 mg, 0.348 mmol), DMAP (5.0 mg) and ED—HCl (39.8 mg, 0.208 mmol) were added. The mixture was stirred at r.t. overnight. It was then diluted with EtOAc, washed with sat. NH$_4$Cl, dried over Na$_2$SO$_4$, and concentrated. The residue was purified by FC (hexane/EtOAc, 2:3) to give the product (40.2 mg, 46% for two steps). $^1$H NMR (400 MHz, δ ppm, CDCl$_3$): 9.19 (t, J=6.0 Hz, 1 H), 8.79 (s, 1 H), 8.07 (dd, J=8.0, 1,0 Hz, 1 H), 7.22-7.71 (m, 4 H), 6.90 (dd, J=8.0, 1.0 Hz, 1 H), 6.73 (d, J=1.0 Hz, 1 H), 6.18 (m, 1 H), 4.56 (d, J=6.0 Hz, 2H), 2.84 (s, 4 H), 1.75 (d, J=6.4 Hz, 3H). MS: 509.11 calcd for C$_{24}$H$_{19}$N$_3$O$_{10}$; obsd.: 510.01 (M+H)$^+$, 532.00 (M+Na)$^+$, 547.9 (M+K)$^+$.

While the compositions and methods of this invention have described in terms of preferred embodiments, it will be apparent to those of skill in the art that variations maybe applied to the composition, methods and in the steps or in the sequence of steps of the method described herein without departing from the concept, spirit and scope of the invention. More specifically, it will be apparent that certain agents that are chemically related might be substituted for the agents described herein while the same or similar results would be achieved. All such similar substitutes and modifications to those skilled in the art are deemed to be within the spirit, scope and concept of the invention as defined by the appended claims.

What is claimed is:

1. A photo-caged fluorophore having the structure:

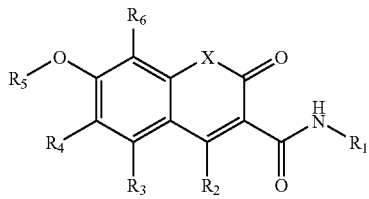

wherein

X is O;

R₁ is any linear or branched alkyl chains up to 20 carbon atoms or any one of the 20 amino acids either in D or L configuration;

R₂ is H, alkyl groups up to 6 carbon atoms, F, Cl, Br, CF₃, CHF₂, or CH₂F;

R₃ is H, F, Cl, or Br;

R₄ and R₆ are independently H, F, Cl, or Br, but not both F; and

R₅ is selected from the group consisting of:

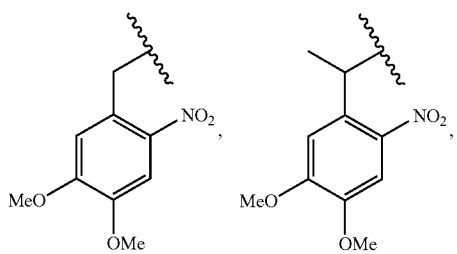

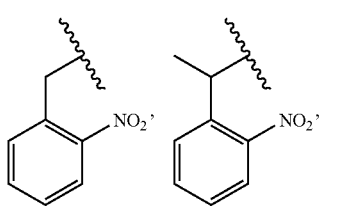

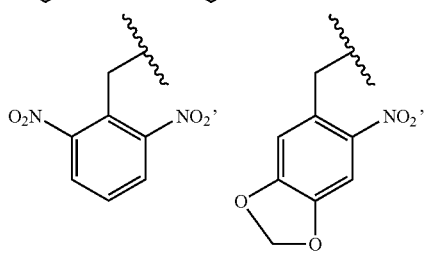

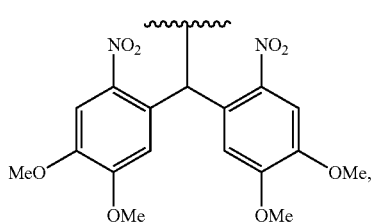

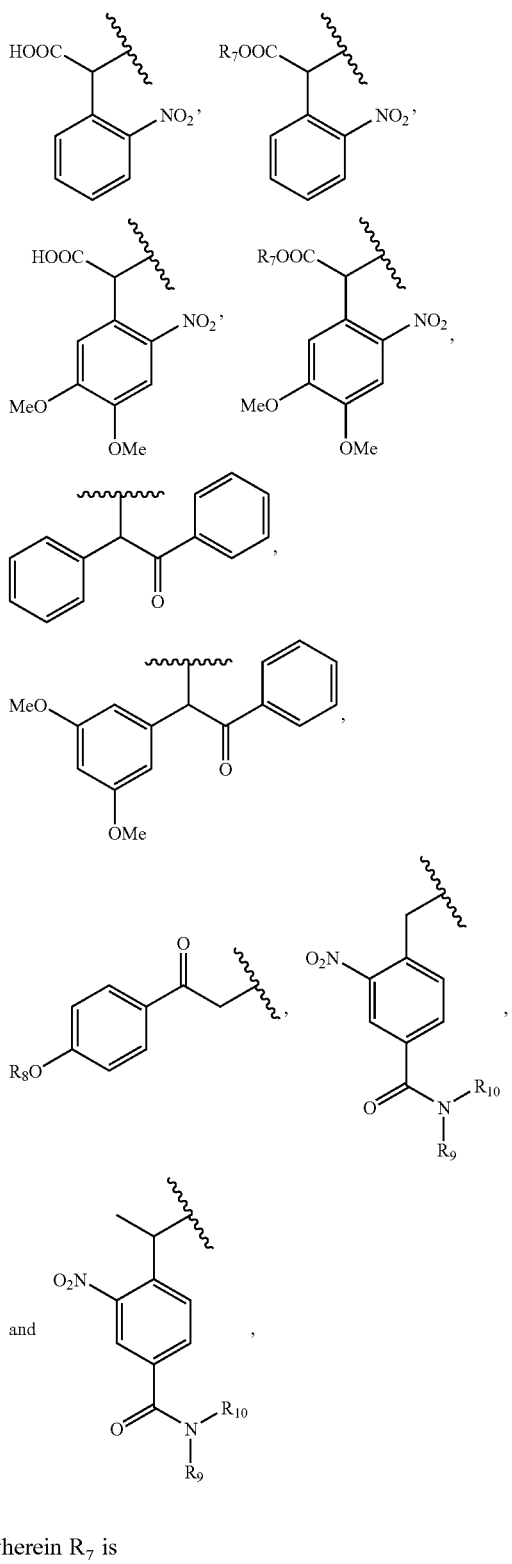

wherein R₇ is

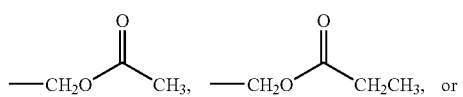

-continued
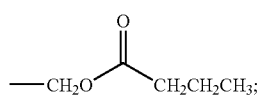
$R_8$ is H, $CH_3$, or $CH_3CO$; and
$R_9$ and $R_{10}$ are independently the same or different and are H, linear or branched alkyl chains containing from 1 to 10 carbons, or acetates.
2. A photo-caged fluorophore having the structure:
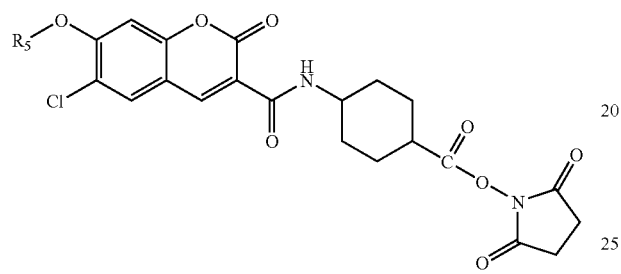
wherein $R_5$ is selected from the group consisting of:
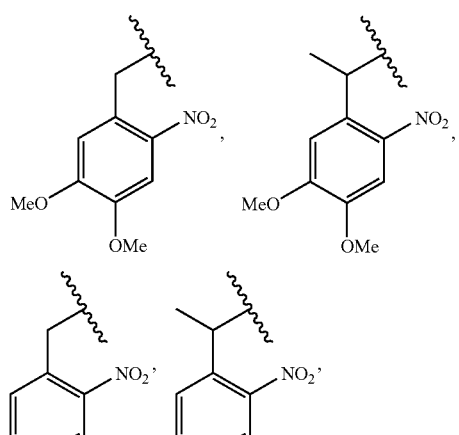
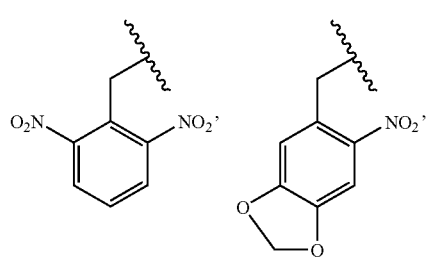
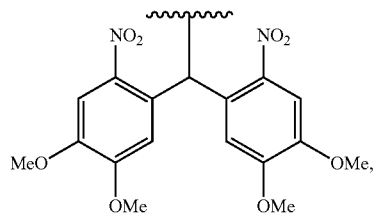
-continued
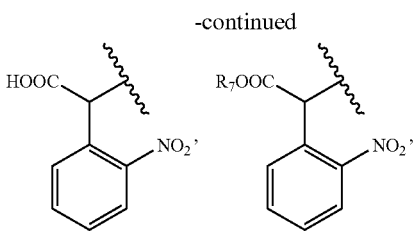
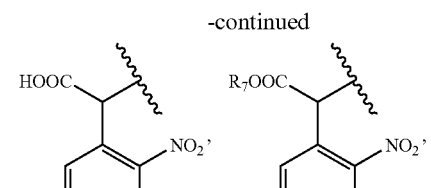
wherein $R_7$ is
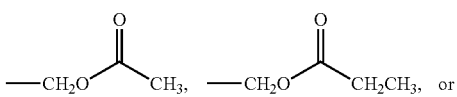

-continued
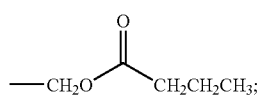
$R_8$ is H, $CH_3$, or $CH_3CO$; and
$R_9$ and $R_{10}$ are independently the same or different and are H, linear or branched alkyl chains containing from 1 to 10 carbons, or acetates.
3. A photo-caged fluorophore having the structure:
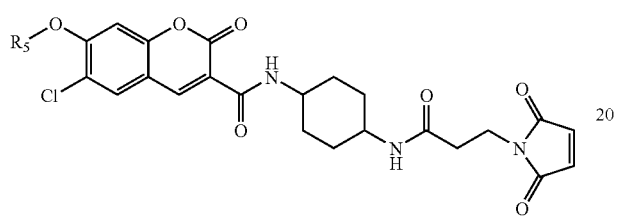
wherein $R_5$ is selected from the group consisting of:
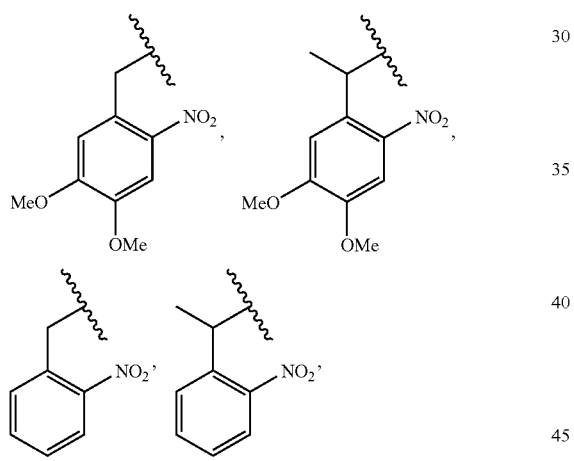
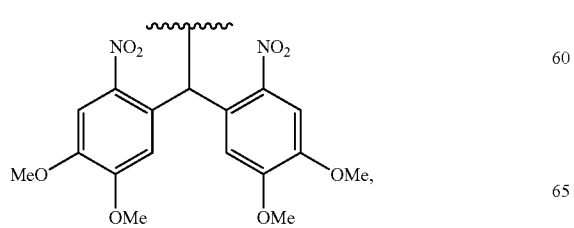
-continued
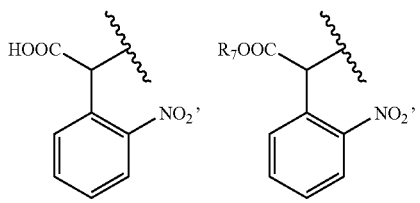
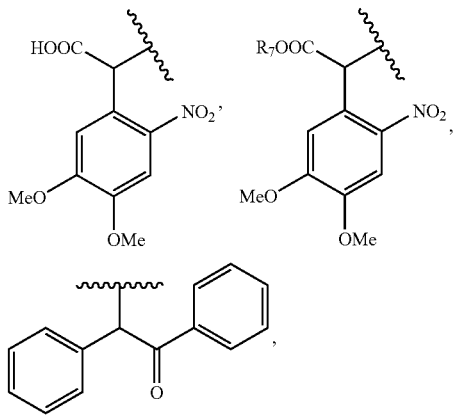
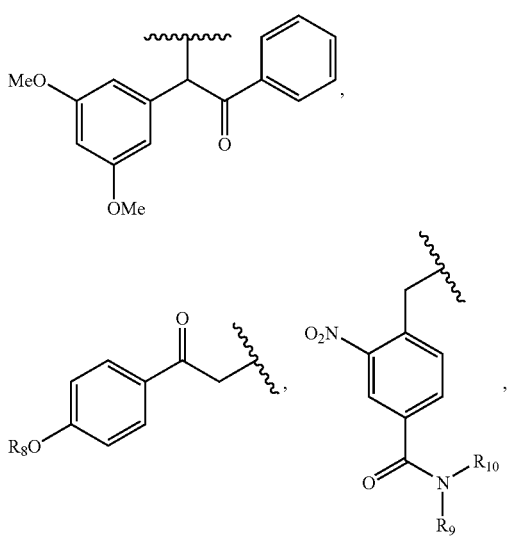
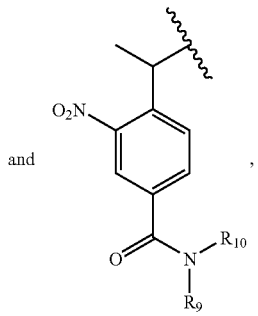
wherein $R_7$ is
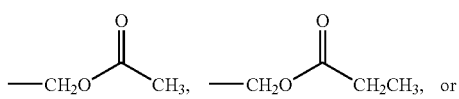

-continued
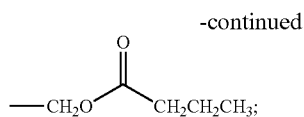
$R_8$ is H, $CH_3$, or $CH_3CO$; and
$R_9$ and $R_{10}$ are independently the same or different and are H, linear or branched alkyl chains containing from 1 to 10 carbons, or acetates.
4. A photo-caged fluorophore having a structure selected from the group consisting of:
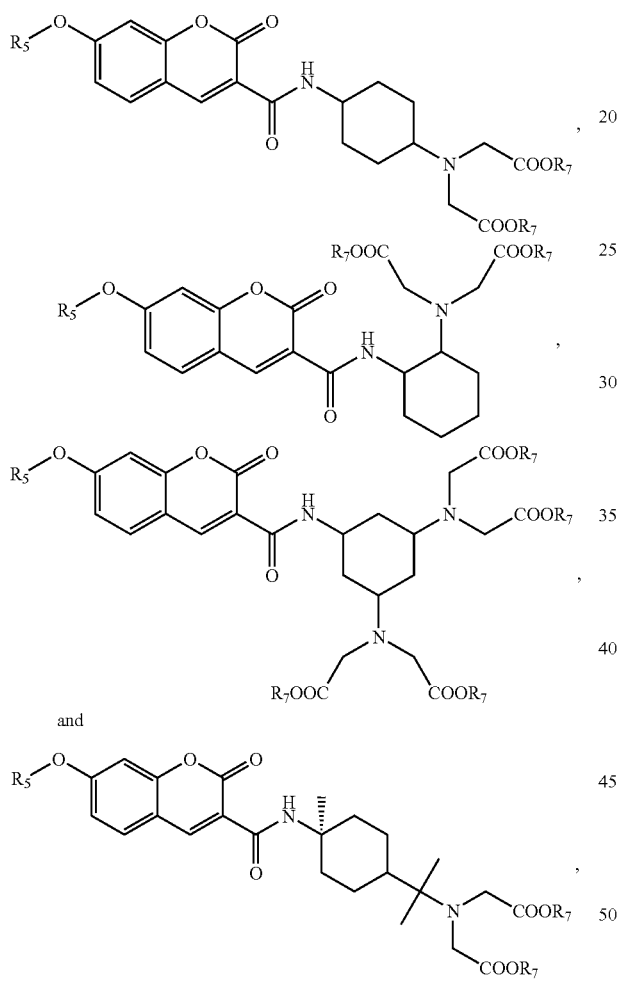
and
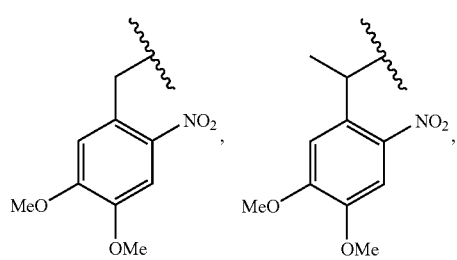
wherein $R_5$ s selected from the group consisting of:
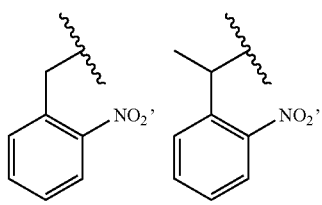
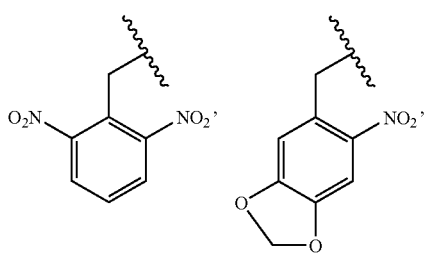
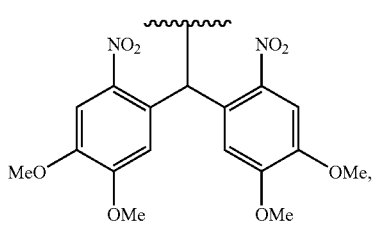
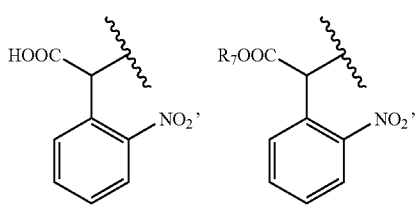
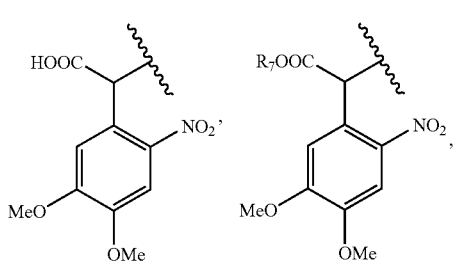
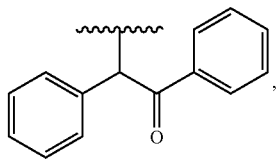
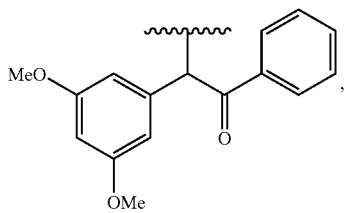

-continued

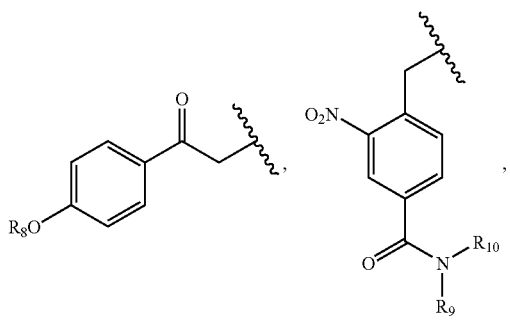

and

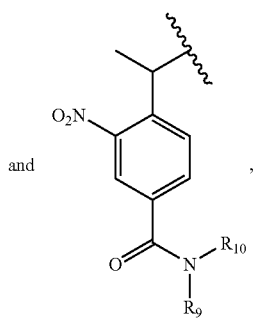

wherein $R_7$ is

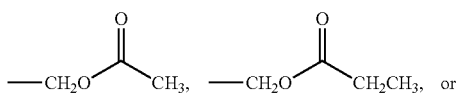

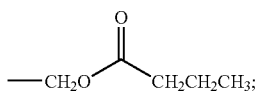

$R_8$ is H, $CH_3$, or $CH_3CO$; and $R_9$ and $R_{10}$ are independently the same or different and are H, linear or branched alkyl chains containing from 1 to 10 carbons, or acetates.

5. A photo-caged fluorophore having the structure:

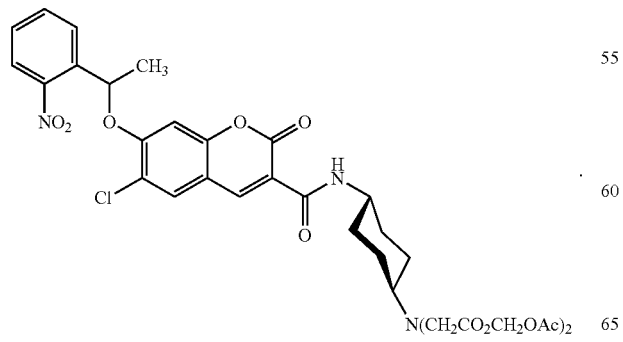

6. A photo-caged fluorophore having the structure:

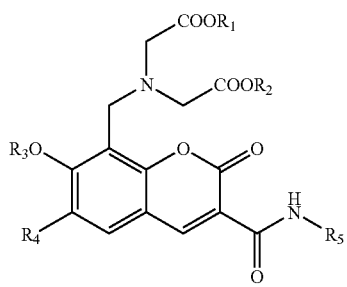

wherein $R_1$ and $R_2$ independently are the same or different and are

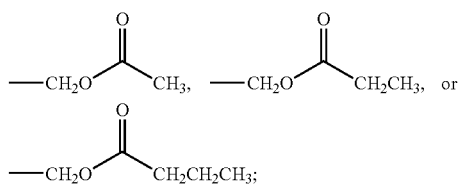

$R_4$ is H, F, or Cl;

$R_5$ is a linear or branched alkyl chain containing from 1 to 18 carbons, a D or L amino acid or its derivative, a diamine, a cyclohexane amine, or an adamantanamine derivative; and $R_3$ is selected from the group consisting of

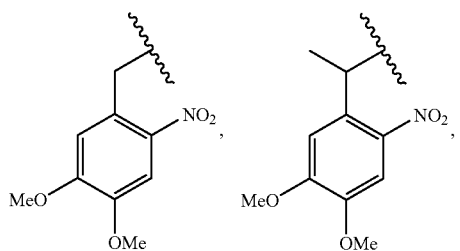

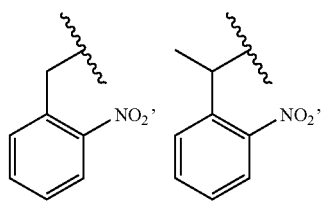

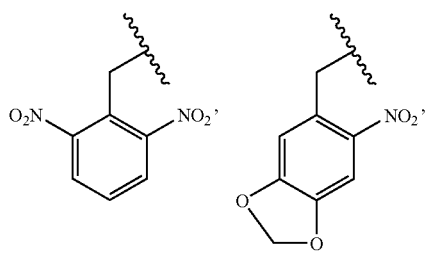

-continued
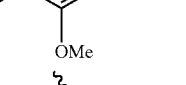
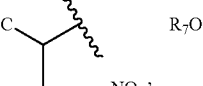 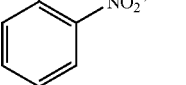
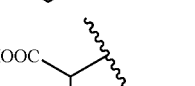 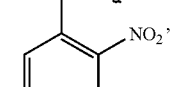
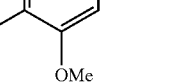
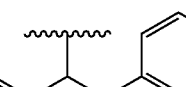
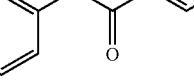 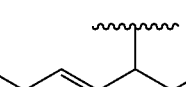
and 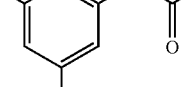,
wherein $R_7$ is
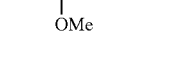 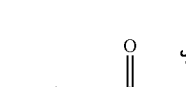 or
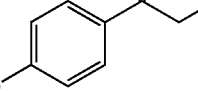;
$R_8$ is H, $CH_3$, or $CH_3CO$; and
$R_9$ and $R_{10}$ are independently the same or different and are H, linear or branched alkyl chains containing from 1 to 10 carbons, or acetates.
7. A photo-caged fluorophore having a structure selected from the group consisting of:
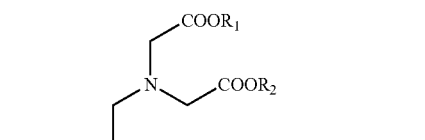,
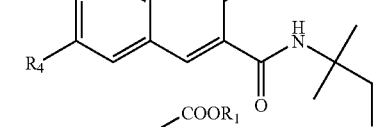,
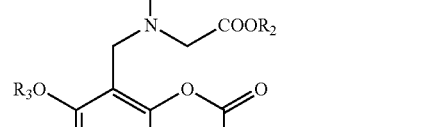,
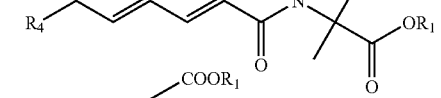,
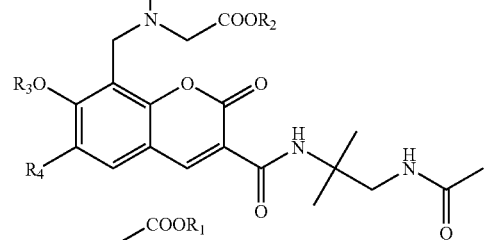,
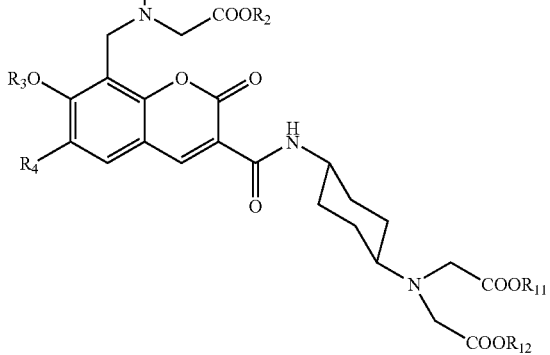

-continued
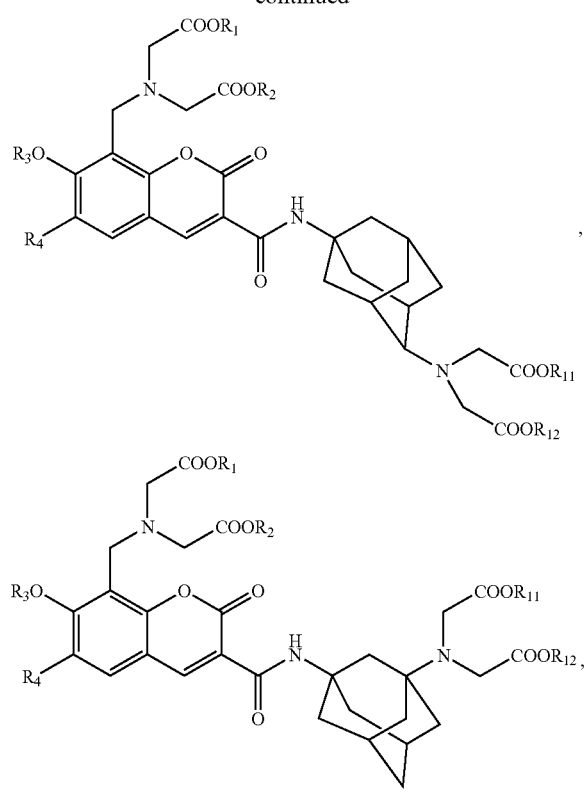
and
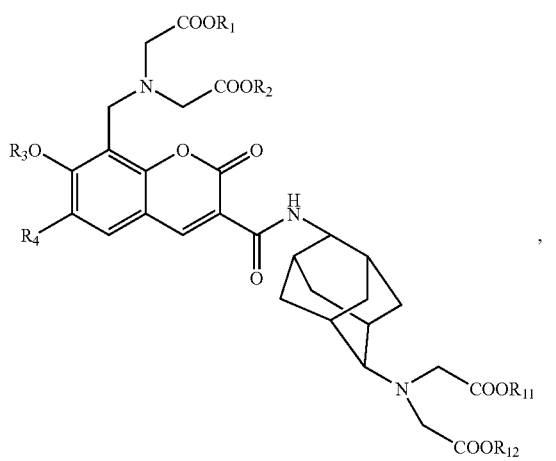
wherein
$R_1$, $R_2$, $R_{11}$, and $R_{12}$ independently are the same or different and are
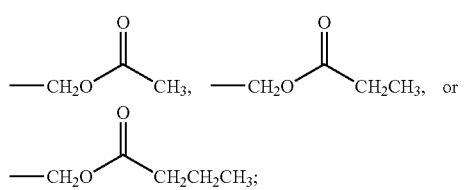
$R_4$ is H, F, or Cl; and
$R_3$ is selected from the group consisting of
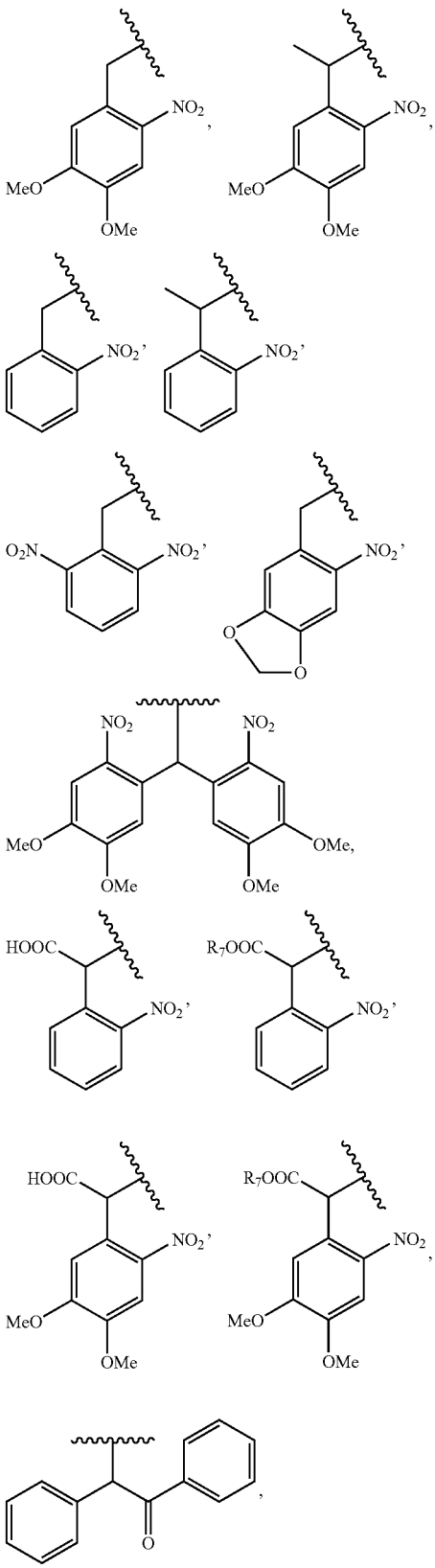

-continued
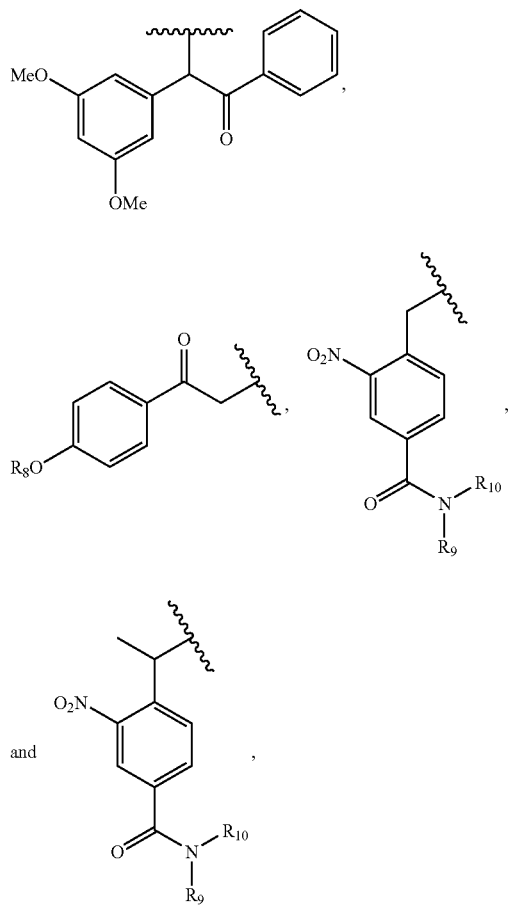
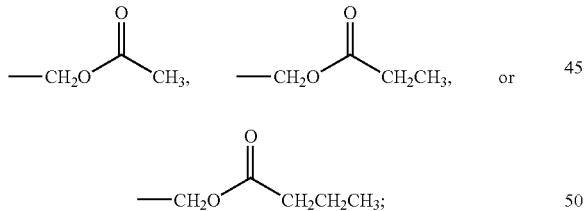
wherein $R_7$ is
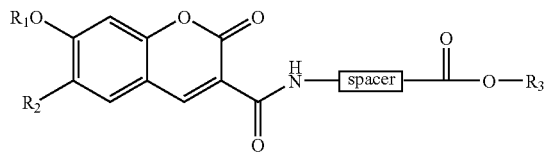
$R_8$ is H, CH$_3$, or CH$_3$CO; and
$R_9$ and $R_{10}$ are independently the same or different and are H, linear or branched alkyl chains containing from 1 to 10 carbons, or acetates.
8. A photo-caged fluorophore having the structure:
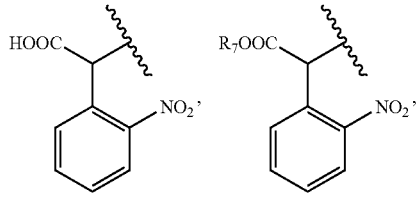
wherein the spacer is part of an amino acid;
$R_2$ is H, F, or Cl;
$R_3$ is
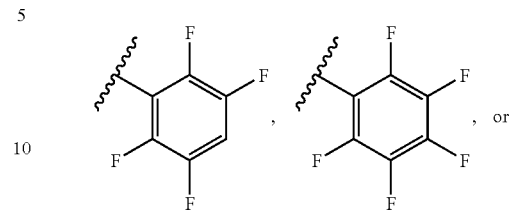
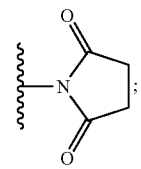
and
$R_1$ is a caging group selected from the group consisting of
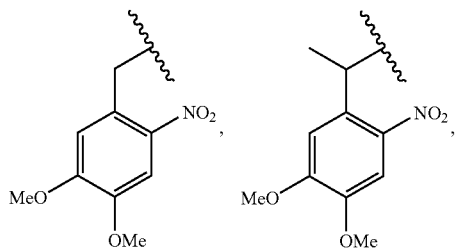
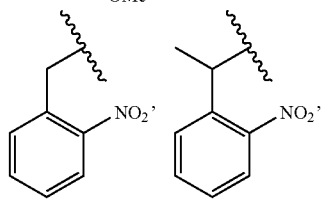
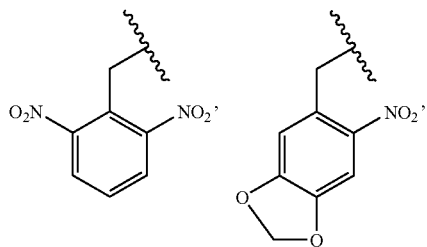
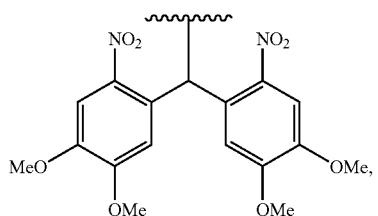

-continued
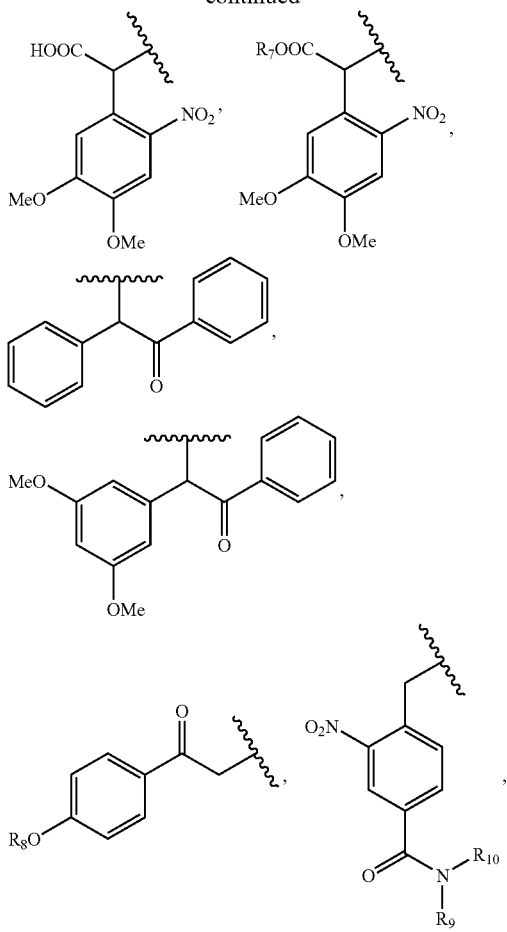
and
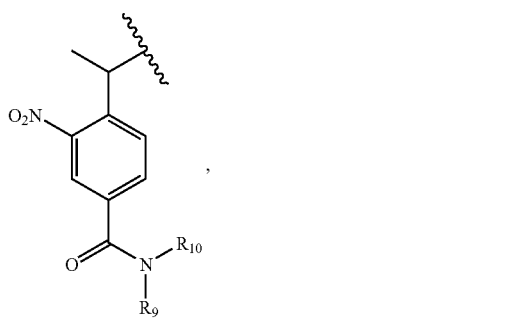
wherein $R_7$ is
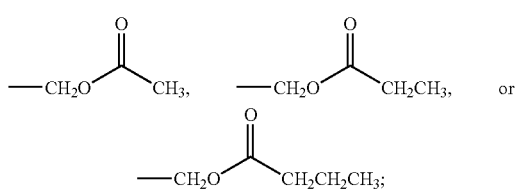
$R_8$ is H, CH$_3$, or CH$_3$CO; and
$R_9$ and $R_{10}$ are independently the same or different and are H, linear or branched alkyl chains containing from 1 to 10 carbons, or acetates.
9. A photo-caged fluorophore having the structure:
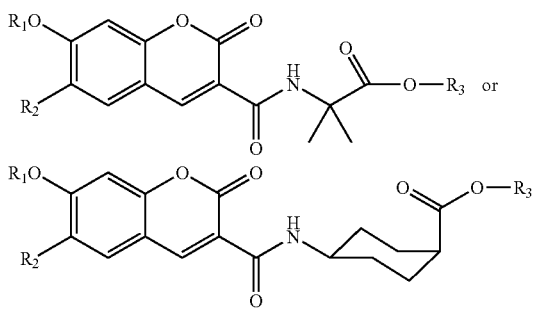
wherein $R_2$ is H, F, or Cl;
$R_3$ is
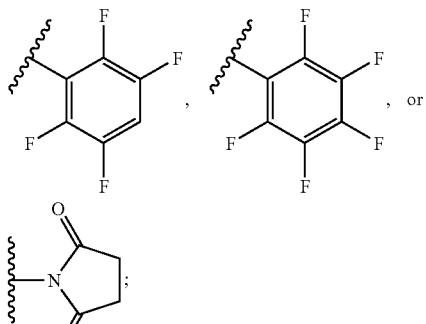
and
$R_1$ is a caging group selected from the group consisting of
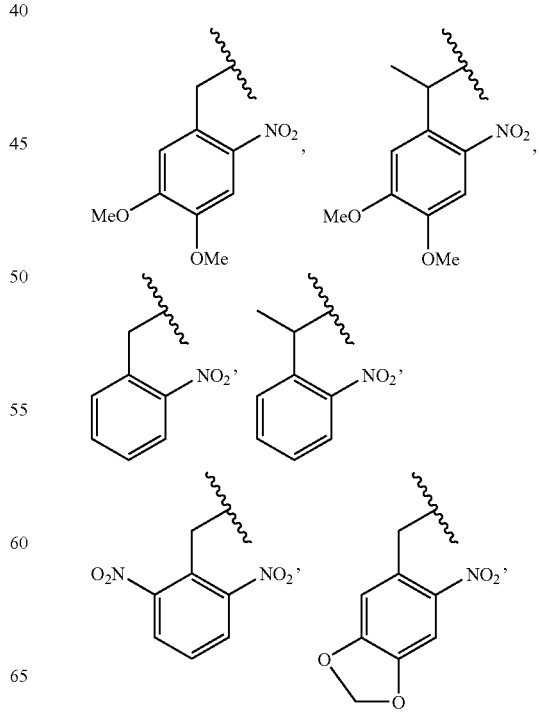

-continued
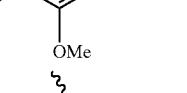
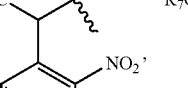
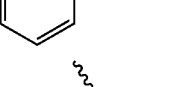
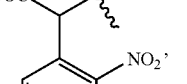
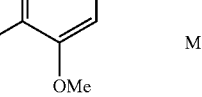
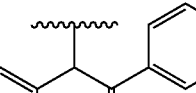
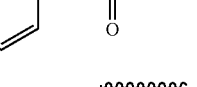
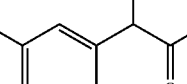
and 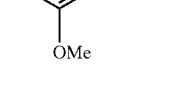
wherein $R_7$ is
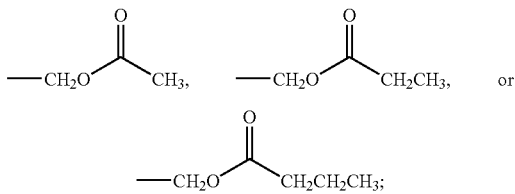
$R_8$ is H, $CH_3$, or $CH_3CO$; and
$R_9$ and $R_{10}$ are independently the same or different and are H, linear or branched alkyl chains containing from 1 to 10 carbons, or acetates.
10. A photo-caged fluorophore having the structure:
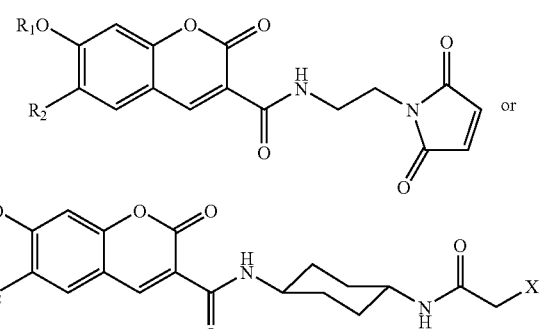
wherein X is Br or I;
$R_2$ is H, F, or Cl; and
$R_1$ is a caging group selected from the group consisting of
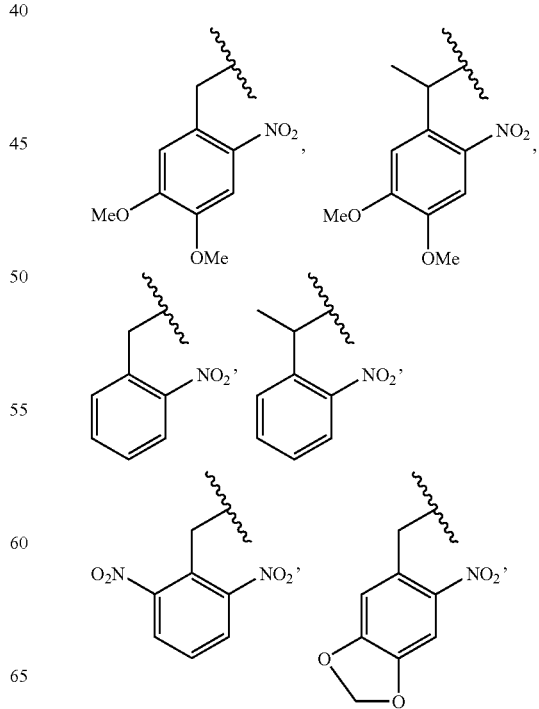

-continued
 
 
,
,
-continued
, ,
and ,
wherein $R_7$ is
, 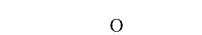, or
;
$R_8$ is H, $CH_3$, or $CH_3CO$; and
$R_9$ and $R_{10}$ are independently the same or different and are H, linear or branched alkyl chains containing from 1 to 10 carbons, or acetates.
* * * * *